United States Patent
Shi et al.

(10) Patent No.: US 10,641,698 B2
(45) Date of Patent: May 5, 2020

(54) METHODS FOR COMPLETE BLOOD COUNT MEASUREMENT

(71) Applicant: CYTOCHIP INC., Irvine, CA (US)

(72) Inventors: Wendian Shi, Monrovia, CA (US); Yuzhe Ding, Monrovia, CA (US)

(73) Assignee: CYTOCHIP INC., Irvine, CA (US)

( * ) Notice: Subject to any disclaimer, the term of this patent is extended or adjusted under 35 U.S.C. 154(b) by 130 days.

(21) Appl. No.: 15/819,416

(22) Filed: Nov. 21, 2017

(65) Prior Publication Data

US 2018/0095023 A1 Apr. 5, 2018

Related U.S. Application Data

(63) Continuation-in-part of application No. 15/803,133, filed on Nov. 3, 2017, and a continuation-in-part of (Continued)

(51) Int. Cl.
*G01N 15/14* (2006.01)
*G01N 15/06* (2006.01)
(Continued)

(52) U.S. Cl.
CPC ...... *G01N 15/1404* (2013.01); *B01L 3/50273* (2013.01); *B01L 3/502715* (2013.01); *B01L 3/502723* (2013.01); *B01L 3/502738* (2013.01); *B01L 3/502761* (2013.01); *G01N 15/06* (2013.01); *G01N 15/1459* (2013.01); *G01N 15/1484* (2013.01); *G01N 21/05* (2013.01);
(Continued)

(58) Field of Classification Search
CPC ........ G01N 15/06; G01N 35/00; G01N 15/14; G01N 15/00; G01N 15/1404; G01N 2015/1409; G01N 2015/1411; G01N 2015/1413; G01N 15/1484; G01N 33/5094; G01N 33/56972; G01N 33/80; A61B 10/0096; B01L 3/5027; B01L 3/502715; B01L 3/502723; B01L 3/50273; B01L 3/502738; B01L 3/502761
USPC ......... 422/68.1, 502, 503, 504, 554; 436/43, 436/174, 180
See application file for complete search history.

(56) References Cited

U.S. PATENT DOCUMENTS 8,361,410 B2 1/2013 Padmanabhan et al.
8,940,499 B2 1/2015 Kuang et al.
(Continued)

OTHER PUBLICATIONS

PCT Application No. PCT/US2017/062765, International Preliminary Report on Patentability, dated Jun. 6, 2019, 12 pages.
(Continued)

*Primary Examiner* — Brian J. Sines
(74) *Attorney, Agent, or Firm* — Lathrop GPM LLP

(57) ABSTRACT

The disclosure relates to devices and methods for analyzing blood cells in a sample. In various embodiments, the present disclosure provides devices and methods of performing complete blood count (CBC) testing. In various embodiments, the present disclosure provides a cartridge device and a reader instrument device, wherein the reader instrument device receives, operates, and/or actuates the cartridge device. In various embodiments, the present disclosure provides a method of using a device as disclosed herein for analyzing blood cells in a sample.

35 Claims, 31 Drawing Sheets

Related U.S. Application Data application No. 15/209,226, filed on Jul. 13, 2016, now Pat. No. 10,077,999, and a continuation-in-part of application No. 15/176,729, filed on Jun. 8, 2016, now Pat. No. 10,022,720.

(60) Provisional application No. 62/425,395, filed on Nov. 22, 2016, provisional application No. 62/497,075, filed on Nov. 7, 2016, provisional application No. 62/192,488, filed on Jul. 14, 2015, provisional application No. 62/174,776, filed on Jun. 12, 2015.

(51) Int. Cl.

| | | |
|---|---|---|
| *G01N 35/00* | (2006.01) | |
| *B01L 3/00* | (2006.01) | |
| *G01N 33/50* | (2006.01) | |
| *G01N 33/72* | (2006.01) | |
| *G01N 33/543* | (2006.01) | |
| *G01N 33/80* | (2006.01) | |
| *G01N 21/53* | (2006.01) | |
| *G01N 21/64* | (2006.01) | |
| *G01N 21/85* | (2006.01) | |
| *G01N 21/05* | (2006.01) | |
| *G01N 15/00* | (2006.01) | |
| *G01N 15/10* | (2006.01) | |

(52) U.S. Cl.
CPC ......... *G01N 21/53* (2013.01); *G01N 21/6486* (2013.01); *G01N 21/85* (2013.01); *G01N 33/5094* (2013.01); *G01N 33/54366* (2013.01); *G01N 33/726* (2013.01); *G01N 33/80* (2013.01); *B01L 2200/143* (2013.01); *B01L 2300/0645* (2013.01); *B01L 2300/0654* (2013.01); *B01L 2300/0681* (2013.01); *B01L 2300/087* (2013.01); *B01L 2300/0864* (2013.01); *B01L 2300/0867* (2013.01); *B01L 2300/0877* (2013.01); *B01L 2300/0887* (2013.01); *B01L 2300/161* (2013.01); *B01L 2300/168* (2013.01); *B01L 2400/0406* (2013.01); *B01L 2400/0409* (2013.01); *B01L 2400/0457* (2013.01); *B01L 2400/0487* (2013.01); *B01L 2400/0688* (2013.01); *B01L 2400/088* (2013.01); *G01N 2015/008* (2013.01); *G01N 2015/0065* (2013.01); *G01N 2015/0073* (2013.01); *G01N 2015/0084* (2013.01); *G01N 2015/0687* (2013.01); *G01N 2015/0693* (2013.01); *G01N 2015/1006* (2013.01); *G01N 2015/1486* (2013.01)

(56) References Cited

U.S. PATENT DOCUMENTS

| | | |
|---|---|---|
| 2003/0030783 A1 | 2/2003 | Roche et al. |
| 2006/0177347 A1 | 8/2006 | Larsen et al. |
| 2008/0085560 A1 | 4/2008 | Ekberg |
| 2013/0130262 A1 | 5/2013 | Battrell et al. |
| 2014/0211205 A1 | 7/2014 | Bardell et al. |
| 2014/0356941 A1 | 12/2014 | Bransky et al. |
| 2016/0361715 A1 | 12/2016 | Shi et al. |
| 2017/0160186 A1* | 6/2017 | Fox .................. G01N 1/286 |
| 2018/0313742 A1* | 11/2018 | Fox .................. G01N 1/286 |

OTHER PUBLICATIONS

PCT Application No. PCT/US2017/062765, International Search Report and Written Opinion, dated Jan. 29, 2018, 4 pages.

Maleki T et al., Point-Of_Care, Portable Microfluidic Blood Analyzer System, Microfluidics, BioMEMS, and Medical Microsystems X, Feb. 9, 2012, abstract, pp. 3-5, 7, 9.

Ducree, J. et al., The Centrifugal Microfluidic Bio-Disk Platform, Journal of Micromechanics and Microengineering, Jun. 28, 2007, pp. S103-S115, pp. S105, S107.

* cited by examiner

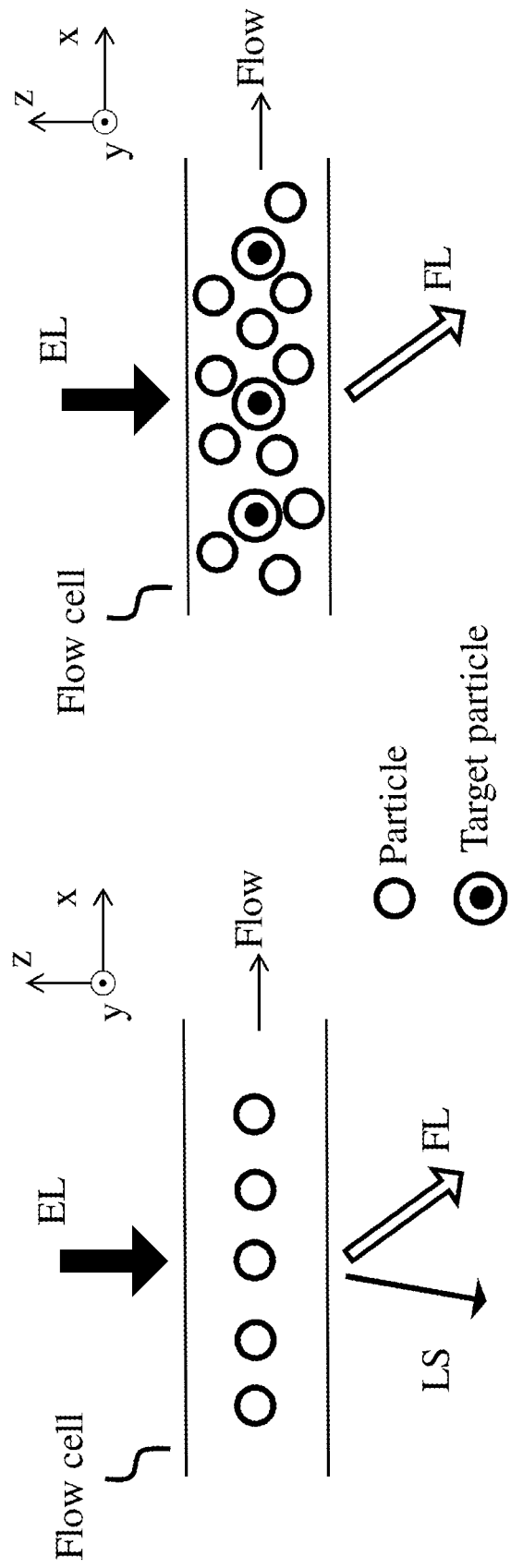

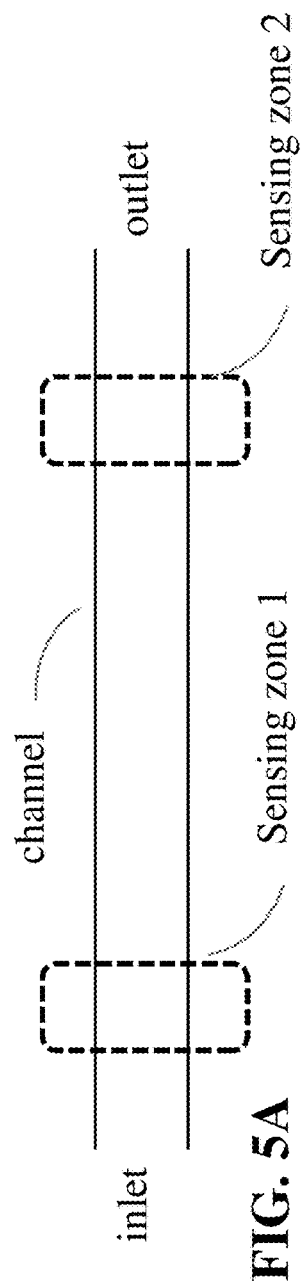
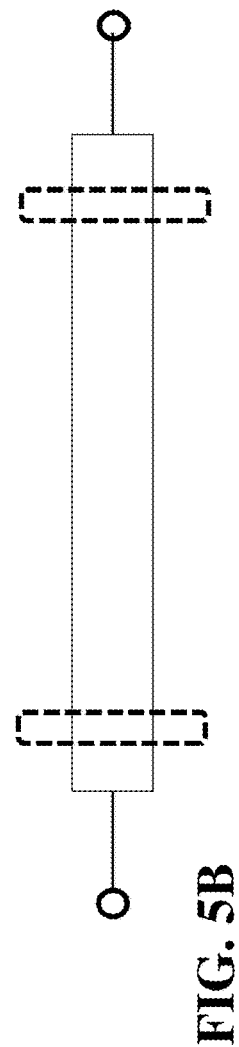
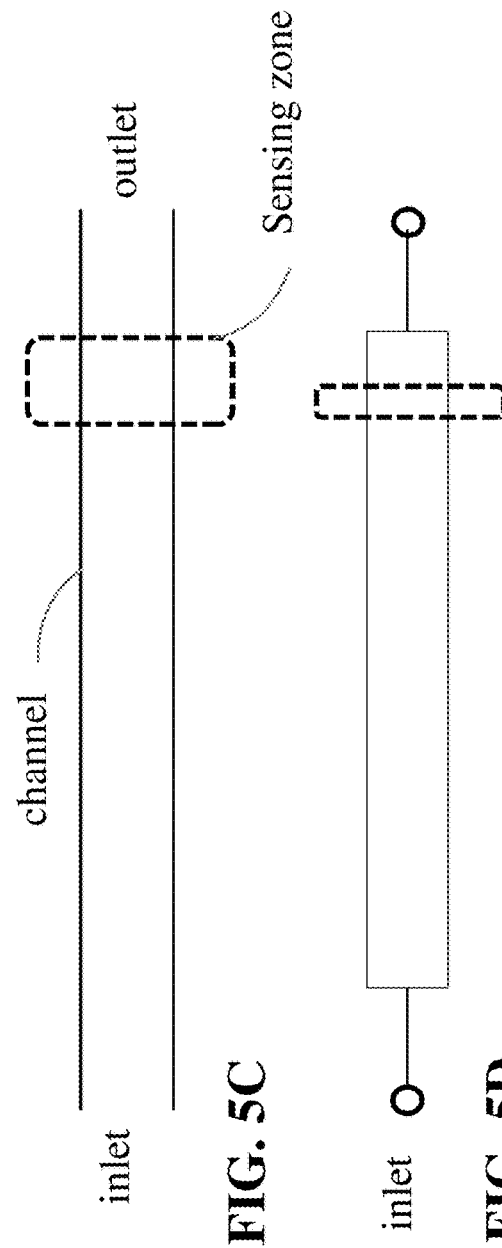
FIG. 5A
FIG. 5B
FIG. 5C
FIG. 5D

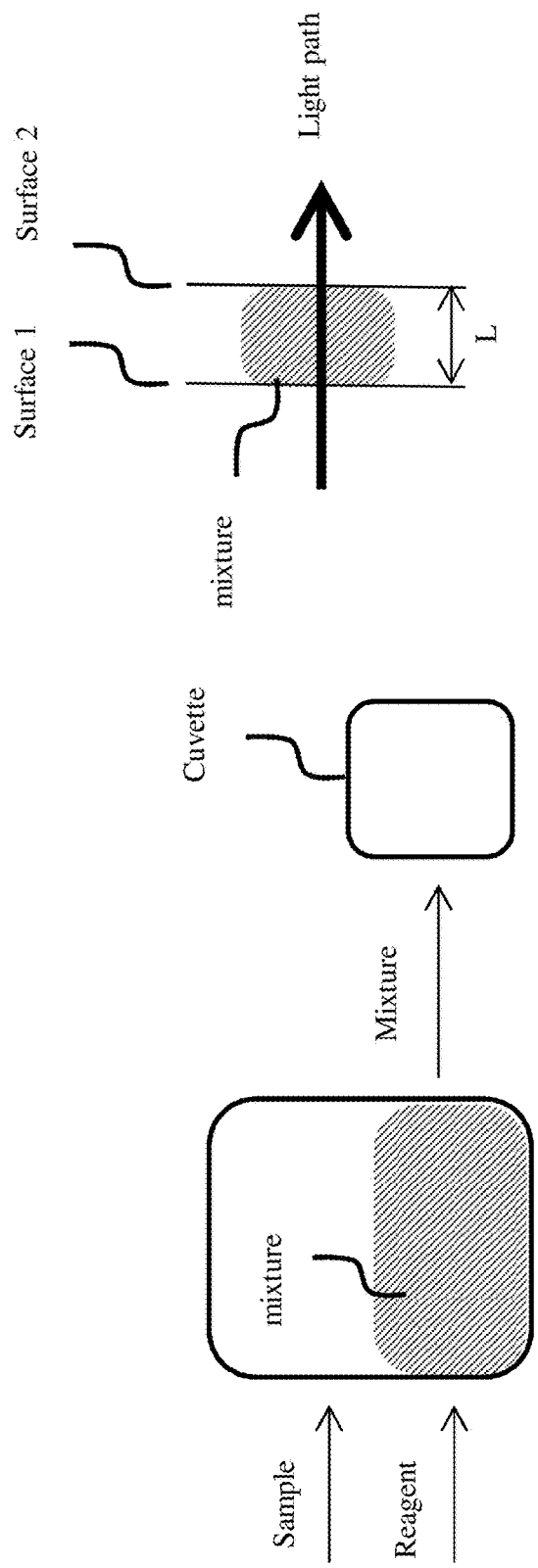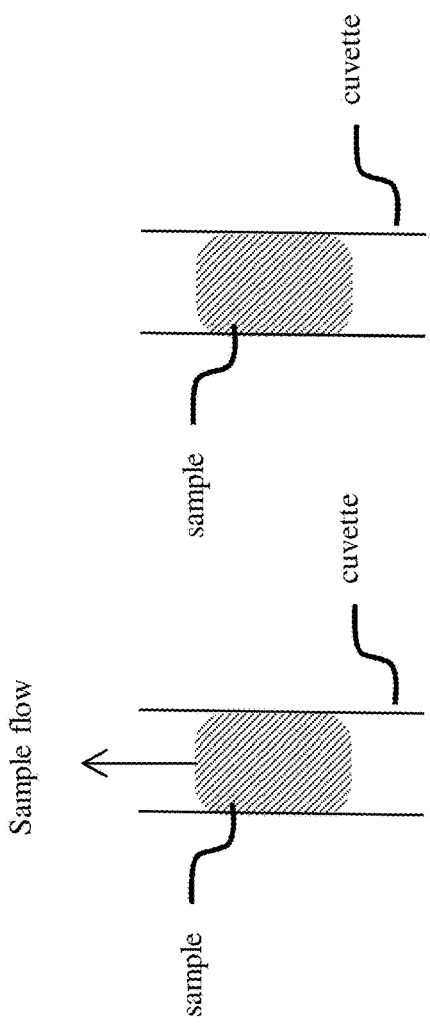
FIG. 10A
FIG. 10B
FIG. 11A
FIG. 11B

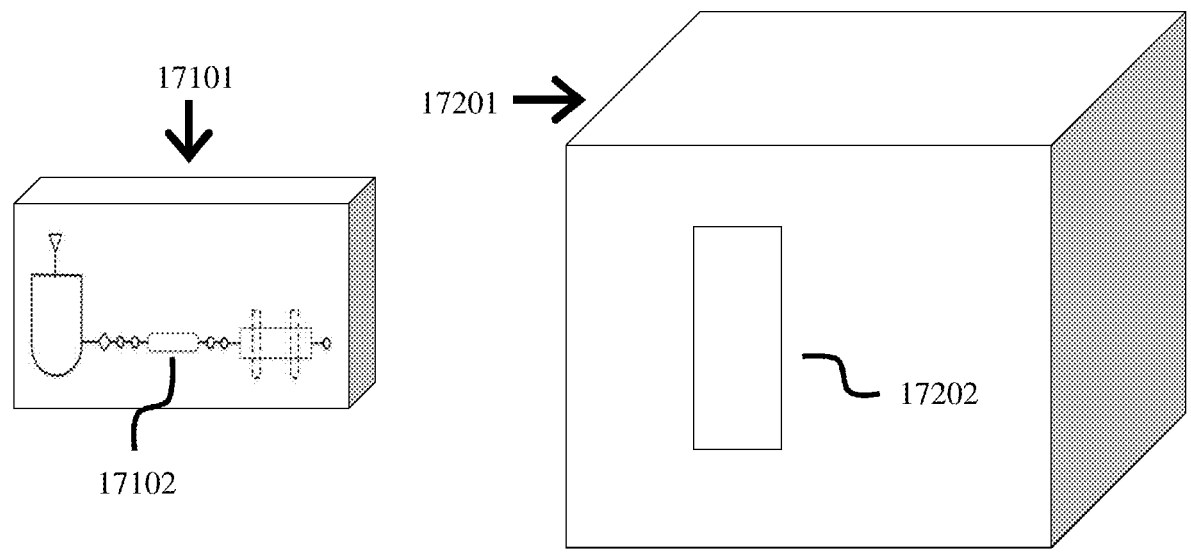
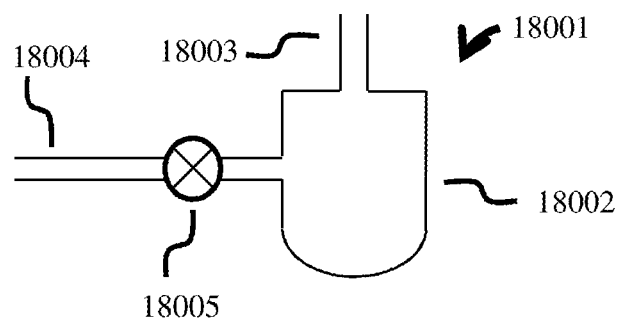
FIG. 18A
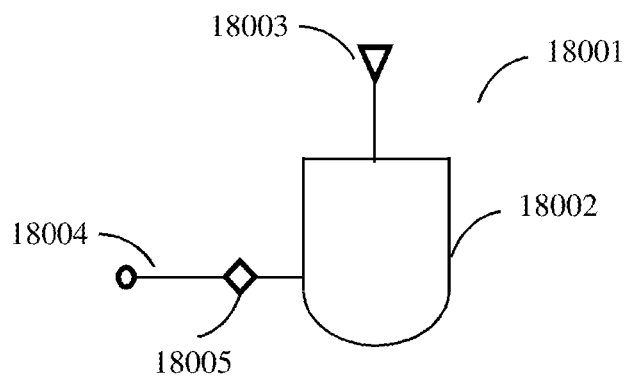
FIG. 18B

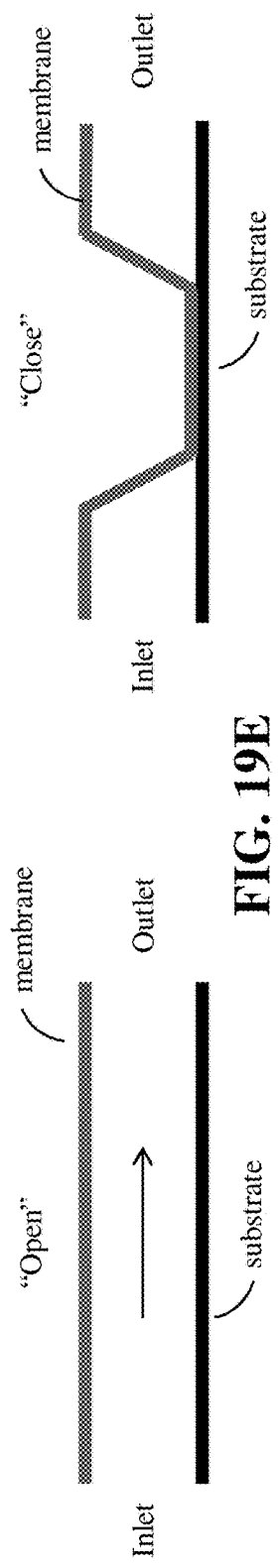
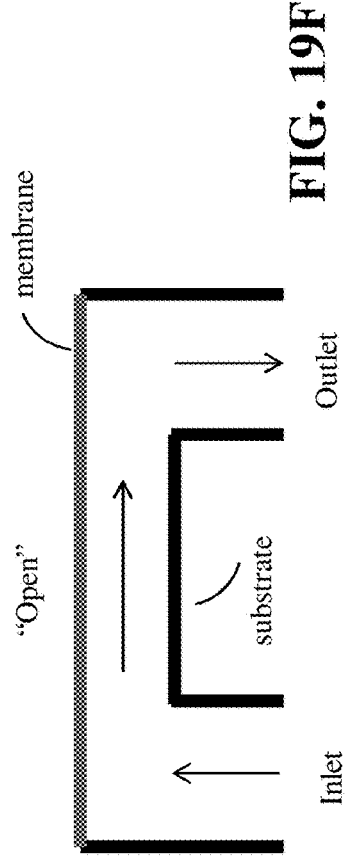
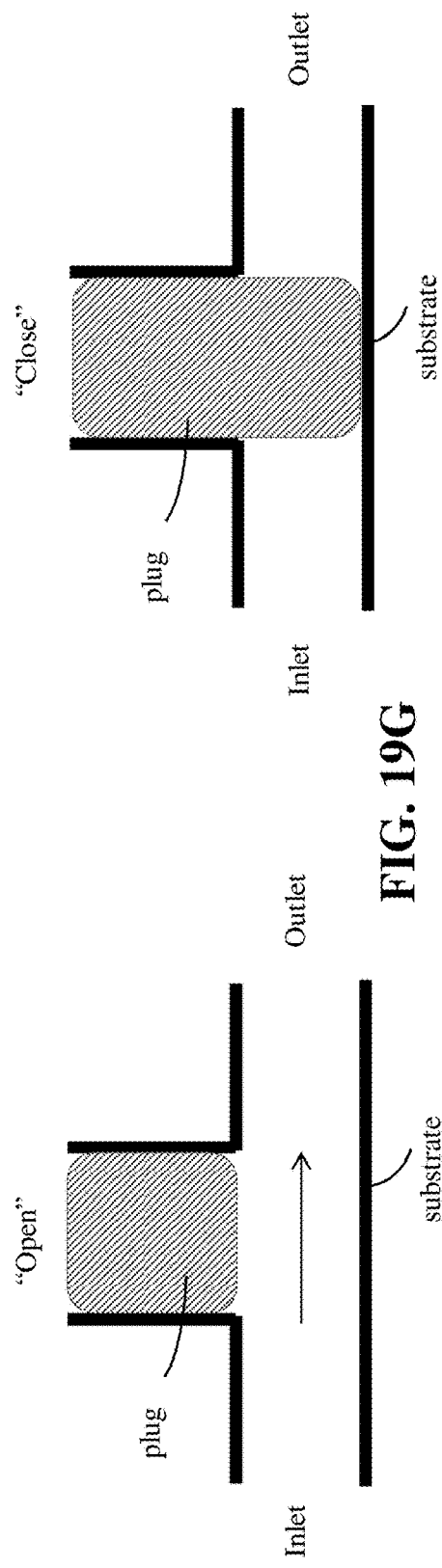
FIG. 19E
FIG. 19F
FIG. 19G

METHODS FOR COMPLETE BLOOD COUNT MEASUREMENT

PRIORITY CLAIM

This application claims priority to U.S. Provisional Patent Application No. 62/425,395, filed on Nov. 22, 2016, entitled "Methods for Complete Blood Count Measurement", the entire contents of which are incorporated herein by reference and relied upon.

This application is a continuation-in-part of U.S. patent application Ser. No. 15/176,729, filed on Jun. 8, 2016, entitled "Fluidic Units and Cartridges for Multi-Analyte Analysis", which claims priority to U.S. Provisional Patent Application No. 62/174,776, filed on Jun. 12, 2015, the entire contents of each of which are incorporated herein by reference and relied upon.

This application is related to International Application PCT/US2016/036426, filed on Jun. 8, 2016, entitled "Fluidic Units and Cartridges for Multi-Analyte Analysis", which claims priority to U.S. Provisional Patent Application No. 62/174,776, filed on Jun. 12, 2015, the entire contents of each of which are incorporated herein by reference and relied upon.

This application is a continuation-in-part of U.S. patent application Ser. No. 15/209,226, filed on Jul. 13, 2016, entitled "Volume Sensing in Fluidic Cartridge", which claims priority to U.S. Provisional Patent Application No. 62/192,488, filed on Jul. 14, 2015, the entire contents of each of which are incorporated herein by reference and relied upon.

This application is related to International Application PCT/US2016/042089, filed on Jul. 13, 2016, entitled "Volume Sensing in Fluidic Cartridge", which claims priority to U.S. Provisional Patent Application No. 62/192,488, filed on Jul. 14, 2015, the entire contents of each of which are incorporated herein by reference and relied upon.

This application is a continuation-in-part of U.S. patent application Ser. No. 15/803,133, filed on Nov. 3, 2017, entitled "Fluidic Cartridge for Cytometry and Additional Analysis", which claims priority to U.S. Provisional Patent Application No. 62/497,075, filed on Nov. 7, 2016, the entire contents of each of which are incorporated herein by reference and relied upon.

This application is related to International Application PCT/US2017/59965, filed on Nov. 3, 2017, entitled "Fluidic Cartridge for Cytometry and Additional Analysis", which claims priority to U.S. Provisional Patent Application No. 62/497,075, filed on Nov. 7, 2016, and U.S. patent application Ser. No. 15/803,133, filed on Nov. 3, 2017, the entire contents of each of which are incorporated herein by reference and relied upon.

FIELD OF THE DISCLOSURE

The disclosure relates to medicine and cytometry.

BACKGROUND

All publications cited herein are incorporated by reference in their entirety to the same extent as if each individual publication or patent application was specifically and individually indicated to be incorporated by reference. The following description includes information that may be useful in understanding the present disclosure. It is not an admission that any of the information provided herein is prior art or relevant to the presently disclosure, or that any publication specifically or implicitly referenced is prior art.

Complete blood count (CBC) is a frequently used diagnostic test in clinics. It measures a blood sample for parameters such as leukocyte count, erythrocyte count, platelet count, hemoglobin concentration and hematocrit. It may also measure additional leukocyte parameters such as leukocyte differential (e.g., lymphocyte, monocyte, neutrophil, eosinophil, and basophil), reticulocyte count, nucleated erythrocyte count, erythrocyte indices (e.g., hematocrit, mean corpuscular volume (MCV), mean corpuscular hemoglobin (MCH), mean corpuscular hemoglobin concentration (MCHC), and red cell distribution width (RDW)), and platelet indices (e.g., mean platelet volume (MPV), plateletcrit (PCT), platelet distribution width (PDW), and platelet large cell ratio (PLCR)).

Testing of CBC is usually performed on automated hematology analyzers. These analyzers have a fluidic system that processes blood samples with different reagents and delivers them for sensing signal measurements. In conventional hematology analyzers, this fluidic system is built into the instrument for continuous use. After measuring one sample, the system needs to be flushed with a cleaning reagent to remove any residual sample. In point-of-care applications, an alternative format of the fluidic system is a disposable cartridge. The cartridge has on-board fluidics and is inserted into an instrument before testing a sample, and replaced after measurement. Each sample can be measured in a new cartridge, and there is no residual sample from the previous measurement.

U.S. Pat. Nos. 7,771,658 and 8,573,033 discuss methods of using a cartridge having on-board fluidics to perform the CBC test. In these methods, measurements of electrical impedance are used to detect the cells in the blood such as leukocytes, erythrocytes, and platelets. In comparison to this electrical impedance method, optical measurements are often preferred for CBC testing. For one reason, optical measurements achieve higher accuracy of CBC testing. Electrical impedance method can distinguish leukocyte cells into three subtypes including lymphocytes, monocytes and granulocytes, whereas optical method can distinguish leukocyte cells into five subtypes including lymphocytes, monocytes, and granulocytes, and can further distinguish granulocytes into neutrophil, eosinophil and basophil cells.

U.S. Pat. Nos. 8,741,233 and 8,741,234 discuss methods of using a cartridge having on-board fluidics to perform the CBC test with optical measurements. In these methods, a cytometer flow cell with a sheath flow design was used for the optical measurements. However, the sheath flow design is complicated and requires accurate control of flow rates to work properly. Furthermore, it delivers the sheath flow buffer together with the sample in the fluid channel, which makes the sample inaccessible to any direct measurement of the sample volume.

Flow cytometry is a method for accurately detecting and characterizing cells in biological samples. It is used in CBC testing such as counting and characterizing of leukocyte cells, erythrocyte cells and platelet cells. In conventional flow cytometers, the design of the flow cell also uses the sheath flow design. The flow cell usually uses a fluid channel with a size of several hundred of micrometers in diameter, which is significantly larger than the size of the blood cells (e.g., leukocyte cells 6-15 μm in diameter, erythrocyte cells 6-8 μm in diameter, and platelet cells 1-2 μm in diameter). To confine the sample into a narrower stream (e.g. 20-30 μm in diameter), which is important for accurate measurement of the cells, the flow cell uses the sheath flow, also known as hydrodynamic focusing. By passing an additional sheath flow together with the sample stream through the flow cell, the sheath flow confines the sample stream in the center into a narrowed stream. By adjusting the ratio of the flow rates of the sheath flow and the sample stream, the sample stream can be confined into any desired diameter for measurement. Complex fluidic structures are required to introduce the sheath flow and maintain the consistency of the flow rates. It is also difficult to control the volume of the sample being measured, and thus hard for this design to achieve measurement accuracy of the absolute count, which is the number of target particles per sample volume.

Shi et al. (Four-part leukocyte differential count based on sheathless microflow cytometer and fluorescent dye assay, Lab Chip. 2013 Apr. 7; 13(7):1257-65) discusses a method of using a cytometer flow cell with a sheathless design for the leukocyte differential information. In the sheathless design, the flow cell uses a fluid channel with small diameter and no sheath flow is used. This work teaches a method of measuring the percentages of each leukocyte subtypes (e.g. lymphocyte, monocyte, neutrophil, eosinophil and basophil) in the sample. But it does not teach how to directly measure the absolute count of the leukocyte, which is the number of target leukocyte cells per volume. Instead, it uses an indirect method: pipetting a fixed amount of blood sample to mix with reagents, and then measuring the full amount of this mixture for leukocytes. This method does not work if not the full amount of the mixture is measured. Additional, it does not teach how to measure other CBC parameter (e.g., erythrocyte count, platelet count, hemoglobin concentration, hematocrit, reticulocyte count, nucleated erythrocyte count, erythrocyte indices, and platelet indices).

SUMMARY OF THE DISCLOSURE

The following embodiments and aspects thereof are described and illustrated in conjunction with devices, systems and methods which are meant to be exemplary and illustrative, not limiting in scope.

The present disclosure provides various methods of performing CBC testing. In various embodiments, cartridges with on-board fluidics are used. In some embodiments, the cartridges are disposable. In other embodiments, the cartridges are reusable.

Various embodiments of the present disclosure provide a device for analyzing blood cells in a sample. The device comprises a cartridge device and a reader instrument device. In various embodiments, the cartridge device comprises: a fluidic conduit configured for receiving the sample into the cartridge device; a chamber fluidly connected to the fluidic conduit and configured for mixing at least a portion of the sample with at least of a portion of a reagent to form one or more sample mixtures; and a flow cell fluidly connected to the chamber and configured for forming one or more sample streams from the one or more sample mixtures. In various embodiments, the reader instrument device is configured for receiving the cartridge device, measuring one or a plurality of signals from the sample streams in the flow cell, and analyzing the blood cells in the sample.

Various embodiments of the present disclosure provide a method for analyzing blood cells in a sample. The method comprises: applying the sample to a cartridge device, which is configured for collecting the sample into a fluidic conduit inside the cartridge device; transferring the cartridge device into a reader instrument device; mixing at least a portion of the sample and at least a portion of a reagent to form one or more sample mixtures inside the cartridge device; transferring the one or more sample mixtures into a flow cell inside the cartridge device to form one or more sample streams; using the reader instrument device to measure one or a plurality of signals from the sample streams in the flow cell and analyzing the measured signals, thereby detecting, identifying, characterizing, quantifying, and/or numerating blood cells in the sample.

Various embodiments of the present disclosure provide a method for analyzing blood cells in a sample. The method comprises: applying the sample to a cartridge device, which comprises a flow cell; and transferring the cartridge device into a reader instrument device for analysis, wherein the reader instrument device operates and/or actuates the cartridge device to mix at least a portion of the sample and at least a portion of a reagent comprising size reference beads to form one or more sample mixtures, and to transfer the one or more sample mixtures into the flow cell to form one or more sample streams; wherein the reader instrument device measures one or a plurality of signals from the sample streams in the flow cell; and wherein the reader instrument device analyzes the measured signals to detect, identify, characterize, quantify, and/or numerate blood cells in the sample.

BRIEF DESCRIPTION OF THE DRAWINGS

Exemplary embodiments are illustrated in referenced figures. It is intended that the embodiments and figures disclosed herein are to be considered illustrative rather than restrictive.

FIGS. 3A-3B illustrate, in accordance with various embodiments of the disclosure, non-limiting examples where a plurality of particles flow through a flow cell for detection.

FIGS. 5A-5B illustrate, in accordance with various embodiments of the disclosure, one non-limiting example of a flow sensor as described herein and its symbolic drawing.

FIGS. 5C-5D illustrate, in accordance with various embodiments of the disclosure, another non-limiting example of a flow sensor as described herein and its symbolic drawing.

FIGS. 10A-10B illustrate, in accordance with various embodiments of the disclosure, a diagram of a method as described herein to measure the hemoglobin concentration.

FIGS. 11A-11B illustrate, in accordance with various embodiments of the disclosure, that light absorption can be measured when a sample is moving through a cuvette, or when the sample is stationary in the cuvette.

FIG. 17 illustrates, in accordance with various embodiments of the disclosure, that a cartridge having on-board fluidics can be inserted into a reader instrument for operation.

FIGS. 18A-18B illustrate, in accordance with various embodiments of the disclosure, one non-limiting example of a basic fluidic unit as described herein and its symbolic drawing.

FIGS. 19E-19G illustrate, in accordance with various embodiments of the disclosure, non-limiting examples of active valves.

DETAILED DESCRIPTION OF THE DISCLOSURE

Figure 1A:
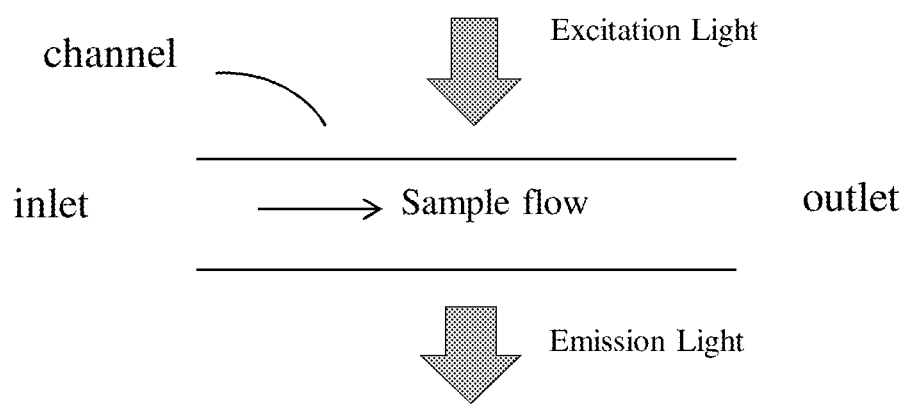
FIGS. 1A-1B illustrate, in accordance with various embodiments of the disclosure, a sample passing through a sheathless flow cell for optical measurement, and a symbolic drawing that represents a sheathless flow cell as described herein.

All references cited herein are incorporated by reference in their entirety as though fully set forth. Unless defined otherwise, technical and scientific terms used herein have the same meaning as commonly understood by one of ordinary skill in the art to which this disclosure belongs. Tabelling, *Introduction to Microfluidics* reprint edition, Oxford University Press (2010); Hguyen et al., *Fundamentals and Applications of Microfluidics* 2$^{nd}$ ed., Artech House Incorporated (2006); Berg et al., *Microfluidics for Medical Applications*, Royal Society of Chemistry (2014); Gomez et al., *Biological Applications of Microfluidics* 1$^{st}$ ed., Wiley-Interscience (2008); and Colin et al., *Microfluidics* 1$^{st}$ ed., Wiley-ISTE (2010), provide one skilled in the art with a general guide to many of the terms used in the present application.

One skilled in the art will recognize many methods and materials similar or equivalent to those described herein, which could be used in the practice of the present disclosure. Other features and advantages of the disclosure will become apparent from the following detailed description, taken in conjunction with the accompanying drawings, which illustrate, by way of example, various features of embodiments of the disclosure. Indeed, the present disclosure is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this disclosure belongs. It should be understood that this disclosure is not limited to the particular methodology, protocols, and reagents, etc., described herein and as such can vary. The definitions and terminology used herein are provided to aid in describing particular embodiments, and are not intended to limit the claims.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

Various embodiments of the present disclosure provide a device for analyzing blood cells in a sample. The device comprises a cartridge device and a reader instrument device. In various embodiments, the cartridge device comprises: a fluidic conduit configured for receiving the sample into the cartridge device; a chamber fluidly connected to the fluidic conduit and configured for mixing at least a portion of the sample with at least of a portion of a reagent to form one or more sample mixtures; and a flow cell fluidly connected to the chamber and configured for forming one or more sample streams from the one or more sample mixtures. In various embodiments, the reader instrument device is configured for receiving the cartridge device, measuring one or a plurality of signals from the sample streams in the flow cell, and analyzing the blood cells in the sample.

In various embodiments, the measured signals comprise an optical signal. In certain embodiments, the optical signal comprises light scattering, light absorption, light extinction, or fluorescence, or a combination thereof. In various embodiments, the optical signal comprises scattered light, reflected light, transmitted light, fluorescence, light absorption, light extinction, or white light image, or a combination thereof.

In various embodiments, the reader instrument device is configured for operating and/or actuating the cartridge device. In various embodiments, the reader instrument device is configured from detecting, identifying, characterizing, quantifying, and/or numerating the blood cells in the sample. In various embodiments, the reader instrument device is configured for detecting, identifying, characterizing, quantifying, and/or numerating leukocyte cells, erythrocyte cells, or platelet cells, or a combination thereof. In various embodiments, the reader instrument device is configured for identifying leukocyte cells into subtypes. In accordance with the present disclosure, the subtypes include but are not limited to lymphocytes, monocytes, neutrophils, eosinophils, and basophils.

In various embodiments, the cartridge device is configured for forming the sample streams in the flow cell without a sheath flow. In various embodiments, the flow cell has a width in the range of about 1-10, 10-40, 40-100, or 100-200 μm; and a depth in the range of about 1-10, 10-40, 40-100, or 100-200 μm. In various embodiments, the flow cell has a length in the range of about 1-10, 10-100, 100-1,000, 1,000-5,000 μm, or 5,000-10,000 μm. In various embodiments, the flow cell comprises a transparent surface for an optical signal from the sample streams in the flow cell; and wherein the reader instrument device is configured for measuring the optical signal. In certain embodiments, the optical signal comprises light scattering, light absorption, light extinction, or fluorescence, or a combination thereof. In various embodiments, the optical signal comprises scattered light, reflected light, transmitted light, fluorescence, light absorption, light extinction, or white light image, or a combination thereof. In various embodiments, the transparent surface comprises cyclic olefin copolymer, cyclo-olefin polymer, poly-methyl methacrylate, polycarbonate, polystyrene, or poly-chloro-tri-fluoro-ethylene, or a combination thereof.

In various embodiments, the chamber has a volume in the range of about 0.01-0.1 ml, 0.1-0.2 ml, 0.2-0.4 ml, 0.4-0.8 ml, 0.8-2 ml, or 2-10 ml. In some embodiments, the cartridge device comprises only one chamber. In other embodiments, the cartridge device comprises a plurality of chambers.

In various embodiments, the chamber comprises a venting port configured for receiving a pneumatic pressure source. In various embodiments, the pneumatic pressure source has an adjustable pressure. In various embodiments, the pneumatic pressure source has a pressure higher than the atmosphere pressure, lower than the atmosphere pressure, or equal to the atmosphere pressure.

In various embodiments, when the cartridge device is in use, the chamber is so positioned that at least a portion of the fluid inside the chamber is pulled by gravity away from the venting port and/or towards the lower bottom of the chamber. In various embodiments, when the cartridge device is in use, the chamber is so positioned that at least a portion of the fluid inside the chamber is pulled by gravity away from the venting port and/or towards where the fluid enters or exits the chamber. In various embodiments, when the cartridge device is in use, the chamber's volume is larger than the volume of the fluid accommodated therein, and an air gap exists between the venting port and the fluid accommodated therein.

In various embodiments, the cartridge device further comprises a cuvette; and the reader instrument device is configured for measuring a signal from the sample mixtures in the cuvette to determine the hemoglobin concentration in the sample. In some embodiments, the reader instrument device is configured for measuring a light absorption signal from the sample mixtures in the cuvette to determine the hemoglobin concentration in the sample. In various embodiments, the reader instrument device is configured for measuring at least two light absorption signals from the sample mixtures in the cuvette to determine the hemoglobin concentration in the sample: one light absorption signal in the wavelength band of about 520-540 nm, 540-560 nm, or 560-580 nm, and another light absorption signal in the wavelength band of about 700-800 nm, 800-850 nm, or above 850 nm. In some embodiments, the cuvette has a light path length in the range of about 0.1-1, 1-2, 2-5 or 5-10 mm for the light absorption signal.

In various embodiments, the reader instrument device is configured to have no exchange of samples, reagents or sample mixtures with the cartridge device. In various embodiments, the reader instrument device is configured to have no contact with samples, reagents or sample mixtures in the cartridge device.

In various embodiments, a cartridge device as disclosed herein further comprises a reagent. In some embodiments, the reagent comprises one reagent. In other embodiments, the reagent comprises two separate reagents.

In various embodiments, the reagent comprises an osmolality-adjusting compound for forming sample mixtures with an osmolality in the range of about 140-160, 160-180, 180-200, 200-220, 220-240, 240-260, 260-280, 280-300, 300-320, 320-340, 340-360, 360-380, or 380-400 mOsm/L. In certain embodiments, the reagent comprises an osmolality-adjusting compound for forming sample mixtures with an osmolality in the range of about 140-160, 160-180, 180-200, 200-220, 220-240, 240-260, 260-280, 280-300, 300-320, 320-340, 340-360, 360-380, or 380-400 mOsm/L; and wherein the reader instrument is configured for detecting, identifying, characterizing, quantifying, and/or numerating erythrocyte cells and/or platelet cells in the sample mixtures.

In various embodiments, the reagent comprises a sphering compound for transforming erythrocyte cells from disk shape into sphere shape.

In various embodiments, the reagent comprises a fluorescent labeling reagent for labeling nucleic acids in blood cells in the sample mixtures; and wherein the reader instrument device is configured for measuring a fluorescence signal from the sample streams in the flow cell. In some embodiments, the labeling reagent comprises a fluorescent dye.

In various embodiments, the reagent comprises a lysing compound for lysing erythrocyte cells in the sample mixtures to release hemoglobin.

In various embodiments, the reagent comprises size reference beads; and wherein the reader instrument is configured for measuring a reference signal from the size reference beads in the flow cell for analyzing the size of blood cells. In accordance with the present disclosure, size reference beads are beads that have uniform and known sizes. In various embodiments, size reference beads are fluorescent beads. In various embodiments, size reference beads have fluorescent intensities different from the blood cells in the sample streams and hence can be distinguished from the blood cells on fluorescent intensities. In various embodiments, the reader instrument device analyzes the intensity of the optical signal to identify the size reference beads from the blood cells in the sample streams. In various embodiments, the size reference beads are fluorescent beads; and the reader instrument device is configured for measuring a fluorescence signal to identify the size reference beads from the blood cells in the sample streams.

In various embodiments, the size reference beads have a diameter in the range of about 0.1-1, 1-2, 2-6, 6-8, 8-10, 10-15, 25-30, 30-50, or 50-100 μm. In some embodiments, the size reference beads have a diameter of 10 μm. In other embodiments, the size reference beads have a diameter of 5 μm. In some embodiments, the reagent can comprise size reference beads of one size. In other embodiments, the reagent can comprise size reference beads of multiple sizes.

In various embodiments, size reference beads of different sizes have different fluorescent intensities (e.g., labelled with different amounts of fluorescent dyes) and hence can be separately identified based on fluorescent intensities.

In various embodiments, a cartridge device as disclosed herein further comprises a flow sensor fluidly connected to the flow cell; and the reader instrument device is configured for measuring a sensing signal from the flow sensor when the sample streams enter the flow sensor. In various embodiments, the reader instrument device is configured for using the sensing signal from the flow sensor to determine the absolute count of the blood cells in the sample. In various embodiments, the blood cells are leukocyte cells, and/or erythrocyte cells, and/or platelets cells. In various embodiments, the fluidic connection between the flow cell and the flow sensor is configured for a sample stream to have the same flow rate flowing through the flow cell and the flow sensor.

In various embodiments, the flow sensor comprises a transparent surface for an optical signal from the sample streams in the flow sensor; and wherein the reader instrument device is configured for measuring the optical signal. In various embodiments, the measured sensing signal comprises an optical signal. In certain embodiments, the optical signal comprises light scattering, light absorption, light extinction, or fluorescence, or a combination thereof. In various embodiments, the optical signal comprises scattered light, reflected light, transmitted light, fluorescence, light absorption, light extinction, or white light image, or a combination thereof. In various embodiments, the transparent surface comprises cyclic olefin copolymer, cyclo-olefin polymer, poly-methyl methacrylate, polycarbonate, polystyrene, or poly-chloro-tri-fluoro-ethylene, or a combination thereof.

In various embodiments, the flow sensor comprises a fluidic channel and a sensing zone on the fluidic channel; the fluidic channel is fluidly connected to the flow cell to allow the sample streams to flow through; and the reader instrument device is configured for measuring a sensing signal from the sensing zone when the sample streams enter the sensing zone. In various embodiments, the fluidic channel has a channel width in the range of about 0.001-0.05 mm, 0.05-1 mm, or 1-5 mm. In various embodiments, the fluidic channel has a channel depth in the range of about 0.001-0.01 mm, 0.01-0.5 mm, 0.5-1 mm, or 1-2 mm.

In various embodiments, a cartridge device as disclosed herein further comprises a microfluidic channel fluidly connected to the chamber and a valve on the microfluidic channel, and the microfluidic channel has a cross section in the range of about 0.001-0.01 mm$^2$, 0.01-0.1 mm$^2$, 0.1-0.25 mm$^2$, 0.25-0.5 mm$^2$, 0.5-1 mm$^2$, 1-2 mm$^2$, or 2-10 mm$^2$. In various embodiments, the valve is a passive valve that is configured for allowing a fluid flow to pass through the microfluidic channel when a pneumatic pressure is applied to the fluid flow and stopping the fluid flow when no pneumatic pressure is applied to the fluid flow. In some embodiments, the valve is a passive valve that comprises one of the following structures: (i) a patch of hydrophobic surface in a channel having a hydrophilic surface, (ii) a patch of hydrophilic surface in a channel having a hydrophobic surface, (iii) an enlargement of the channel cross section along the flow direction in a channel having a hydrophilic surface, and (iv) a contraction of the channel cross section along the flow direction in a channel having a hydrophobic surface.

In various embodiments, the reader instrument device is configured for applying an actuation mechanism to control the fluid transfer in the cartridge device, and the actuation mechanism comprises a pneumatic pressure source. In various embodiments, the applied pneumatic pressure source actuates the cartridge device to transfer the sample mixtures from the chamber into the flow cell to form the sample streams.

In various embodiments, the cartridge device is configured for mixing two separate portions of the sample received in the fluidic conduit with the reagent to form two separate sample mixtures. In some embodiments, the reagent comprises one reagent. In other embodiments, the reagent comprises two separate reagents. In various embodiments, the cartridge device is configured for mixing a portion of the sample received in the fluidic conduit with a first reagent to form a first sample mixture, and another portion of the sample received in the fluidic conduit with a second reagent to form a second sample mixture. In various embodiments, the cartridge device is configured for forming the two separate sample mixtures in the same chamber separately. In various embodiments, the cartridge device is configured for separately transferring the two separate sample mixtures into the same chamber without mixing the two separate sample mixtures. In some embodiments, any sample mixture already in the chamber is transferred out before another sample mixture is transferred into the chamber. In some embodiments, the cartridge device is configured for accommodating one sample mixture at one time.

In various embodiments, the reader instrument device is configured for operating and/or actuating the cartridge device to form two separate sample streams in the same flow cell from the two separate sample mixtures. In various embodiments, the reader instrument is configured for numerating leukocyte cells in one of the two sample mixtures and erythrocyte cell and/or platelet cells in the other of the two sample mixtures.

In various embodiments, the cartridge device comprises an inlet port fluidly connected to the fluid conduit; and the inlet port comprises a valve or an external structure to close or seal the inlet port after the sample is received into the fluid conduit. In various embodiments, the fluid conduit has a fixed orientation and/or a fixed position in the cartridge device. In some embodiments, the fluid conduit does not move in the cartridge device. In some embodiments, the fluid conduit does not rotate in the cartridge device. In various embodiments, the cartridge device is configured for transferring at least a portion of the reagent into the fluidic conduit to flush at least a portion of the received sample into the chamber to form a sample mixture. In certain embodiments, the fluid conduit is configured for receiving a pre-determine sample volume in the range of about 0.1-1 μL, 1-5 μL, 5-10 μL, 10-20 μL, or 20-50 μL.

Various embodiments of the present disclosure provide a method for analyzing blood cells in a sample. The method comprises: applying the sample to a cartridge device, which is configured for collecting the sample into a fluidic conduit inside the cartridge device; transferring the cartridge device into a reader instrument device; mixing at least a portion of the sample and at least a portion of a reagent to form one or more sample mixtures inside the cartridge device; transferring the one or more sample mixtures into a flow cell inside the cartridge device to form one or more sample streams; using the reader instrument device to measure one or a plurality of signals from the sample streams in the flow cell and analyzing the measured signals, thereby detecting, identifying, characterizing, quantifying, and/or numerating blood cells in the sample.

Various embodiments of the present disclosure provide a method for analyzing blood cells in a sample. The method comprises: applying the sample to a cartridge device, which comprises a flow cell; and transferring the cartridge device into a reader instrument device for analysis, wherein the reader instrument device operates and/or actuates the cartridge device to mix at least a portion of the sample and at least a portion of a reagent comprising size reference beads to form one or more sample mixtures, and to transfer the one or more sample mixtures into the flow cell to form one or more sample streams; wherein the reader instrument device measures one or a plurality of signals from the sample streams in the flow cell; and wherein the reader instrument device analyzes the measured signals to detect, identify, characterize, quantify, and/or numerate blood cells in the sample.

In various embodiments, the measured signals comprise an optical signal. In certain embodiments, the optical signal comprises light scattering, light absorption, light extinction, or fluorescence, or a combination thereof. In various embodiments, the optical signal comprises scattered light, reflected light, transmitted light, fluorescence, light absorption, light extinction, or white light image, or a combination thereof.

In accordance with the present disclosure, size reference beads are beads that have uniform and known sizes. In various embodiments, size reference beads are fluorescent beads. In various embodiments, size reference beads have fluorescent intensities different from the blood cells in the sample streams and hence can be distinguished from the blood cells on fluorescent intensities. In various embodiments, the reader instrument device analyzes the intensity of the optical signal to identify the size reference beads from the blood cells in the sample streams. In various embodiments, the size reference beads are fluorescent beads; and the reader instrument device is configured for measuring a fluorescence signal to identify the size reference beads from the blood cells in the sample streams.

In various embodiments, the size reference beads have a diameter in the range of about 0.1-1, 1-2, 2-6, 6-8, 8-10, 10-15, 25-30, 30-50, or 50-100 µm. In some embodiments, the size reference beads have a diameter of 10 µm. In other embodiments, the size reference beads have a diameter of 5 µm. In some embodiments, the reagent can comprise size reference beads of one size. In other embodiments, the reagent can comprise size reference beads of multiple sizes. In various embodiments, size reference beads of different sizes have different fluorescent intensities (e.g., labelled with different amounts of fluorescent dyes) and hence can be separately identified based on fluorescent intensities.

In various embodiments, the reader instrument measures a reference signal from the size reference beads in the flow cell for analyzing the size of blood cells. In various embodiments, the measured reference signal comprises an optical signal. In certain embodiments, the optical signal comprises light scattering, light absorption, light extinction, or fluorescence, or a combination thereof. In various embodiments, the optical signal comprises light scattering, light absorption, light extinction, or fluorescence, or a combination thereof.

In various embodiments, the reagent comprises an osmolality-adjusting compound for forming sample mixtures with an osmolality in the range of about 140-160, 160-180, 180-200, 200-220, 220-240, 240-260, 260-280, 280-300, 300-320, 320-340, 340-360, 360-380, or 380-400 mOsm/L.

In various embodiments, the reagent comprises a sphering compound for transforming erythrocyte cells from disk shape into sphere shape.

In various embodiments, the sample streams are formed in the flow cell without a sheath flow and have a width in the range of about 1-10, 10-40, 40-100, or 100-200 µm; and a depth in the range of about 1-10, 10-40, 40-100, or 100-200 µm.

Figure 1B:
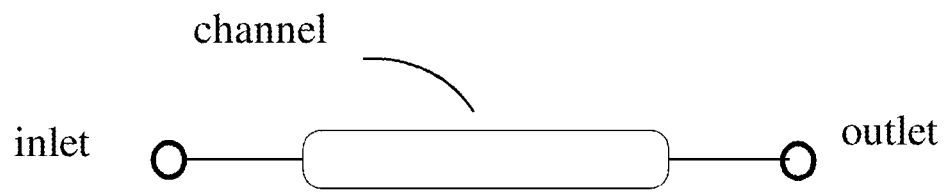

It various embodiments of this disclosure, a sheathless flow cell is used instead of the conventional design with a sheath flow. This sheathless flow cell has a fluidic channel having a core diameter chosen according to the target sample stream diameter. For one example, a fluidic channel of 30 µm in diameter can be used to achieve a target sample stream of 30 µm in diameter. For another example, a fluidic channel of 50 µm in diameter can be used to achieve a target sample stream of 50 µm in diameter. In this design, the sample stream is confined into the desired diameter while the use of sheath flow is eliminated. In some embodiments, the channel of the flow cell can be transparent to certain light wavelengths (e.g., excitation light and emission light), so that optical signals can be measured from samples in the flow cell. As shown in FIG. 1A, a sample can pass through the sheathless flow cell for optical measurement. A light beam from a light source (e.g., excitation light) can be used to illuminate a designated sensing area of the flow cell. Correspondently, signals of the light beam through the sample (e.g., emission light) are being detected. Non-limiting examples of the detected signals include fluorescence, light scattering, light absorption, and light distinction, etc. In some embodiments, the sheathless flow may also be used to detect other signal such as electrical impedance, cell morphology imaging, etc. FIG. 1B illustrates a symbolic drawing that represents a unit of the sheathless flow cell as described herein.

Figure 2B:
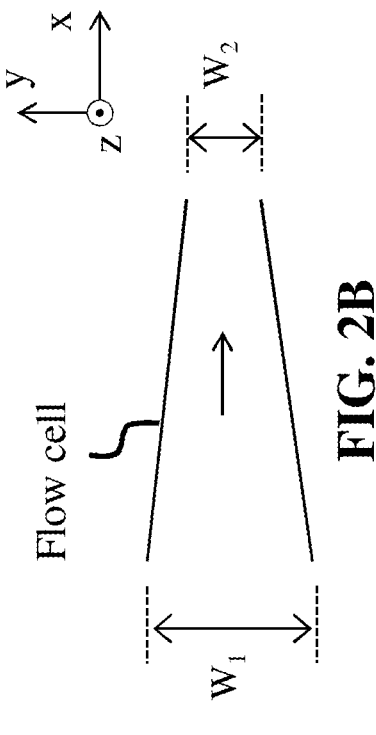
FIGS. 2A-2D illustrate, in accordance with various embodiments of the disclosure, the top view (in x-y plane) of non-limiting examples of a flow cell as described herein.
Figure 2D:
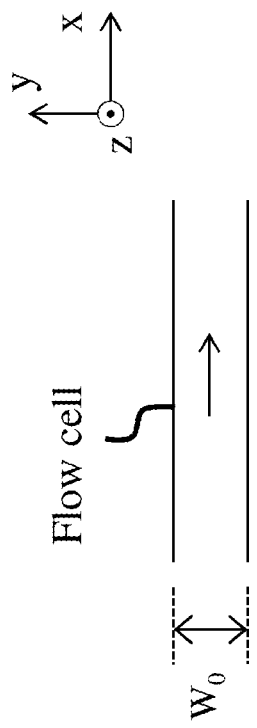
Figure 2A:
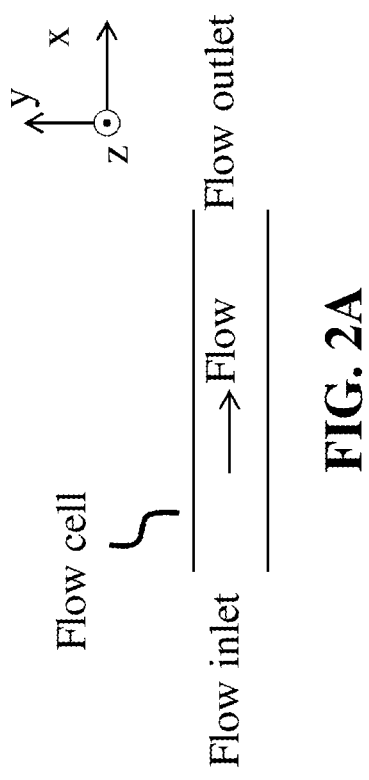
Figure 2C:
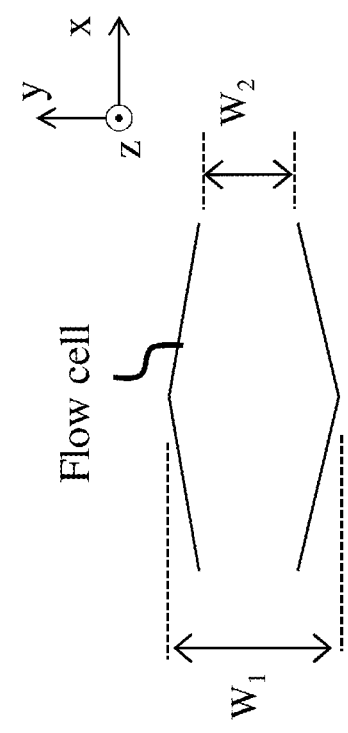

The sheathless flow cell can be a fluidic channel that has various geometry shapes. FIGS. 2A-2D shows the top view (in x-y plane) of a few examples of the flow cell. The top view (x-y plane), as shown in FIG. 2A, is defined as the plane perpendicular to the direction of the excitation light (z-axis). The length is defined as the channel dimension along the sample flow (x-axis), and the width is defined as the dimension along the y-axis. The depth is defined as the channel dimension along the z-axis. FIG. 2B shows an example of the flow cell that has a gradually decreased width, where the maximum width is $W_1$ and the minimum width is $W_2$. In other embodiments, the flow cell can have a gradually increased width. FIG. 2C shows an example of the flow cell that has a non-gradually changing width, where the maximum width is $W_1$ and the minimum width is $W_2$. FIG. 2D shows an example of the flow cell that has a fixed width ($W_1=W_2=W_0$) at various positions along channel length.

In some embodiments, the difference of the maximum width $W_1$ and the minimum width $W_2$ are within a designated difference. A non-limiting example of the range of the width difference is $(W_1-W_2)/W_2 \leq 20\%$. The ranges of the channel width and the depth are chosen to be large enough so that target particles (e.g., cells in biological samples) can pass through the flow cell without blocking it. Meanwhile, they are chosen to be small enough to minimize the coincidence error in the flow cytometer analysis. The minimum width $W_2$ can be in the range of 1-10, 10-40, 40-100, or 100-200 µm. The depth of the channel can be in the range of 1-10, 10-40, 40-100, or 100-200 µm. The length of the channel can be in the range of 1-10, 10-40, 40-100, 100-200, 200-300, 300-400, 400-500, 500-600, 600-700, 700-800, 800-900, 900-1000, 1000-5000, or 5000-10000 µm. The cross section of the channel (in y-z plane) can have the shape of a rectangular, a trapezoid, a circle, or a half circle, or any other shapes.

When the sheathless flow cell is used for optical measurement, at least one surface of the channel is transparent to the light wavelength involved in the measurement. The material for forming the channel surface can be any transparent material such as glass, quartz, or plastics including but not limited to Cyclic Olefin Copolymer (COC), Cyclo-olefin Polymer (COP), Poly-Methyl methacrylate (PMMA), polycarbonate (PC), Polystyrene (PS), or Poly-chloro-tri-fluoro-ethylene (PCTFE) materials such as Aclar, etc.

The fluid sample for analysis in the flow cell can be a fluid suspension of a plurality of particles. For one example, the fluid sample can be a blood sample containing different cells (e.g., leukocyte cells, erythrocyte cells, and platelet cells, and their combinations). For another example, the fluid sample can be a blood sample in which certain types of cells remain intact (e.g., leukocyte cells) while other types of cells have been lysed (e.g., erythrocyte cells). For another example, the fluid sample can be a blood sample in which certain types of cells (e.g., leukocyte cells) have been labeled with fluorophore. For still another example, the fluid sample can be a mixture of blood cells and other particles such as non-fluorescent beads or fluorescent beads. For other examples, the fluid samples can also be other biological samples such as cerebrospinal fluid, urine, saliva, semen, etc.

When particles flow through the sheathless flow cell, various signals can be measured to detect and characterize the particles. The measurable signals include but are not limited to optical signals such as fluorescence, light scattering (small angel forward scattering, large angel forward scattering, side scattering, etc.), light absorption, and light extinction, etc. FIG. 3A shows an example where a plurality of particles flow through the flow cell for detection. All particles in the sample flow through in a one-by-one manner. Under the illumination of the excitation light (EL), each cell can be characterized for optical signals including but not limited to fluorescence (FL) and light scattering (LS). FIG. 3B shows another example where a plurality of particles flowing through the flow cell for detection. Some particles are flowing through while overlapping with each other. Nevertheless, if only considering the target particles, they are flowing through still in a one-by-one manner without overlapping with other target particles. In this way, the fluorescence signals can still be measured to detect these target particles one by one, by labeling the target particles with fluorophore to distinguish from the other particles beforehand. The other particles can be non-fluorescent or treated with different fluorophore distinguishable from the target particles.

Figure 4A:
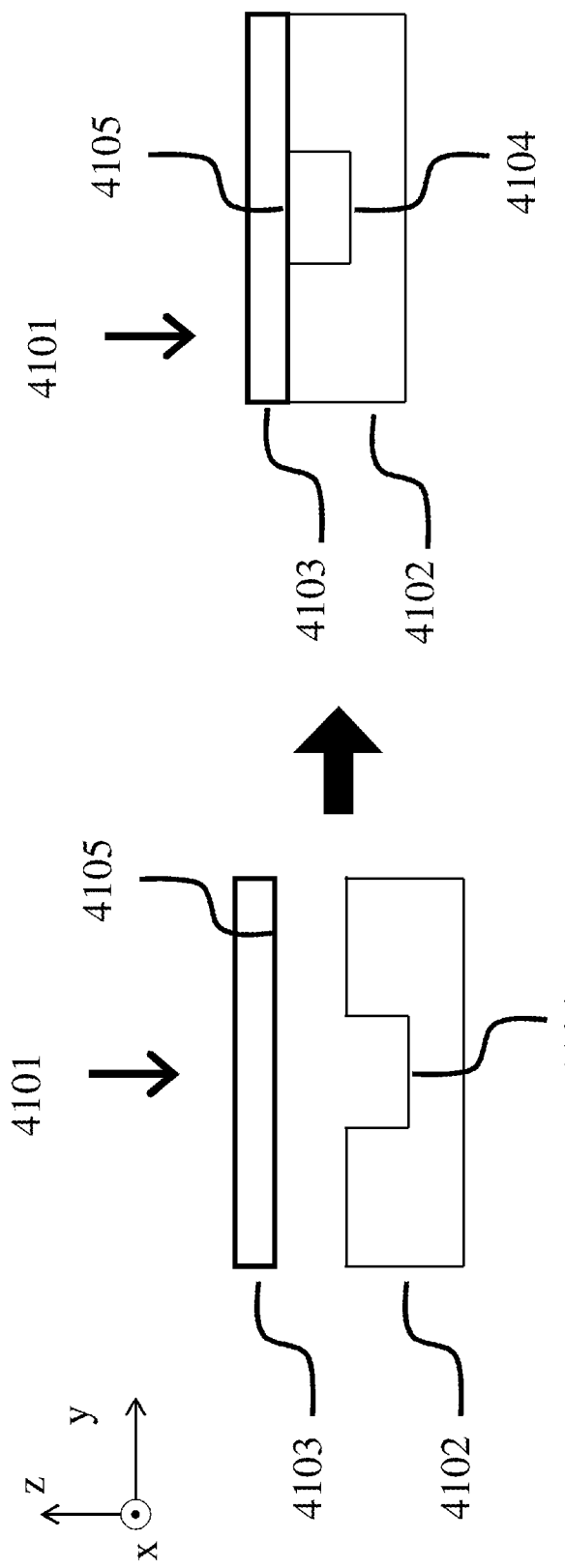
FIGS. 4A-4B illustrate, in accordance with various embodiments of the disclosure, non-limiting examples of building a sheathless flow cell as described herein.
Figure 4B:
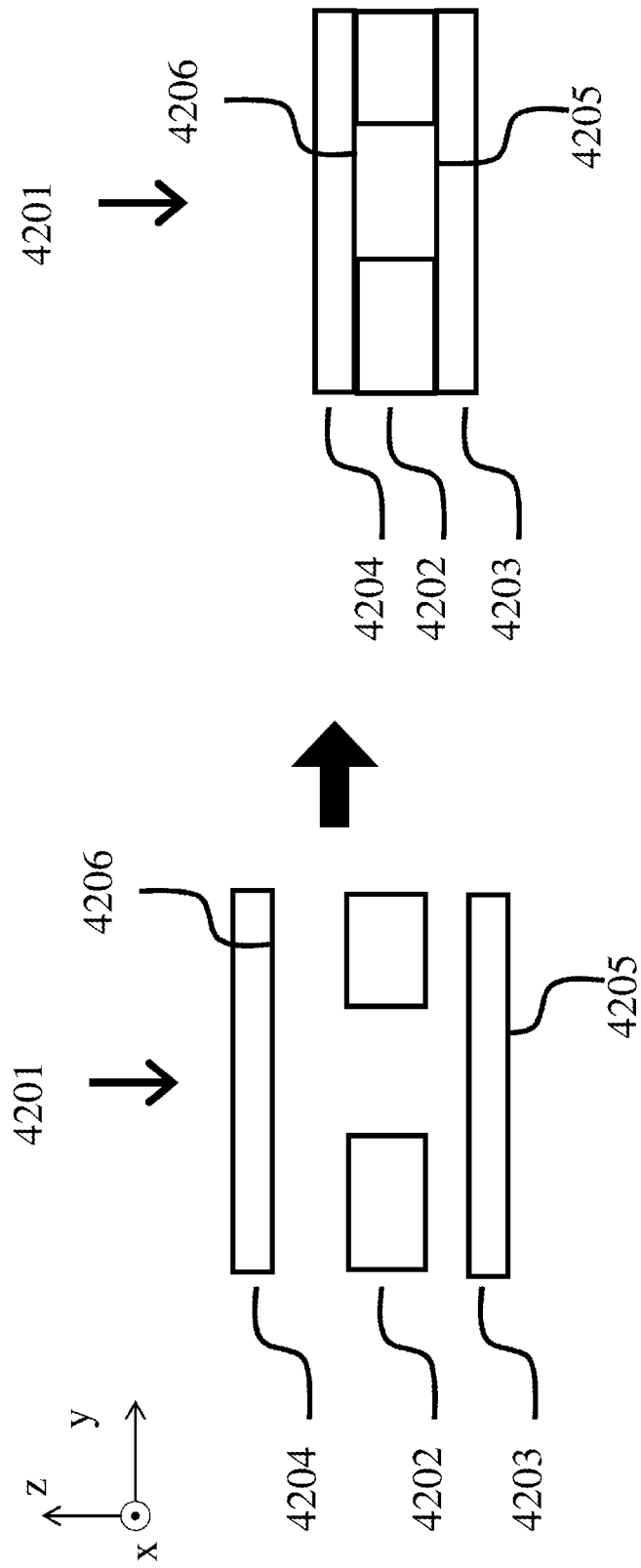

The sheathless flow cell can be built with various manufacturing processes. An open fluidic channel can be built with various manufacturing processes, such as injection molding, embossing, etching, CNC, laser cutting, and die cutting, etc. A cover can then be added on top of the open fluidic channel to form the enclosed fluidic channel as the flow cell. The cover can be added by various manufacturing processes, such as thermal fusion bonding, thermal lamination, adhesive bonding, solvent assisted bonding, laser wielding, and ultrasonic wielding, etc. When optical signals are detected from particles flowing inside the sheathless flow cell, smooth surface of the flow cell is useful to achieve high quality optical signals in measurements. Non-limiting examples of building the sheathless flow cell are illustrated here. FIG. 4A shows one example of building the sheathless flow cell 4101 having two pieces. The cross-section view (y-z plane) is perpendicular to the direction of sample flow (x-axis). The bottom piece 4102 forms three sides of a channel without a cover. The top piece 4103 adds a cover side to the channel, which then forms an enclosed channel. The bottom and the top surfaces 4104 and 4105 can achieve smoothness for optical measurement in the two pieces 4102 and 4103, respectively. FIG. 4B shows another example of building the sheathless flow cell 4201 having three pieces. The middle piece 4202 forms two sides of a channel, without top and bottom sides. Then a bottom piece 4203 and a top piece 4204 are added separately. The three pieces together forms an enclosed channel as the flow cell. The surface 4205 and 4206 can achieve smoothness for optical measurement in the two pieces 4203 and 4204, respectively.

The sheathless flow cell can detect and numerate the particles in a fluid sample. However, in order to obtain the absolute count, which is the number of particles per sample volume, further information of the sample volume is needed. A flow sensor for measuring the sample volume can be used together with the sheathless flow cell to determine the sample volume and hence the absolute count.

Described herein are non-limiting examples of such a flow sensor. In one non-limiting example, the flower sensor has one or a plurality of sensing zones on a channel to detect the existence of liquid in the channel and/or measure the fluid displacement volume, the volume of a fluidic plug, flow rate or flow velocity, etc. More information regarding the design, operation and manufacturing of the flow sensor can be found in U.S. application Ser. No. 15/209,226 and PCT Application PCT/US16/42089, which are incorporated herein by reference in their entirety as if fully set forth. FIG. 5A illustrates one non-limiting example of the flow sensor, which has two sensing zones along the length of a fluidic channel. The sensor detects whether there is fluid inside the channel overlapping with the sensing zones. The volume of fluid filling up the channel between the two sensing zones is determined by the known geometry of the channel. FIG. 5B is a symbolic drawing to represent this design. FIG. 5C illustrates another non-limiting example of the flow sensor, which has only one sensing zone on the channel. FIG. 5D is a symbolic drawing to represent this design.

As described herein, the sheathless flow cell and the flow sensor are used together in a way to achieve in situ measurement of the sample volume during the cytometer analysis. Using various configurations as described herein, the particles in a fluid sample can be detected, characterized, numerated and the absolute count of the particles can be obtained.

Figure 6A:
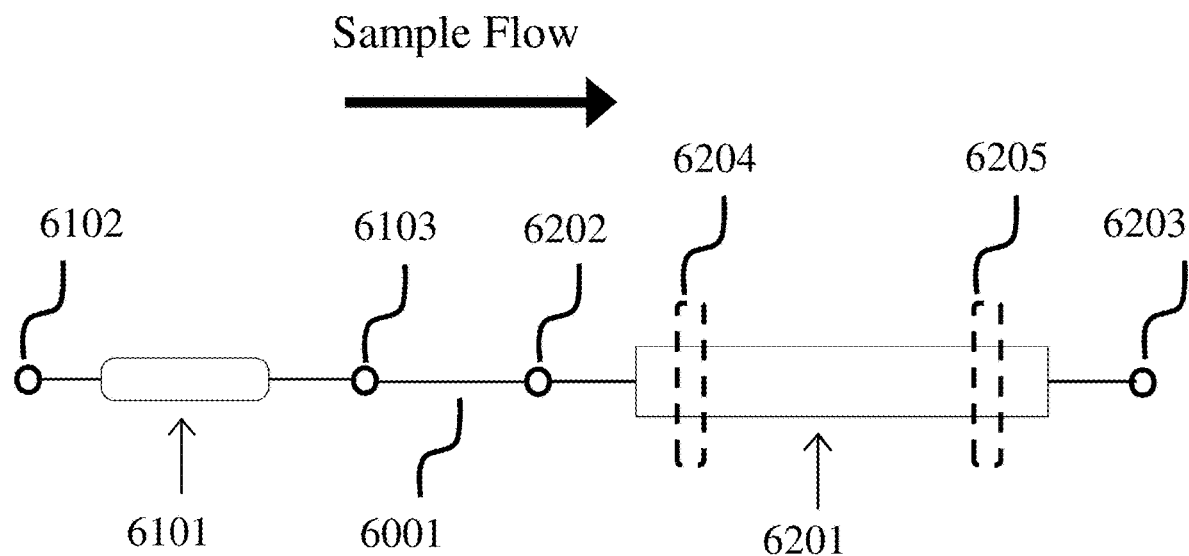
FIGS. 6A-8B illustrate, in accordance with various embodiments of the disclosure, various exemplary configurations, in which the particles in a fluid sample can be detected, characterized, numerated and the absolute count of the particles can be obtained.
Figure 6B:
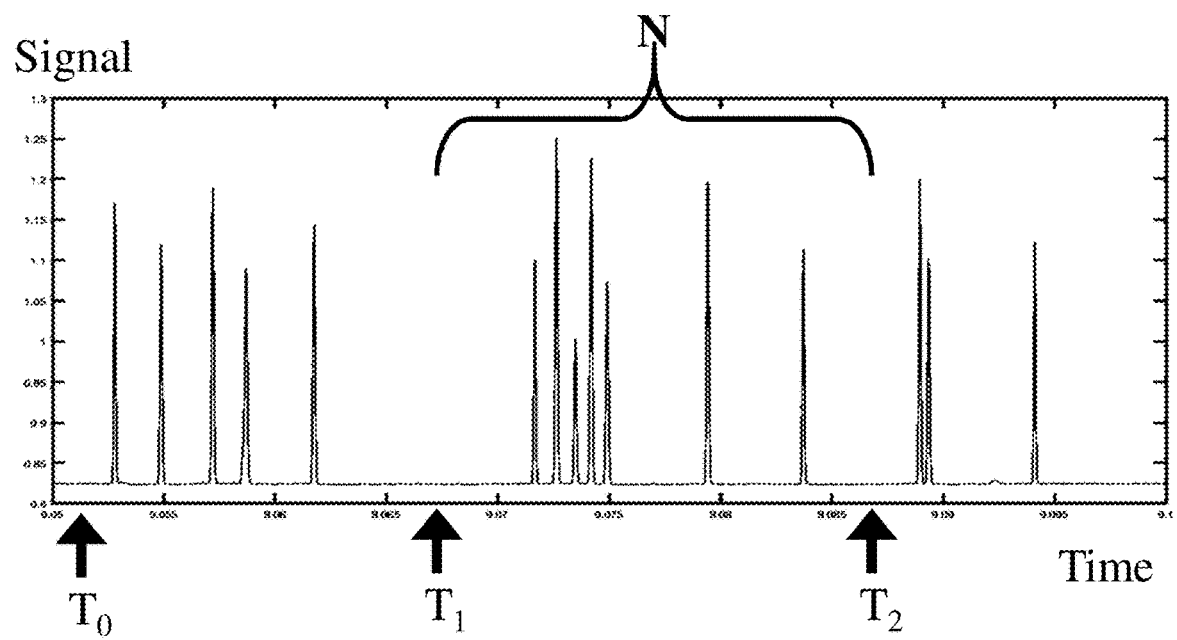

FIG. 6A shows one exemplary configuration, where the outlet 6103 of the flow cell 6101 is coupled to the inlet 6202 of the flow sensor 6201 by a fluidic conduit 6001. In other examples, the outlet of the flow cell can be directly coupled to the inlet of the flow sensor without the additional fluidic conduit. The flow sensor has two sensing zones 6204 and 6205. A fluid sample flows into the inlet 6102 of the flow cell and then out of the outlet 6203 of the flow sensor. Meanwhile, signals (e.g., optical signals and electrical impedances) are measured from the sample passing through the flow cell. The measured signal is recorded as shown in the example of FIG. 6B, where the y-axis is the signal intensity and the x-axis is the time. Signal peaks in the plot indicate particles being detected in the flow cell, and the number of recorded signal peaks is used to determine the number of particles being detected. $T_0$ is when the sample starts to being detected in the flow cell, $T_1$ is when the fluid sample reaches the first sensing zone 6204, and $T_2$ is when the fluid sample passes the second sensing zone 6205. From time $T_1$ to $T_2$, the total number of target particles detected in the flow cell is N. The fluid volume $V_0$ between the two sensing zones is a known parameter from the design of the flow sensor. Because the flow cell has a sheathless design, the volume of fluid flows through the flow cell is only the fluid sample. Therefore, the sample volume being measured in the flow cell between $T_1$ and $T_2$ equals to $V_0$. In this design, the absolute count is determined as:

$$\text{Absolute Count 1} = N/V_0 \qquad [1]$$

Figure 7A:
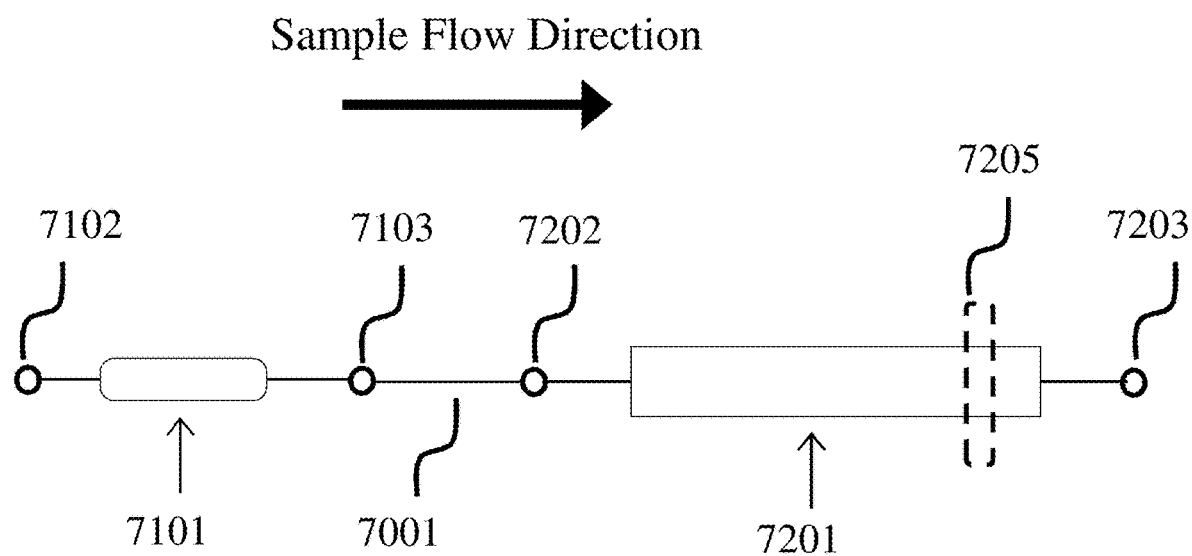
Figure 7B:
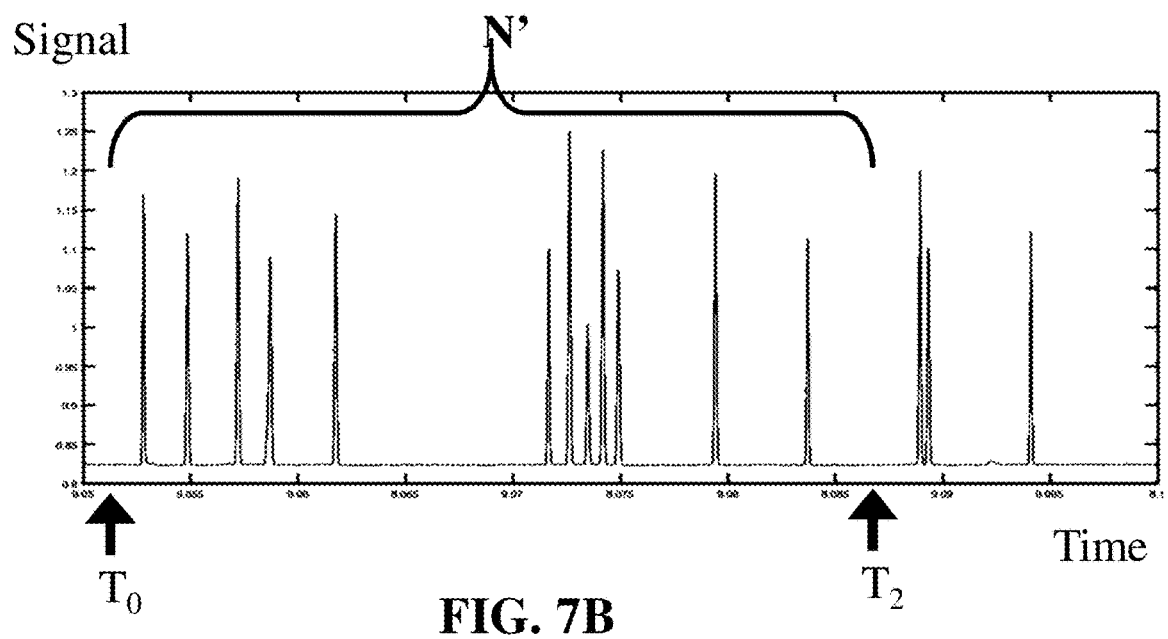

FIG. 7A shows another exemplary configuration, where the outlet 7103 of the flow cell 7101 is coupled to the inlet 7202 of the flow sensor 7201 by a fluidic conduit 7001. In other examples, the outlet of the flow cell can be directly coupled to the inlet of the flow sensor without the additional fluidic conduit. The flow sensor has one sensing zone 7205. A fluid sample flows into the inlet 7102 of the flow cell and then out of the outlet 7203 of the flow sensor. The signal measured in the flow cell is recorded, as illustrated in FIG. 7B. $T_0$ is when the sample starts to being detected in the flow cell, and $T_2$ is when the fluid sample reaches the sensing zone 7205. From time $T_0$ to $T_2$, the total number of target particles detected in the flow cell is N'. The volume $V_0'$ is the total fluid volume needed to fill up the fluidic conduit from the flow cell to the sensing zone 7205, which is a known design parameter. In this design, the absolute count is determined as:

$$\text{Absolute Count 2} = N'/V_0' \qquad [2]$$

Figure 8A:
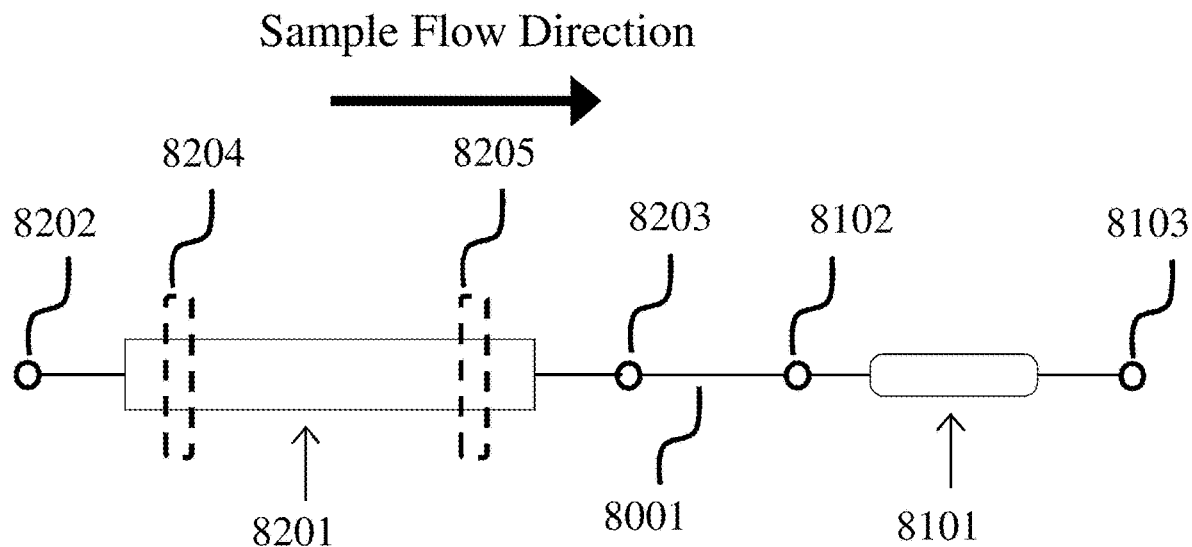
Figure 8B:
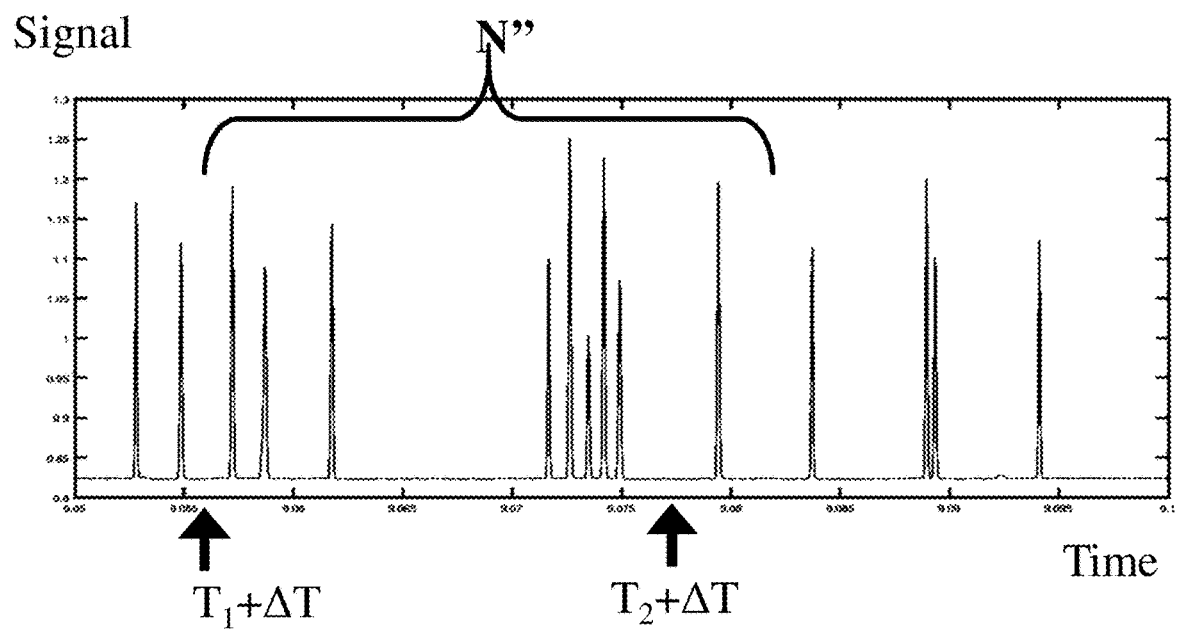

FIG. 8A shows another exemplary configuration, where the inlet 8102 of the flow cell 8101 is coupled to the outlet 8203 of the flow sensor 8201 by a fluidic conduit 8001. In other examples, the inlet of the flow cell can be directly coupled to the outlet of the flow sensor without the additional fluidic conduit. The flow sensor has two sensing zones 8204 and 8205. A fluid sample flows into the inlet 8102 of the flow sensor and then out of the outlet 8203 of the flow sensor. The signal measured in the flow cell is recorded, as illustrated in FIG. 8B. $T_1$ is when the fluid sample reaches the sensing zone 8204, and $T_2$ is when the fluid sample reaches the sensing zone 8205. In this example, the number of cells counted N" is determined by the signal peaks between time points $T_1+\Delta T$ and $T_2+\Delta T$, as shown in FIG. 8B, where $\Delta T$ can be any empirical value to compensate the time delay between sample's reaching the first sensing zone 8204 and sample's reaching the flow cell 8101. The fluid volume $V_0$ between the two sensing zones is a known parameter from the design of the flow sensor. In this design, the absolute count is determined as:

$$\text{Absolute Count 3} = N''/V_0 \qquad [3]$$

The combination of the flow cell and the flow sensor can be used for measurement of particles (e.g., cells) of various sizes. For examples, the size of the target particles can be in the range of 0.1-1, 1-10, 10-15, 15-30, 30-50, or 50-100 µm depending on the size of the flow cell. To minimize the risk of clogging the sheathless channel, the size of the particles being measured should be smaller than size of the flow cell, and the size difference can range from 1-5, 5-10, 10-20, or 20-50 µm. To minimize the coincidence error for the cytometer analysis, the concentration of the target particles in the fluid sample can be in the range of 1-100, 100-1,000, 1,000-5,000, 5,000-20,000, or 20,000-100,000 particles per µl sample.

When the target particles are biological cells, too fast a flow velocity in the sheathless flow cell can introduce shear force and may lyse the cells. Because the sheathless flow cell has a dimension similar to the target particles, this imposes a limitation on the flow rate of the sample. The flow rate can be in the range of 0.001-1, 1-50, 50-200, or 200-1000 µl per minute (µl/min). For size consideration when implementing in self-contained cartridges, the range of the fluid sample volume can be constrained by the cartridge size. The volume of the flow sensor and the total volume of the sample can be in the range of 0.1-1 µl, 1-200 µl, 200-1000 µl, 1-5 ml, or 5-30 ml. In certain embodiments, by considering both the sample volume and the flow rate, the measurement is completed in less than 1 minute, 5 minutes, 10 minutes, or 30 minutes.

Figure 9A:
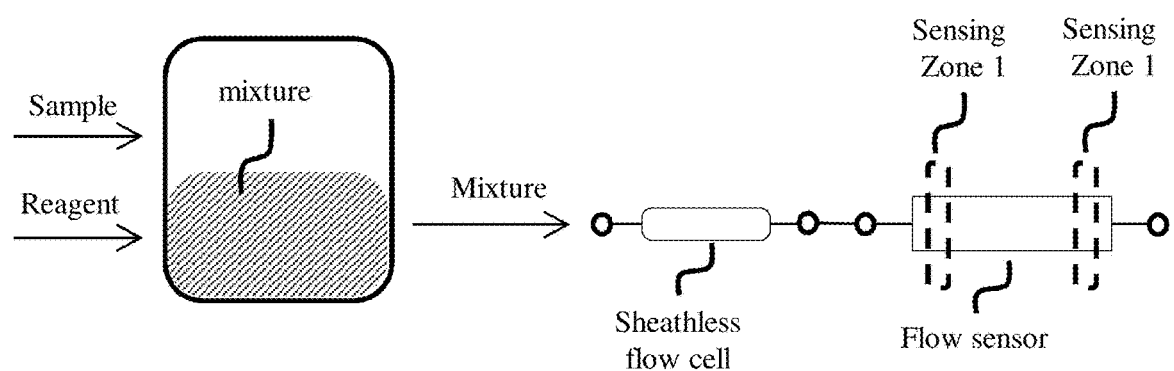
FIGS. 9A-9E illustrate, in accordance with various embodiments of the disclosure, one non-limiting example for the measurement of blood cells in a fluidic configuration that has a sheathless flow cell and a flow sensor with two sensing zones.

Blood samples can be measured in a fluidic configuration having the sheathless flow cell and the flow sensor for CBC parameters that include but are not limited to leukocyte count, erythrocyte count and platelet count. leukocyte count, erythrocyte count and platelet count are the absolute counts of the leukocyte cells, erythrocyte cells and platelet cells in a sample, respectively. As shown in FIG. 9A, one non-limiting example shows the measurement of blood cells in a fluidic configuration that has a sheathless flow cell and a flow sensor with two sensing zones. A blood sample and a sample treatment reagent are mixed into a sample mixture. In some embodiment, the blood sample and the reagent are mixed with a predetermined volume ratio R (R=reagent volume/blood volume). All or part of the mixture is then transferred to pass through the fluidic configuration having the sheathless flow cell and the flow sensor for signal measurements. The measured signals are recorded versus time as shown in the non-limiting examples of FIGS. 9B-9E. Time $T_1$ and $T_2$ are when the sample reaches the two sensing zones, e.g. sensing zone 1 and sensing zone 2 of the flow sensor, respectively. The recorded signal is then used to characterize and numerate the blood cells and also to obtain the absolute count of the blood cells.

Figure 9B:
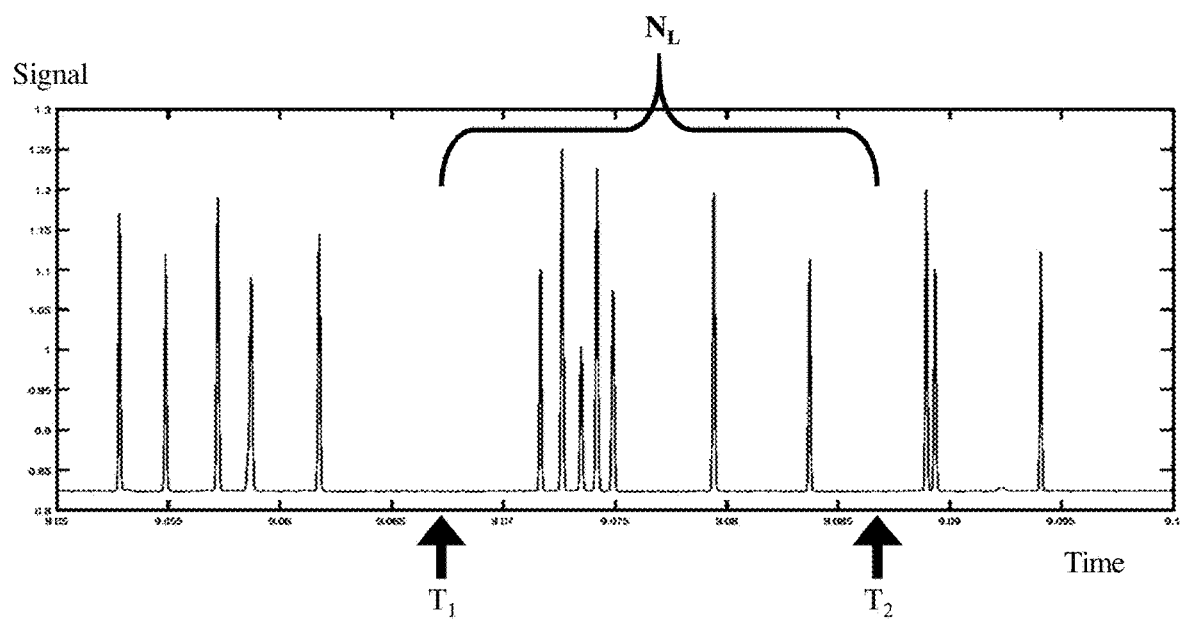

FIG. 9B shows one example of the signal recorded for the leukocyte count. The signal can be fluorescence signal, or light scattering signal or other signals to detect the leukocyte cells in the sample mixture. The number of leukocyte cells detected $N_L$ is determined by the number of peaks in the recorded signal. With the known design parameter $V_0$, which is the fluid volume to fill up the fluidic conduit between the two sensing zones, the absolute count of the leukocyte cells in the mixture $C_{L1}$ is determined in the fluidic configuration as described herein.

$$C_{L1} = N_L/V_0 \qquad [4]$$

In some embodiment, the blood sample and the reagent are mixed with a predetermined volume ratio R. Thus, the absolute count of the leukocyte cells in the initial blood sample $C_{L0}$ is then calculated as:

$$C_{L0} = (R+1) \cdot C_{L1} = (R+1) \cdot N_L/C_0 \qquad [5]$$

Different types of treatment reagents and correspondingly different types of optical signals can be used in the measurement to achieve the leukocyte count or leukocyte differential, or both. More information regarding exemplary reagents and signal measurements can be found in U.S. Pat. Nos. 3,497,690, 3,883,247, 4,400,370, 4,615,878, 4,500,509, 4,400,370, 4,581,233, 4,615,878, 6,955,872, US 2014/0273060, US 2012/0282598, U.S. Pat. Nos. 5,879,900, 6,869,798, US 2013/0137135, U.S. Pat. No. 5,510,267, US 2012/0282598, US 2014/0273060, U.S. Pat. Nos. 5,232,857, 7,981,681, 7,235,404, 8,163,559, 7,592,179, 5,747,343, 5,639,630, 5,618,733, 4,810,487, 6,004,816, 8,101,414 and 6,524,858, which are incorporated herein by reference in their entirety as if fully set forth.

In some embodiments, the treatment reagent contains a fluorescent dye (e.g., a nucleic acid dye that has high affinity binding to the nucleus of the leukocyte cells) and the optical signal measurement measures at least the fluorescence from the dye binding to the leukocyte cells. The fluorescence can be triggered by light of a selected wavelength range that illuminates the sample in the flow cell, and the recorded signal is the intensity of the triggered fluorescence emission within a selected wavelength range. Different types of fluorescent nucleic acid dyes can be used, and examples include but are not limited to Propidium Iodide, Ethidium Bromide, DAPI, Hoechst dyes, Acridine Orange, Thiazole Orange, 7-AAD, LDS751, Basic Orange 21, hydroxystibamidine, and any other nucleic acid fluorescent dyes. In some embodiments, the treatment reagent contains additional compounds or chemicals to accelerate the dye penetrating the leukocyte cell membrane. Examples of such a penetrating compound/chemical include but are not limited to protein crosslink agents such as formaldehyde, glutaraldehyde, etc.; organic solvents such as methanol, 2-phenoxyethanol, ethanol, etc.; surfactant such as Saponin, Tweeen-20, Triton X-100, etc.; and their equivalents.

In some embodiments, the sample treatment reagent contains a lysing compound/chemical that lyses the erythrocyte cells while keeps the leukocyte cells intact. Examples of such a lysing compound/chemical include but are not limited to ammonium salts, quaternary ammonium salts, pyridinium salts, hydroxylamine salts, nonionic surfactants, ionic surfactants, dodecyl sodium sulfate (SDS), lauryl sodium sulfate (SLS), and their combinations, and any other known erythrocyte lysing compound/chemical. Accordingly, the light signal measurement measures at least the intensity of the light scattering from the sample passing through the flow cell. On one hand, the lysing treatment breaks the erythrocyte cells' membranes, releasing hemoglobin and rendering them transparent to the light scattering measurement. On the other hand, the lysing treatment either keeps the leukocyte cells intact or releases only part of the cytoplasm, leaving them still able to introduce significant light scattering. Light scattering in different angles can be measured. For one example, it can be the forward light scattering in the angles of 0-1, 1-3, 3-5, or 5-12 degrees, or above 12 degrees. In some embodiments, the sample treatment reagent contains additional compounds or chemicals to dissolve the debris of erythrocyte cells after the lysing treatment. Examples of such a dissolving compound/chemical include but are not limited to surfactants that selectively dissolve cholesterol such as Saponin; surfactants that non-selectively solubilize lipid such as Tween-20, Triton X-100, etc.; and their equivalents. In some embodiments, additional compounds/chemicals can be added to the mixture to preserve the leukocyte cells to keep them intact when lysing the erythrocyte cells. Examples of such a preserving compound/chemical include but are not limited to formaldehyde, glutaraldehyde, butoxyethaol, phenoxyethanol, isopropyl alcohol, methyl alcohol, ethyl alcohol, and methanol, and their equivalent thereof.

In some embodiments, the treatment reagent can contain both a nucleic acid fluorescent dye and a lysing compound/chemical. Then, the leukocyte cells can be detected in the flow cell by either the fluorescence intensity, or the light scattering intensity, or both. In some embodiments, the measured optical signals (e.g. fluorescence, light scattering, light absorption, etc.) can be used to further classify the leukocyte cells into subtypes, which include but not limit to lymphocyte, monocyte, neutrophil, eosinophil, basophil, granulocyte and immature granulocytes. The leukocyte differential (the percentages of leukocyte subtypes) is then determined from the number of the peaks of each subtype divided by the number of the peaks of all the subtypes.

In addition to the components/chemicals, other parameters (e.g., osmolality, pH level and temperature) of the sample mixture are also important to introduce the fluorescence labeling of the leukocyte cells or to keep leukocyte cells intact while lysing the erythrocyte cells. In certain embodiments, the osmolality of the sample mixture is adjusted to be 280 to 300, 240 to 320, 200-350, or 140-400 mOsm/L. In certain embodiments, the osmolality range for the sample mixture is 140-160, 160-180, 180-200, 200-220, 220-240, 240-260, 260-280, 280-300, 300-320, 320-340, 340-360, 360-380, or 380-400 mOsm/L. Additional compounds/chemicals can be added to the sample treatment reagent to adjust the osmolality of the sample mixture to the desired range. Examples of the osmolality-adjusting compound/chemical include but are not limited to: salts containing cations (e.g., $Na^+$, $K^+$, $NH4^+$, $Ca^{2+}$ and $Mg^{2+}$ containing salts); salts containing anions (e.g., $Cl^-$, $Br^-$, $NO_3^-$, $CO_3^{2-}$, $HCO_3^-$, $SO_4^{2-}$, $HSO_4^-$, $PO_4^{3-}$, $HPO_4^{2-}$, $H_2PO_4^-$, $COOH^-$ and $CH_3COO^-$); organic compounds such as sugars (e.g., glucose and sucrose); and alcohols (e.g., ethanol and methanol). In certain embodiments, the pH level is in the range of 6-7, 7-8, 8-10. In some embodiments, the sample mixture is incubated at a temperate of 15-50 Celsius degrees (° C.) to accelerate or stabilize the treatment before analysis in the flow cell.

Figure 9C:
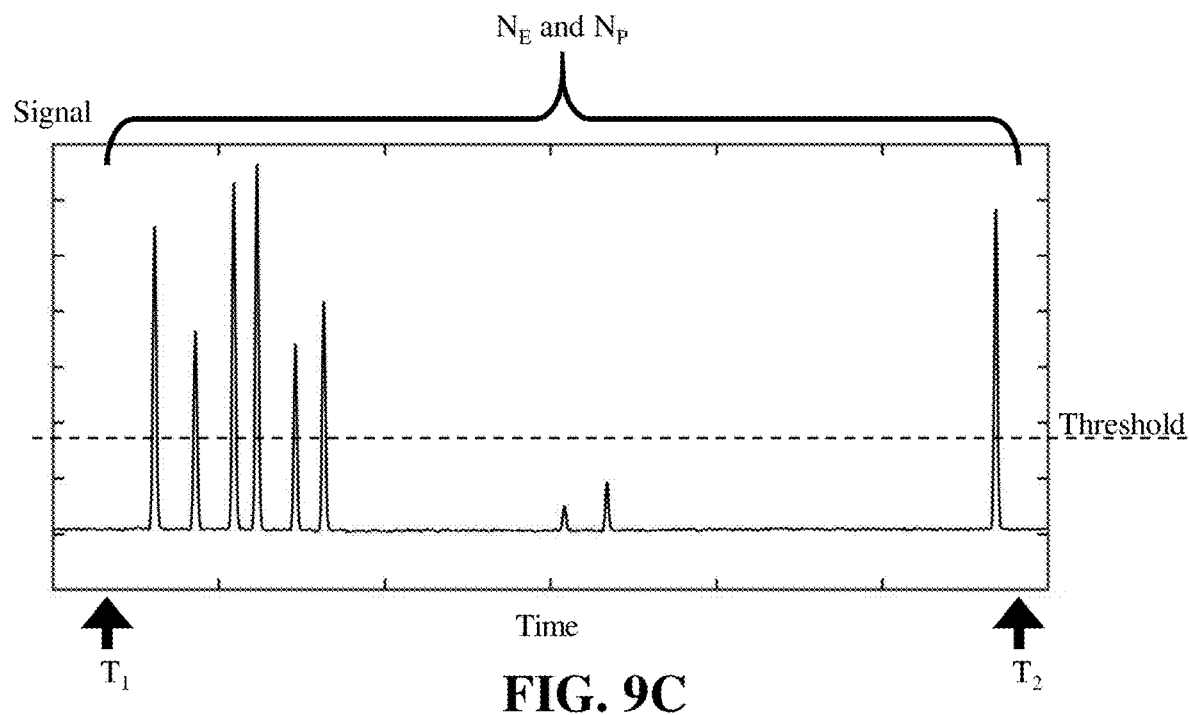

FIG. 9C shows one non-limiting example of the signal measured for erythrocyte count and platelet count. Between $T_1$ and $T_2$, the number of erythrocyte cells $N_E$ and the number of platelet cells $N_P$ are determined from the number of peaks in the recorded signal. In some embodiments, the peaks with an intensity higher than a predetermined threshold are used to determine $N_E$, while the peaks with an intensity lower than the threshold are used to determine N. In some embodiments, other methods are used to distinguish the erythrocyte cell peaks and the platelet cell peaks (see e.g., U.S. Pat. No. 4,735,504, which is incorporated herein by reference in its entirety as if fully set forth). The absolute count of the erythrocyte cells $C_{E1}$ and the platelet cells $C_{P1}$ in the mixture are determined as:

$$C_{E1}=N_E/V_0 \quad [6]$$

$$C_{P1}=N_P/V_0 \quad [7]$$

In some embodiment, the blood sample and the reagent are mixed with a predetermined volume ratio R. Thus, the absolute count of the erythrocyte cells $C_{L0}$ and the platelet cells $C_{P0}$ in the initial blood sample are then calculated as:

$$C_{E0}=(R+1) \cdot C_{E1}=(R+1) \cdot N_E/C_0 \quad [8]$$

$$C_{P0}=(R+1) \cdot C_{P1}=(R+1) \cdot N_P/C_0 \quad [9]$$

Different types of treatment reagents and correspondingly different types of optical signals can be measured for the erythrocyte count and platelet count. In some embodiment, the measurement is also used to determine other erythrocyte and platelet related parameters, which include but are not limit to the reticulocyte count, the nucleated erythrocyte cell count, the erythrocyte indices (e.g., hematocrit, mean corpuscular volume (MCV), mean corpuscular hemoglobin (MCH), mean corpuscular hemoglobin concentration (MCHC), and red cell distribution width (RDW)), and platelet indices (e.g., mean platelet volume (MPV), plateletcrit (PCT), platelet distribution width (PDW), and platelet large cell ratio (PLCR)). More information regarding exemplary reagents and signal measurements can be found in U.S. Pat. Nos. 4,735,504, 6,664,110, 4,336,029, 4,971,917, 4,981,803, 4,985,174, 5,733,784, 5,891,731, 6,114,173, 8,940,499, 5,874,310, 5,917,584, 6,573,102, 6,673,618, 7,008,792, U.S. Pat. No. 774,622, U.S. Pat. No. 4,882,284, and US 2008/0102526, which are incorporated herein by reference in their entirety as if fully set forth.

In some embodiments, the treatment reagent is a dilution buffer, and the optical signal measurement measures at least the light scattering. Both the erythrocyte cells and the platelet cells remain intact in the sample mixture. The peaks in the recorded light scattering signal indicate the cells being detected in the flow cells, and the intensity of the peaks distinguishes the erythrocyte cells and the platelet cells. Examples of the light scattering signals include but are not limited to the scattering in the angles of 1-3, 3-5, 5-12 or above 12 degrees, or their combinations. Other scattering angels can also be used to detect and distinguish the erythrocyte cells and platelet cells, as taught in the U.S. Pat. No. 4,735,504.

Examples of the dilution buffer include but are not limited to water solution of sodium chloride, or potassium chloride, or phosphate-buffered saline or their equivalents. The osmolality of the dilution buffer is adjusted to minimize undesired lysing of the erythrocyte cells. In certain embodiments, the osmolality range for the sample mixture is 280-300, 240 to 320, 200-350, or 140-400 mOsm/L. In certain embodiments, the osmolality range for the sample mixture is 140-160, 160-180, 180-200, 200-220, 220-240, 240-260, 260-280, 280-300, 300-320, 320-340, 340-360, 360-380, or 380-400 mOsm/L. Additional compounds/chemicals can be added to the sample treatment reagent to adjust the osmolality of the sample mixture to the desired range. Examples of the osmolality-adjusting compound/chemical include but are not limited to: salts containing cations (e.g., $Na^+$, $K^+$, $NH4^+$, $Ca^{2+}$ and $Mg^{2+}$ containing salts); salts containing anions (e.g., $Cl^-$, $Br^-$, $NO_3^-$, $CO_3^{2-}$, $HCO_3^-$, $SO_4^{2-}$, $HSO_4^-$, $PO_4^{3-}$, $HPO_4^{2-}$, $H_2PO_4^-$, $COOH^-$ and $CH_3COO^-$); organic compounds such as sugars (e.g., glucose and sucrose); and alcohols (e.g., ethanol and methanol).

In some embodiments, the treatment reagent also contains erythrocyte cell sphering compound/chemical. Examples of the sphering compound/chemical include but are not limit to surfactants such as sodium dodecyl sulfate (SDS) and sodium lauryl sulfate (SLS), etc. The sphering compound/chemical transforms the erythrocyte cells from disk shape into sphere shape. When the erythrocyte cells are in disk shape, the intensity of the forward light scattering is dependent on the orientation of the cells in the flow cell. When the erythrocyte cells are in sphere shape, the intensity of the forward light scattering is only minimally or no longer dependent on the orientation of the cells in the flow cell In some embodiments, the treatment reagent also contains a fluorescent dye, such as a nucleic acid dye that has high affinity binding to DNA, or RNA or both of DNA and RNA. The fluorescence from the dye labeling and the light scattering signal are used together to distinguish the platelet cells from the erythrocyte cells. Non-limiting examples of the reagent and the measured fluorescence and light scattering signals can be found in U.S. Pat. No. 4,882,284 and US 2008/0102526, which are incorporated herein by reference in their entirety as if fully set forth. Other fluorescence dyes and optical signals can also be used to detect the erythrocyte cells, platelet cells, reticulocyte cells and nucleated erythrocyte cells. Non-limiting examples of the reagent and the measured signals can be found in U.S. Pat. Nos. 4,971,917, 4,981,803, 8,940,499, 6,664,110, and 7,674,622, which are incorporated herein by reference in their entirety as if fully set forth.

Figure 9D:
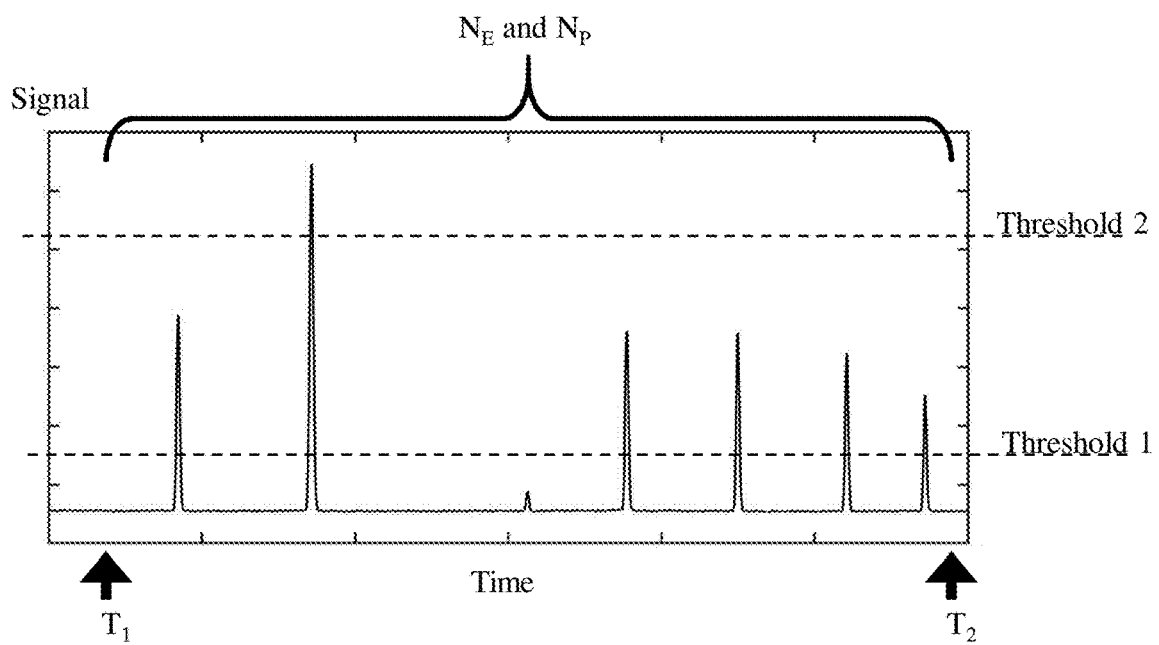

In some embodiments, the treatment reagent also contains micro beads with predetermined sizes. In the sheathless flow cell, the measured signals from the erythrocyte cells or from the platelet cells are compared to the signals measured from the micro beads, so as to quantify the sizes of the erythrocyte cells or the platelet cell by the predetermined sizes of the beads. A non-limiting example is shown in FIG. 9D, where a plurality of micro beads that having a predetermine sizes larger than the erythrocyte cells are used in the treatment reagent. The peaks in the recorded signal are compared to two predetermined thresholds, threshold 1 and threshold 2. Peaks with heights lower than the threshold 1 are determined as platelet cells. Peaks with heights higher than the threshold 1 but lower than the threshold 2, are determined as erythrocyte cells. Peaks with heights higher than the threshold 2 are determined as the micro beads. The peak heights of the beads are then used as a size standard to quantity the size of the detected erythrocyte cells and platelet cells. In some embodiments, the recorded signal is a light scattering signal, or a combination of light scattering signals. In some embodiment, the sizes of the micro beads are equal to or smaller than the erythrocyte cells. In some embodiments, the sizes of the micro beads are in the range of 0.1-1, 1-2, 2-6, 6-8, 8-10, 10-15, 25-30, 30-50, or 50-100 μm.

Figure 9E:
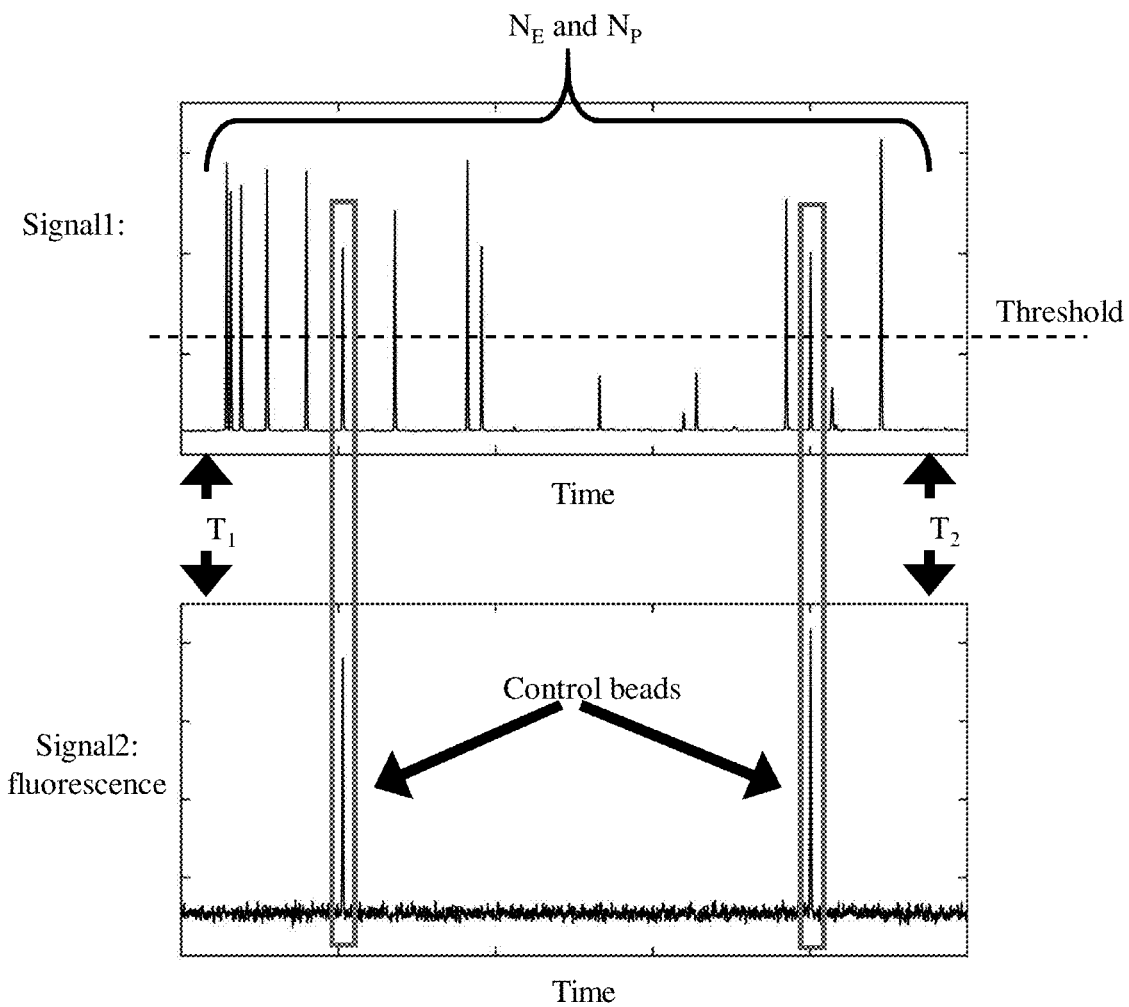

In some embodiments, the micro beads are pre-labeled with fluorophore. The fluorescence from the fluorophore-labeled beads is measured in the flow cell to distinguish the detected beads from the detected erythrocyte cells and platelet cells. A non-limiting example is shown in FIG. 9E, where two signals, Signal 1 and Signal 2, are measured simultaneously in the sheathless flow cell. The Signal 2 measures the intensity of fluorescence within a wavelength range of the bead's fluorophore. The peaks in the Signal 2 detected the micro beads. The timings of these peaks in the Signal 2 are then used to identify the peaks of the beads in the Signal 1. The rest of the peaks in the Signal are identified either as erythrocyte cells or platelet cell, by comparing to a predetermined threshold. The size of the erythrocyte cells and the platelet cells are quantified by comparing their peak heights to the peak heights of the beads with the predetermined size in the Signal 1. In some embodiment, the recorded Signal 1 is a light scattering signal, or a combination of light scattering signals. In some embodiments, the sizes of the micro beads are in the range of 0.1-1, 1-2, 2-6, 6-8, 8-10, 10-15, 25-30, 30-50, or 50-100 μm.

Another parameter in CBC testing is the hemoglobin concentration. FIG. 10A shows a diagram of the method to measure the hemoglobin concentration. A blood sample and a sample treatment reagent are mixed to form a sample mixture, which is then transferred into a cuvette for measurement of the hemoglobin concentration. In some embodiment, the measurement is an optical measurement that includes but is not limited to the light absorption measurement. The cuvette is defined as a container that has two surfaces in parallel, as shown in FIG. 10B, the distance between which is filled up with the sample for the light absorption measurement. In the absorption measurement, the optical path length L is equal to the distance between the two parallel surfaces of the cuvette. In some examples of the method, the light absorption measurement is made when the sample is moving through the cuvette, as shown in the example of FIG. 11A. In other examples of the method, the light absorption measurement is made when the sample is stationary in the cuvette, as shown in the example of FIG. 11B. The cuvette can be of any shape. The measured light absorption is used to determine the hemoglobin concentration $C_{H1}$ in the sample mixture, following the Beer-Lambert Law:

$$C_{H1} = \frac{A}{\varepsilon \cdot L} \quad [10]$$

where A is the light absorption measured, L is the optical path length, and ε is the attenuation coefficient of the hemoglobin mixture, which can be determined by a calibration curve. In some embodiment, the blood sample and the reagent are mixed with a predetermined volume ratio R. Thus, the hemoglobin concentration in the initial blood sample is then determined as:

$$C_{H0} = R \cdot C_{H1} = R \cdot \frac{A}{\varepsilon \cdot L} \quad [11]$$

In some examples, the treatment reagent can be in a liquid form. In some other examples, the treatment reagent can be in a solid form (e.g., dried powder, dried coating on a surface, and dried particles). When the dried reagent is dissolved in the blood sample, it may not change the volume of the blood sample. In this case, the volume ratio R is equal to 1. The light path length L in the cuvette can be of any range. In certain embodiments, the light path length is in the range of 0.1-1, 1-2, 2-5, or 5-10 mm.

Different types of treatment reagent can be used to for the hemoglobin measurement. More information regarding exemplary reagents and signal measurements can be found in U.S. Pat. Nos. 5,958,781, 5,834,315, 7,235,404, 5,242,832, 7,981,681, 4,853,338, 5,866,428, 5,763,280, 5,834,315, 4,997,769, 5,968,832, 5,242,832, 5,866,428, 5,958,781 and 8,614,066, which are incorporated herein by reference in their entirety as if fully set forth.

In some embodiments, the treatment reagent may contain a compound/chemical that lyses the erythrocyte cells to release hemoglobin into the sample mixture. Examples of the lysing compound/chemical include but are not limited to surfactants (e.g., SDS, SLS, saponins, Triton-X100, quaternary ammonium salts, and pyridinium salts). In some embodiments, the treatment reagent may contain a compound/chemical that converts the released hemoglobin into oxyhemoglobin. Examples of the oxyhemoglobin-converting compound/chemical include but are not limited to oxygen, ammonium hydroxide, and peroxide. In some embodiments, the treatment reagent may contain a compound/chemical that converts the released hemoglobin into methemoglobin. Examples of the methemoglobin-converting compounds/chemicals include but are not limited to potassium cyanide, potassium ferricyanide, dmenthyllaurylamine oxide, SDS, and SLS. In some embodiments, the treatment reagent may contain a compound/chemical that converts the released hemoglobin further into other forms of chromogen, such as cyanmethemoglobin, haemiglobinazide, haemiglobinsulphate, and alkaline haematin. Examples of the chromogen-converting compounds/chemicals include but are not limited to potassium cyanide, potassium ferricyanide, sodium azide, SDS, SLS, Triton X-100, and sodium hydroxide.

The wavelength of the light absorption is chosen to measure the released hemoglobin or its stabilized forms such as oxyhemoglobin, methemoglobin, cyanmethemoglobin, haemiglobinazide, haemiglobinsulphate, and alkaline haematin. In some examples, one band of wavelength (e.g., 520-540 nm, 540-560 nm, and 560-580 nm) is used for the absorption measurement of the hemoglobin or its stabilized forms. In other examples, in addition to the wavelength band to measure the absorption measurement of the hemoglobin or its stabilized forms, a second wavelength band is used to quantify other factors impacting the measurement accuracy, such as scratch on the cuvette surface, or lipid and particles in the sample mixture. Examples of the second wavelength band include but are not limited to 700-800 nm, 800-850 nm, or any wavelength higher than 850 nm.

The various methods as described herein (e.g., those for measuring the leukocyte count, leukocyte differential, erythrocyte count, platelet count, erythrocyte indices, platelet indices, and hemoglobin concentration) can be used in various combinations to deliver full CBC panels, or part of the CBC panels.

Figure 12:
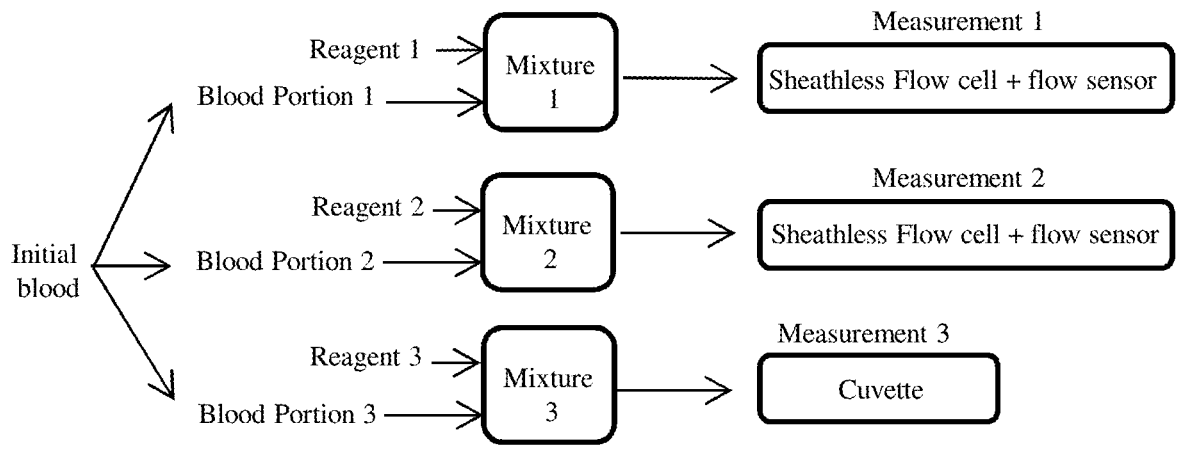
FIGS. 12-16 illustrate, in accordance with various embodiments of the disclosure, diagrams of various exemplary combinations to deliver a full CBC panel.

FIG. 12 shows the diagram of one exemplary combination to deliver a full CBC panel. An initial blood sample is divided into three portions. In some embodiments, this division is achieved by using a pipetting method to transfer predetermined volume of the blood into the three portions. In some embodiments, this division is achieved by using fluid conduits to collect predetermined volume of the blood into the portions. One portion of the blood sample (portion 1) and a reagent 1 are mixed to form a sample mixture 1. All or part of the sample mixture 1 is used for the measurement 1, where the sample is transferred into a fluidic configuration of the sheathless flow cell and the flow sensor for erythrocyte count, or platelet count, or erythrocyte indices, or platelet indices, or any combination of these parameters. Any of the reagents and the corresponding signals for the erythrocyte and platelet detection as described herein can be used for the reagent 1 and the measurement 1. Another portion of the blood sample (portion 2) and a reagent 2 are mixed to form the sample mixture 2. All or part of the sample mixture 2 is then used for the measurement 2, where the sample is transferred into a fluidic configuration of the sheathless flow cell and the flow sensor for the leukocyte count or leukocyte differential or a combination of both. Any of the reagents and the corresponding signals for the leukocyte detection as described herein can be used for the reagent 2 and the measurement 2. In some embodiments, the measurement 1 and the measurement 2 are conducted in one unit of the configuration of the sheathless flow cell and the flow sensor. In some embodiments, the measurement 1 and the measurement 2 are conducted in two separated units of the configuration of the sheathless flow cell and the flow sensor. Another portion of the blood sample (portion 3) and a reagent 3 are mixed to form the sample mixture 3. All or part of the sample mixture 3 is then used for the measurement 3, where the sample is transferred into a cuvette for the measurement of the hemoglobin concentration. Any of the reagents and the corresponding signals for the hemoglobin detection as described herein can be used for the reagent 3 and the measurement 3. In some embodiments, the erythrocyte indices involving hemoglobin, such as MCH and MCHC, can be calculated from the results of the measurement 1 and measurement 3.

Figure 13:
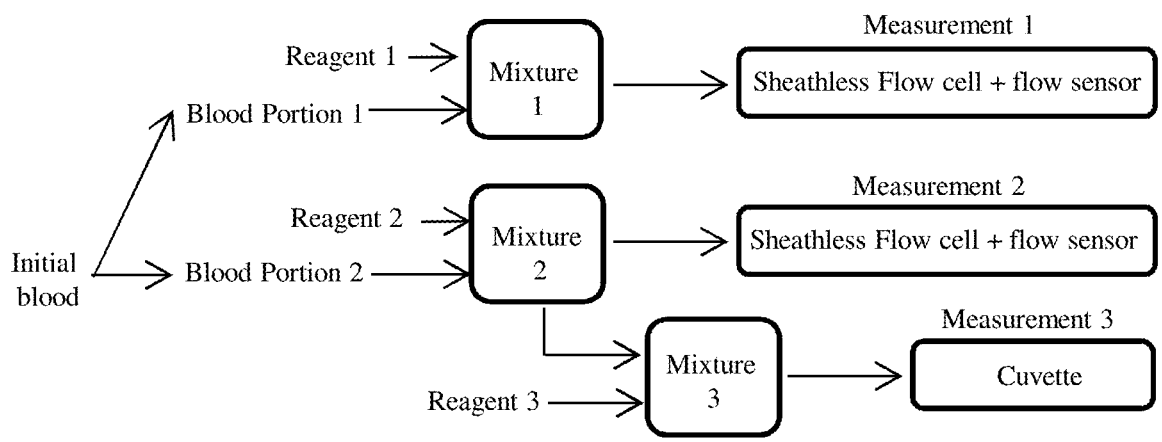

FIG. 13 shows the diagram of another exemplary combination to deliver a full CBC panel. An initial blood sample is divided into two portions. In some embodiments, this division is achieved by using a pipetting method to transfer predetermined volume of the blood into the portions. In some embodiments, this division is achieved by using fluid conduits to collect predetermined volume of the blood into the portions. One portion of the blood sample (portion 1) and a reagent 1 are mixed to form a sample mixture 1. All or part of the sample mixture 1 is used for the measurement 1, where the sample is transferred into a fluidic configuration of the sheathless flow cell and the flow sensor for erythrocyte count, or platelet count, or erythrocyte indices, or platelet indices, or any combination of these parameters. Any of the reagents and the corresponding signals for the erythrocyte and platelet detection as described herein can be used for the reagent 1 and the measurement 1. The other portion of the blood sample (portion 2) and a reagent 2 are mixed to form the sample mixture 2. Part of the sample mixture 2 is then used for the measurement 2, where the sample is transferred into a fluidic configuration of the sheathless flow cell and the flow sensor for the leukocyte count or leukocyte differential or a combination of both. Any of the reagents and the corresponding signals for the leukocyte detection as described herein can be used for the reagent 2 and the measurement 2. In some embodiments, the measurement 1 and the measurement 2 are conducted in one unit of the configuration of the sheathless flow cell and the flow sensor. In some embodiments, the measurement 1 and the measurement 2 are conducted in two separated units of the configuration of the sheathless flow cell and the flow sensor. Another part of the sample mixture 2 is then mixed with a reagent 3 to form the sample mixture. All or part of the sample mixture 3 is used for the measurement 3, where the sample is transferred into a cuvette for the measurement of the hemoglobin concentration. Any of the reagents and the corresponding signals for the hemoglobin detection as described herein can be used for the reagent 3 and the measurement 3. In some embodiments, the erythrocyte indices involving hemoglobin, such as MCH and MCHC, can be calculated from the results of the measurement 1 and measurement 3.

Figure 14:
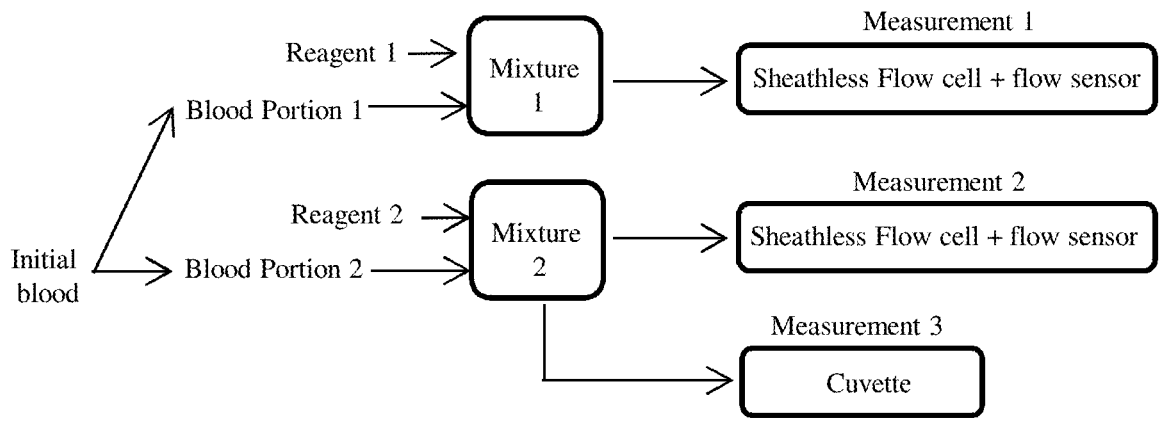

FIG. 14 shows the diagram of another exemplary combination to deliver a full CBC panel. An initial blood sample is divided into two portions. In some embodiments, this division is achieved by using pipetting method to transfer predetermined volume of the blood into the portions. In some embodiments, this division is achieved by using fluid conduits to collect predetermined volume of the blood into the portions. One portion of the blood sample (portion 1) and a reagent 1 are mixed to form a sample mixture 1. All or part of the sample mixture 1 is used for the measurement 1, where the sample is transferred into a fluidic configuration of the sheathless flow cell and the flow sensor for erythrocyte count, or platelet count, or erythrocyte indices, or platelet indices, or any combination of these parameters. Any of the reagents and the corresponding signals for the erythrocyte and platelet detection as described herein can be used for the reagent 1 and the measurement 1. The other portion of the blood sample (portion 2) and a reagent 2 are mixed to form the sample mixture 2. Part of the sample mixture 2 is then used for the measurement unit 2, where the sample is transferred into a fluidic configuration of the sheathless flow cell and the flow sensor for the leukocyte count or leukocyte differential or a combination of both. Another part of the sample mixture 2 is used for the measurement 3, where the sample is transferred into a cuvette for the measurement of the hemoglobin concentration. Reagents and the corresponding signals for leukocyte count and the hemoglobin measurement are discussed above, and their various combinations that either keep the leukocyte intact or only release only part of the leukocyte cytoplasm can be used for the reagent 2. A non-limiting example of the reagent 2 is a lysing reagent that lyse the erythrocyte cells to release the hemoglobin, but keeps the leukocyte cells intact for the following cytometer measurement as described herein. Examples of such a lysing compound/chemical include but are not limited to ammonium salts, quaternary ammonium salts, pyridinium salts, hydroxylamine salts, nonionic surfactants, ionic surfactants, dodecyl sodium sulfate (SDS), lauryl sodium sulfate (SLS), and their combinations, and any other known erythrocyte lysing compound/chemical. In certain embodiments, the leukocyte cells remain intact in the mixture 2, where the reagent 2 contains compounds/chemicals that lyse erythrocytes but not lyse the leukocyte cells, and the measurement 2 detects at least one of the following signals, light scattering, fluorescence or electrical impedance. In some embodiments, reagent 2 contains at least one nucleic acid fluorescent dye that labels the nuclei of the leukocyte cell and the measurement 2 at least measures the fluorescence signal from this dye labeling. In some embodiments, the measurement 1 and the measurement 2 are conducted in one unit of the configuration of the sheathless flow cell and the flow sensor. In some embodiments, the measurement 1 and the measurement 2 are conducted in two separated units of the configuration of the sheathless flow cell and the flow sensor. In some embodiments, the erythrocyte indices involving hemoglobin, such as MCH and MCHC, can be calculated from the results of the measurement 1 and measurement 3.

Figure 15:
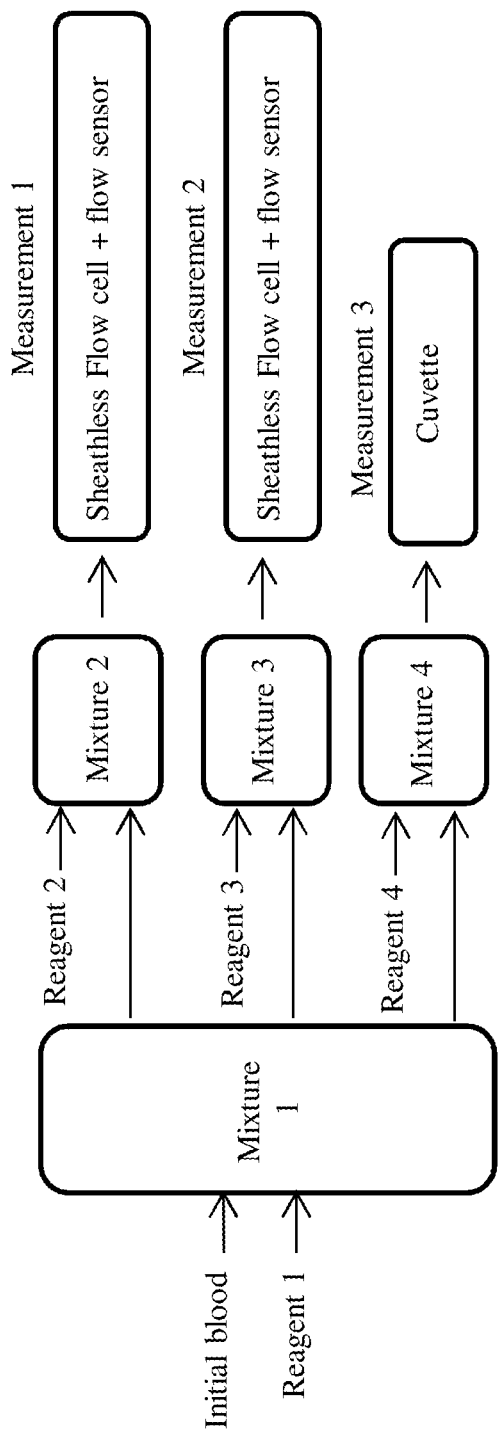

FIG. 15 shows the diagram of another exemplary combination to deliver a full CBC panel. An initial blood sample with predetermined volume and a reagent 1 are mixed to form the sample mixture 1. In the mixture 1, the leukocyte cells, erythrocyte cell and platelet cells are all kept intact without being lysed. The reagent 1 can be of any dilution buffer for blood sample. Non-limiting examples of the dilution buffer include but are not limited to water solution of sodium chloride, or potassium chloride, or phosphate-buffered saline or their equivalent thereof. The osmolality of the dilution buffer is adjusted to minimize undesired lysing of the erythrocyte cells. In certain embodiments, the osmolality range for the sample mixture is 280 to 300, 240 to 320 or 200-350 mOsm/L. In certain embodiments, the osmolality range for the sample mixture is 140-160, 160-180, 180-200, 200-220, 220-240, 240-260, 260-280, 280-300, 300-320, 320-340, 340-360, 360-380, or 380-400 mOsm/L. Part of the sample mixture 1 is mixed with a regent 2 to form a sample mixture 2. All or part of the sample mixture 2 is used for the measurement 1, where the sample is transferred into a fluidic configuration with the sheathless flow cell and the flow sensor for erythrocyte count, or platelet count, or erythrocyte indices, or platelet indices, or any combination of these parameters. Any of the reagents and the corresponding signals for the erythrocyte and platelet detection as described herein can be used for the reagent 2 and the measurement 1. Part of the sample mixture 1 is mixed with a reagent 3 to form a sample mixture 3. All or part of the sample mixture 3 is then used for the measurement 2, where the sample is transferred into a fluidic configuration of the sheathless flow cell and the flow sensor for the leukocyte count or leukocyte differential or a combination of both. Any of the reagents and the corresponding signals for the leukocyte detection as described herein can be used for the reagent 3 and the measurement 2. In some embodiments, the measurement 1 and the measurement 2 are conducted in one unit of the configuration of the sheathless flow cell and the flow sensor. In some embodiments, the measurement 1 and the measurement 2 are conducted in two separated units of the configuration of the sheathless flow cell and the flow sensor.

Part of the sample mixture 1 is mixed with a reagent 4 to form a sample mixture 4. All or part of the sample mixture 4 is used for the measurement 3, where the sample is transferred into a cuvette for the measurement of the hemoglobin concentration. Any of the reagents and the corresponding signals for the hemoglobin detection as described herein can be used for the reagent 4 and the measurement 3. In some embodiments, the erythrocyte indices involving hemoglobin, such as MCH and MCHC, can be calculated from the results of the measurement 1 and measurement 3.

Figure 16:
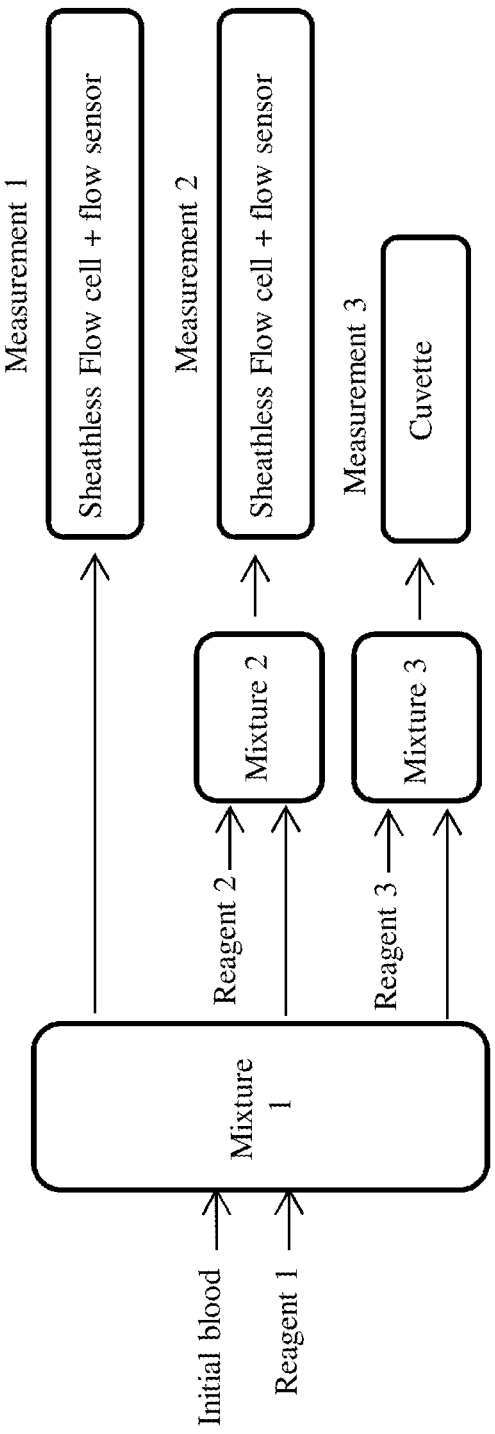

FIG. 16 shows the diagram of another exemplary combination to deliver a full CBC panel. An initial blood sample with predetermined volume and a reagent 1 are mixed to form the sample mixture 1. In the mixture 1, the leukocyte cells, erythrocyte cell and platelet cells are all kept intact without being lysed. Part of the sample mixture 1 is used for the measurement 1, where the sample is transferred into a fluidic configuration with the sheathless flow cell and the flow sensor for the leukocyte count or leukocyte differential or a combination of both. Various examples of the reagents for the leukocyte detection that does not lyse the erythrocyte cells as described herein can be used for the reagent 1. A non-limiting example of the reagent 1 is a diluent buffer that keeps the erythrocyte cell intact and contains a fluorescence nucleic acid dye for the leukocyte detection as described herein. Non-limiting examples of the dilution buffer include but are not limited to water solution of sodium chloride, or potassium chloride, or phosphate-buffered saline or their equivalent thereof. The osmolality of the dilution buffer is adjusted to minimize undesired lysing of the erythrocyte cells. In certain embodiments, the osmolality range for the sample mixture is 280 to 300, 240 to 320 or 200-350 mOsm/L. In certain embodiments, the osmolality range for the sample mixture is 140-160, 160-180, 180-200, 200-220, 220-240, 240-260, 260-280, 280-300, 300-320, 320-340, 340-360, 360-380, or 380-400 mOsm/L. In some embodiments, the measurement 1 at least detects one fluorescence signal. Part of the sample mixture 1 is mixed with a reagent 2 to form a sample mixture 2. All or part of the sample mixture 2 is then used for the measurement 2, where the sample is transferred into a fluidic configuration of the sheathless flow cell and the flow sensor for erythrocyte count, or platelet count, or erythrocyte indices, or platelet indices, or any combination of these parameters. Any of the reagents and the corresponding signals for the erythrocyte and platelet detection as described herein can be used for the reagent 2 and the measurement 2. In some embodiments, the measurement 1 and the measurement 2 are conducted in one unit of the configuration of the sheathless flow cell and the flow sensor. In some embodiments, the measurement 1 and the measurement 2 are conducted in two separated units of the configuration of the sheathless flow cell and the flow sensor. Part of the sample mixture 1 is mixed with a reagent 3 to form the sample mixture 3. All or part of the sample mixture 3 is used for the measurement 3, where the sample is transferred into a cuvette for the measurement of the hemoglobin concentration. Any of the reagents and the corresponding signals for the hemoglobin detection as described herein can be used for the reagent 3 and the measurement 3. In some embodiments, the erythrocyte indices involving hemoglobin, such as MCH and MCHC, can be calculated from the results of the measurement 2 and measurement 3.

In some embodiments of the examples of FIGS. 12-16, the initial blood sample is whole blood. In some embodiments of the examples of FIGS. 12-16, the initial blood sample is a diluted whole blood with a predetermined dilution ratio. In some embodiments of the examples of FIGS. 12-16, the initial blood contains anticoagulants (e.g., Ethylenediaminetetraacetic Acid (EDTA) and Heparin) to prevent coagulation.

The configurations and methods of delivering the CBC parameters and the full panels can be implemented in various fluidic circuits and systems. In some embodiments, a cartridge format is used. In some embodiments, the cartridge having on-board fluidics can be inserted into a reader instrument for operation, as shown in the example of FIG. 17. The cartridge 17101 having the on-board fluidics 17102 is inserted into a docking slot 17202 on the reader instrument 17201. In some embodiments, the reader instrument records and analyzes the signals from the sheathless flow cytometer analysis and the cuvette analysis. In some embodiments, the reader instrument has alignment mechanisms and features to align the sheathless flow cell with the instrument for signal measurement such as optical signals. In some embodiments, the reader instrument also detects the signals from the flow sensor to determine the absolute count. In some embodiments, the reader instrument also applies the pneumatic pressure source to the cartridges to drive the fluid transfer. In some embodiment, the port of receiving the pneumatic pressure on the cartridge is initially sealed, and the instrument piece open this seal so as to apply the pneumatic pressure. In some embodiments, the reader instrument also supports additional actuations such as opening or closing a valve structure in the cartridge fluidics. In some embodiments, the cartridge is self-contained and there is no exchange of liquid samples between the cartridge and the reader instrument. In some embodiments, the cartridge is not self-contained, and the reader instrument has liquid storage and there is liquid exchange between the reader instrument and the cartridge, such as liquid infusion from the reader instrument into the cartridge. In some embodiments, the cartridge stays stationary after being inserted into the reader, whereas the interface for external connections such as the pneumatic pressure source moves to make contact with the cartridge. In other embodiments, the cartridge can be movable after being inserted into the reader, and is moved to make contact with the interface for external connections such as pneumatic pressure sources.

Described herein are various embodiments of the configuration and operation of a basic fluidic unit, fluidic circuits having a plurality of the fluidic unit, and cartridges implementing the fluidic unit or the fluidic circuits. More information regarding the design, operation and manufacturing of the fluid unit can be found in U.S. application Ser. No. 15/176,729 and PCT Application PCT/US16/36426, which are incorporated herein by reference in their entirety as if fully set forth. The configuration and the methods of delivering the CBC parameters can be implemented in these fluidic configurations and cartridges. FIG. 18A illustrates one non-limiting example of the basic fluidic unit to be used in the cartridge. The basic fluidic unit 18001 has a chamber 18002, a venting port 18003 and at least one microfluidic channel 18004 that accesses the chamber and has a valve 18005 on the microfluidic channel. In some embodiments, the chamber has a volume in the range of about 0.01-0.1, 0.1-0.2, 0.2-0.4, 0.4-0.8, or 0.8-2 ml. In some embodiments, the unit 18001 can have one or a plurality of microfluidic channels (each having a valve) accessing the chamber 18002. The operation of this unit depends on gravity or any other force serving as the replacement for gravity (e.g., centrifugal force) to keep fluid in position. Additionally, it uses another force such as pneumatic pressure to transfer fluid. In some embodiments, the valve 18005 can be a passive valve. In some embodiments, the valve 1005 can be an active valve. In some embodiments, the valve 1005 can be a hybrid or combination of passive and active valves. In some embodiments, the valve 1005 can be any design known to one of ordinary skill in the art. FIG. 18B illustrates a symbol drawing that represents a fluidic unit as described herein.

Figure 19A:
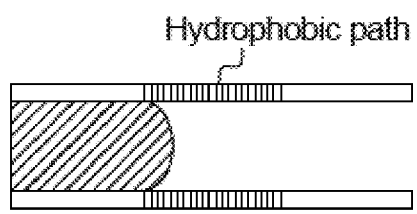
FIGS. 19A-19D illustrate, in accordance with various embodiments of the disclosure, non-limiting examples of passive valves.
Figure 19B:
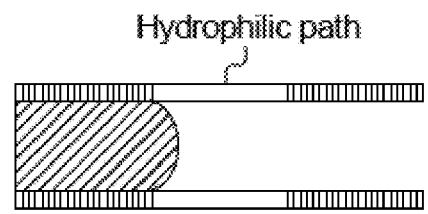
Figure 19C:
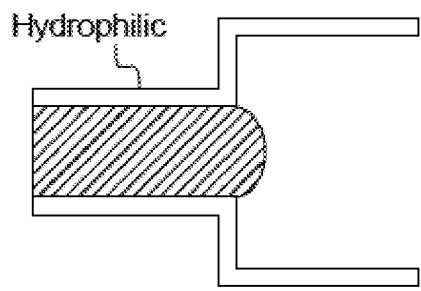
Figure 19D:
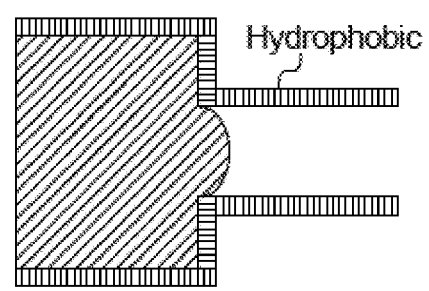

FIGS. 19A-19D illustrate a few non-limiting examples of passive valves. Other passive valve designs known to person skilled in the art can also be used. FIG. 19A is a passive valve design having a channel with hydrophilic inner surface and a patch of hydrophobic surface. FIG. 19B is a passive valve design having a channel with hydrophobic inner surface and a patch of hydrophilic surface. FIG. 19C is a passive valve design having an enlargement of the channel cross-section along the flow direction and the channel has a hydrophilic surface. FIG. 19D is a passive valve design having a narrow down of the channel cross-section along the flow direction and the channel has a hydrophobic surface.

FIGS. 19E-19G illustrate a few non-limiting examples of active valves. Other active valve designs known to person skilled in the art can also be used. FIG. 19E shows a valve design that has a flexible membrane. When the flexible membrane is bent away from the substrate, the valve is in the "open" status to allow fluid flow passing through. When the flexible membrane is bent towards the substrate leaving no gap, the valve is in the "close" status and fluid flow is not able to passing through. FIG. 19F shows a valve design that has a movable membrane. When the movable membrane is away from the substrate, there is a fluid path between the inlet and outlet, and the valve is in "open" status. When the movable membrane is in proximity with the substrate leaving no gap, there is no fluid path between the inlet and the outlet, and the valve is in "close" status. FIG. 19G shows a valve design that has a plug on the channel. When the plug is pulled away from the channel leaving the substrate, the channel is in the "open" status allowing fluid flow from inlet to outlet. When the plug is inserted into the channel contacting the substrate, the channel is in the "close" status and there is no fluid path between the inlet and the outlet. The plug can be made of solid material, polymer, elastomer, gel, wax, silicon oil or other materials. When active valve is used, additional actuation mechanism can be used to operate the valve.

Figure 20A:
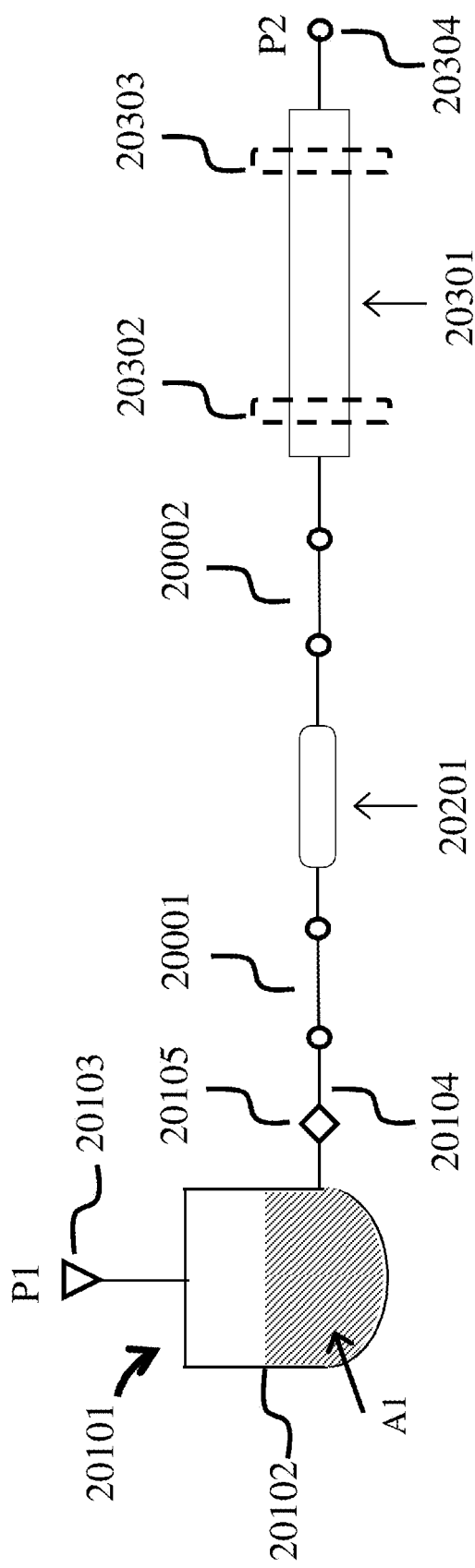
FIGS. 20A-24B illustrate, in accordance with various embodiments of the disclosure, non-limiting examples of using basic fluidic units, sheathless flow cells and flow sensors for detecting, characterizing, obtaining absolute count of blood cells and measuring hemoglobin concentration in CBC.

FIG. 20A shows one non-limiting example of using the basic fluidic unit, the sheathless flow cell and the flow sensor for detecting, characterizing obtaining absolute count of blood cells and measuring hemoglobin concentration in CBC. In this example, a basic fluidic unit 20101, a sheathless flow cell 20201 and a flow sensor 20301 are connected in serial by fluidic conduits 20001 and 20002. The fluidic unit 20101 has a chamber 20102, a venting port 20103 and a microfluidic channel 20104 (with a valve 20105). The flow sensor 20301 has two sensing zones 20302 and 20303. A fluid sample A1 in the chamber 20102 can be transferred into the flow cell 20201 and the flow sensor 20301 for detecting, characterizing and obtaining absolute count of blood cells as described herein. The fluid sample exits the outlet port 20304 of the flow sensor after the measurement. In some embodiments, the sample existing the port 20304 is disposed. In some embodiments, the sample existing the port 20304 is collected in a reservoir, as shown in the non-limiting example of FIG. 20C. A reservoir 20401 with a venting port 20402 is connected to the port 20304 by a fluid conduit 20003 to collect the sample existing the port 20304. In some embodiments, the fluid sample can be measured for the hemoglobin concentration by using the chamber 20102 as the cuvette. In some embodiments, a cuvette can be added in downstream of the fluidic channel 20104 for the hemoglobin measurement.

Figure 20B:
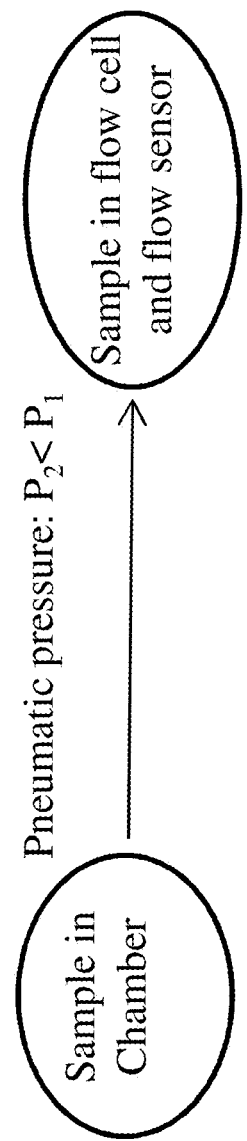
Figure 20C:
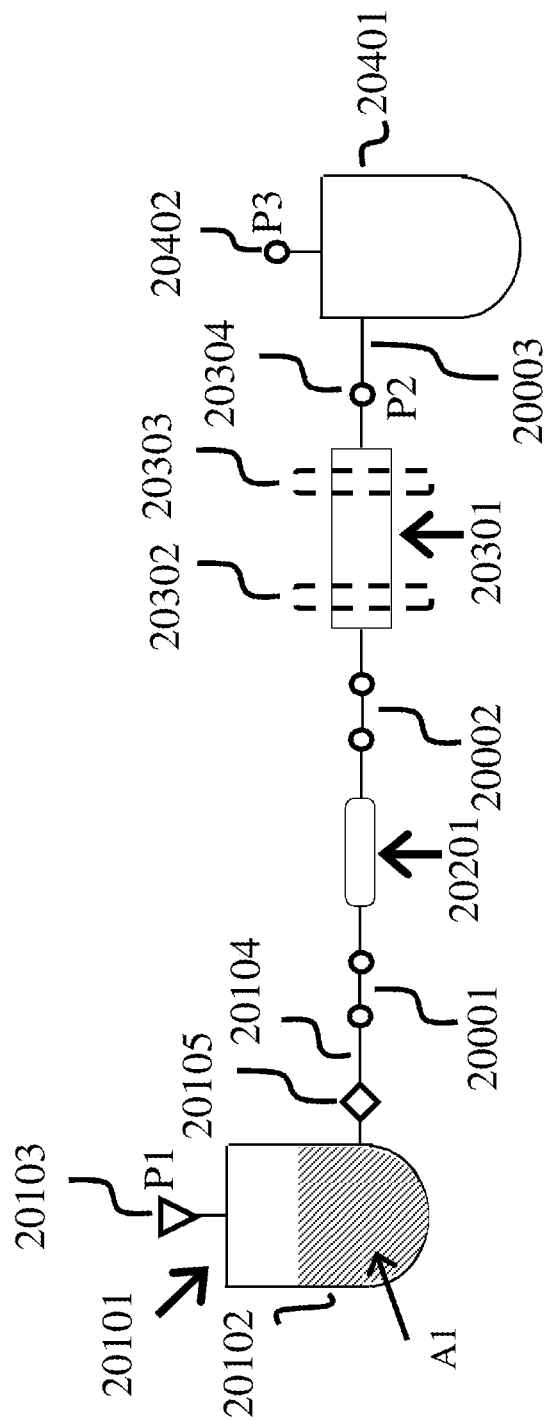
Figure 20D:
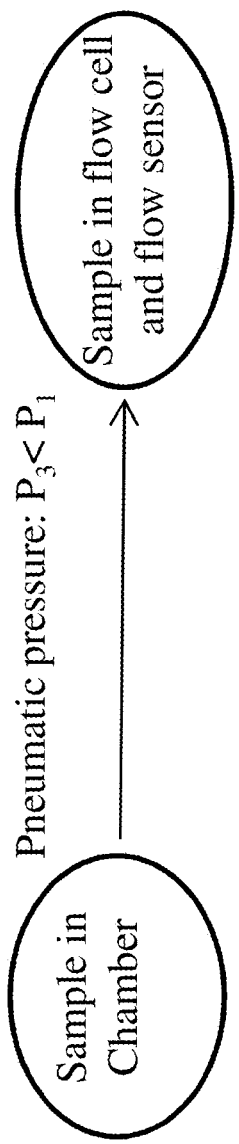

In certain embodiments, the fluid transfer is driven by pneumatic pressure force. FIG. 20B shows a non-liming example of fluid transfer for the configuration of FIG. 20A, by applying pneumatic pressures $P_1$ and $P_2$ to the venting port 20103 of the basic fluidic unit 20101 and the outlet port 20304 of the flow sensor 20301, respectively. The fluid sample can be driven from the chamber to flow through the flow cell and the flow sensor by applying the pneumatic pressure $P_2<P_1$. FIG. 20D shows a non-liming example of fluid transfer for the configuration of FIG. 20C, by applying pneumatic pressures $P_1$ and $P_3$ to the venting port 20103 of the basic fluidic unit 20101 and the venting port 20402 of the reservoir 20401, respectively. In this example, the pressure $P_2$ at the outlet port 20304 of the flow sensor 20301 is indirectly adjusted by the pneumatic pressure $P_3$. The fluid sample can be driven from the chamber to flow through the flow cell and the flow sensor by applying the pneumatic pressure $P_3<P_1$. In some embodiments, the pneumatic pressure $P_1$ in the above two examples is equalized to be the atmosphere pressure $P_0$ where the fluidic configuration is operated in. In certain embodiments, other pumping methods (e.g. electrostatic force, centrifugal force, mechanical pushing, magnetic force, etc.) can be used to transfer the fluid sample for measurement.

In some embodiment, the sample A1 is a mixture of a whole blood and a reagent for the leukocyte detection. Various examples of the leukocyte detection reagents and the corresponding signals measured in the sheathless flow cell as described herein can be used herein. In some embodiment, the sample A1 is a mixture of a whole blood and a reagent for the erythrocyte and platelet detection. Various examples of the erythrocyte and platelet detection reagents and the corresponding signals measured in the sheathless flow cell as described herein can be used herein. In some embodiment, the sample A1 is a mixture of a whole blood and a reagent for the hemoglobin measurement. Various examples of the hemoglobin detection reagents and the corresponding signals measured in the cuvette as described herein can be used herein.

Figure 21A:
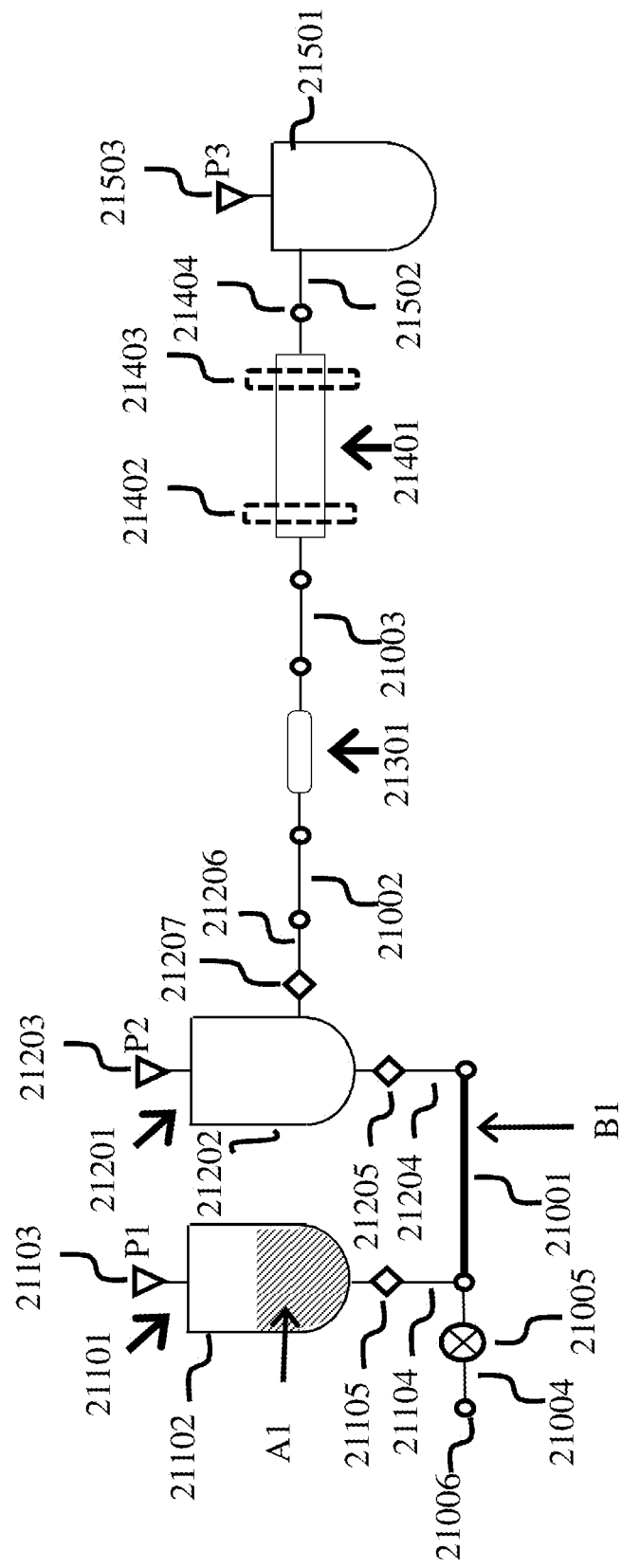

FIG. 21A shows another non-limiting example for detecting, characterizing, obtaining absolute count of blood cells and measuring hemoglobin concentration in CBC. This example has two of the basic fluidic units 21101 and 21201, a sheathless flow cell 21301 and a flow sensor 21401. The basic fluidic unit 21101 has a chamber 21102, a venting port 21103 and a microfluidic channel 21104 with a valve 21105. The basic fluidic unit 21201 has a chamber 21202, a venting port 21203 and two microfluidic channels 20204 with a valve 21205, and 21206 with a valve 21207, respectively. A fluid conduit 21001 connects the channel 21104 and 21204. The inlet of the sheathless flow cell is connecting to the channel 21206 via a fluid conduit 21002. The outlet of the sheathless flow cell is connecting to the flow sensor via a fluidic conduit 21003. The flow sensor 21401 has two sensing zones 21402 and 21403. The outlet 21404 of the flow sensor 21401 is connected to a reservoir 21501 via a fluid conduit 21502. The reservoir 21501 has a venting port 21503.

Figure 21B:
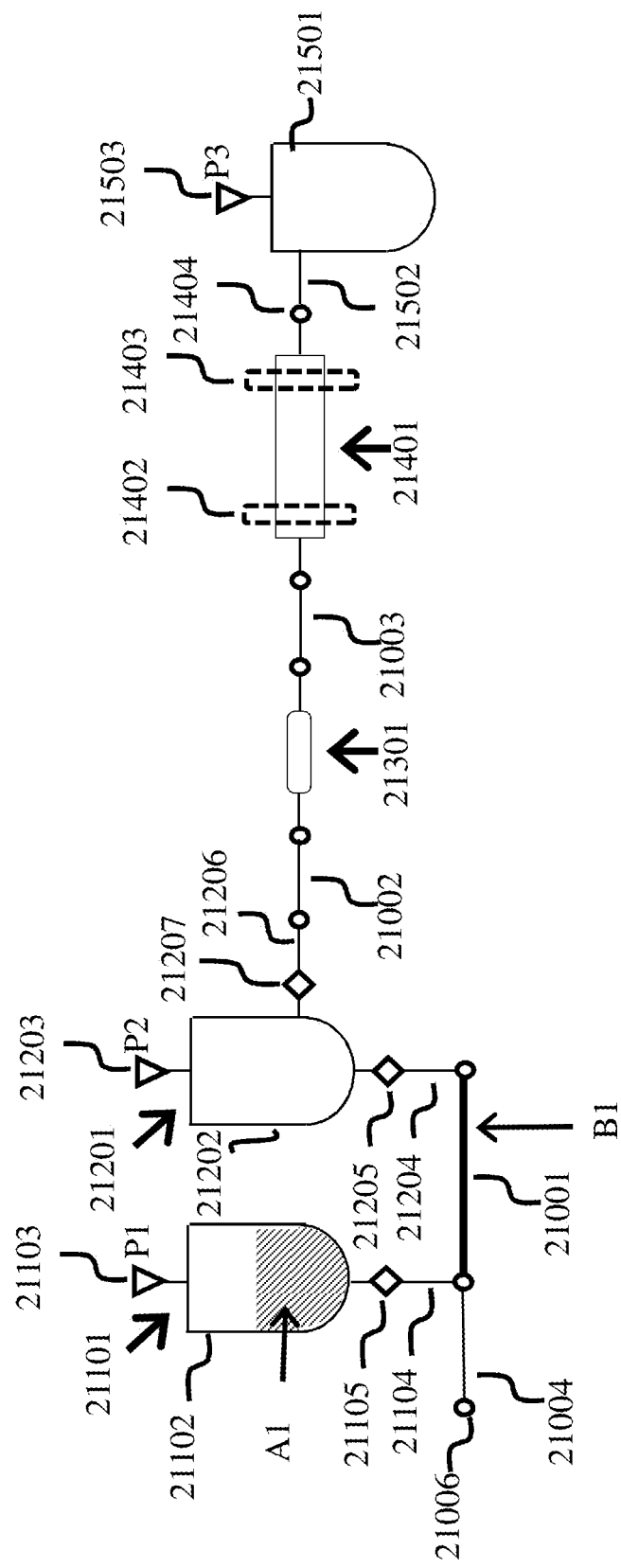

In some embodiments, a reagent A1 is loaded in the chamber 21102 and a sample B1 is introduced into the fluidic conduit 21001. In some embodiment, the reagent A1 has a predetermined volume that is stored on-board in the fluidic cartridge. In some embodiment, the reagent A1 is loaded into the chamber before the analysis. In some embodiments, the sample B1 has a predetermined volume that is collected in the fluid conduit 21001. In some embodiments, the predetermined volumes of the A1 and B1 are used to determine the dilution ratio R. Various methods can be used to introduce the sample B1 into the fluidic conduit 21001. In some embodiments, the sample B1 is introduced via an inlet port 21006 and a fluidic conduit 21004, and a valve 21005 is closed after introducing the sample to prevent sample existing the inlet port 21006 as shown in FIG. 21A. In some embodiments, as the sample B1 is introduced via the inlet port 21006 and the fluidic conduit 21004, and the inlet port 21006 is sealed by an external structure after introducing the sample as shown in FIG. 21B. Examples of the external structure include but are not limited to a mechanical cap, an adhesive seal, etc. In these non-limiting examples, the fluidic conduit 21004 is a stationary feature in the cartridge device.

Figure 21C:
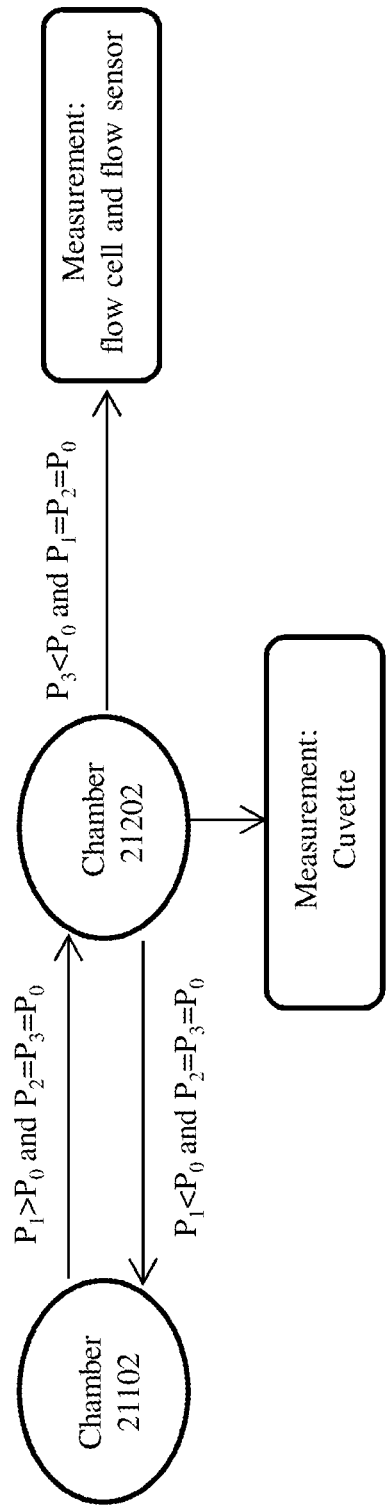

To transfer the fluid samples, in some embodiments, pneumatic pressures are applied to the venting port 21103 ($P_1$), 21203 ($P_2$) and 21503 ($P_3$). FIG. 21C shows an exemplary diagram of using this fluidic configuration. By applying a pneumatic pressure ($P_1 > P_0$, $P_2 = P_3 = P_0$), the reagent A1 is transferred from the chamber 21102 into the chamber 21202, and this action flushes the reagent A1 and the sample B1 into the chamber 21202 to form a sample mixture 1. In some embodiment, the pneumatic pressure $P_0$ is a constant pressure. In some embodiments, the pneumatic pressure $P_0$ is the atmosphere pressure where the fluidic configuration is used in. In some embodiment, the pneumatic pressure ($P_1 > P_0$, $P_2 = P_3 = P_0$) and ($P_1 < P_0$, $P_2 = P_3 = P_0$) can be used in sequential to move the sample mixture 1 from the chamber 21202 into the chamber 21102 and then back into the chamber 20202 again. When a sample mixture is moving out of the chambers and into the fluidic conduit 21001, the sample mixture is focused into a narrower stream, which accelerates the lateral diffusion of the reagent and the sample in the mixture. When a sample mixture is moving out of fluidic conduit 21001 into the chambers, the kinetic flow of sample stream introduces chaotic mixing in the chamber. Both these two actions enhance the mixing uniformity of the sample mixture. By applying a pneumatic pressure ($P_3 < P_0$, $P_1 = P_2 = P_0$), the sample mixture 1 is transferred into the sheathless flow cell and the flow sensor for the cytometer analysis that includes but is not limit to the detection of the leukocyte cells, or erythrocyte cell or platelet cells or any combination of these parameters. In some embodiments, the sample mixture is measured for the hemoglobin concentration either using the chamber 21102 or the chamber 21202 as the cuvette as described herein. In some embodiments, an additional cuvette unit can be added in downstream of the channel 21206 for the hemoglobin measurement.

In some embodiment, the sample B1 is a whole blood and the reagent A1 is a reagent for the leukocyte detection. Various examples of the leukocyte detection reagents and the corresponding signals measured in the sheathless flow cell as described herein can be used herein. In some embodiments, the sample B1 a whole blood and the reagent A1 is a reagent for the erythrocyte and platelet detection. Various examples of the erythrocyte and platelet detection reagents and the corresponding signals measured in the sheathless flow cell as described herein can be used herein. In some embodiment, the sample B1 a whole blood and the reagent A1 is a reagent for the hemoglobin measurement. Various examples of the hemoglobin detection reagents and the corresponding signals measured in the cuvette as described herein can be used herein.

In some embodiments, the sample B1 is a whole blood and the reagent A1 is a combination of a leukocyte detection reagent and a hemoglobin detection reagent. A non-limiting example of the combination contains a leukocyte detection reagent that lyses erythrocyte cells to release hemoglobin but keeps leukocyte cells intact as described herein. With this reagent A1, the measurement of the sample mixture 1 in the flow cell and the flow sensor obtains leukocyte count, or leukocyte differential, or a combination of these parameters. Additionally, the cuvette measurement of the sample mixture 1 obtains the hemoglobin concentration.

Reagents and the corresponding signals for leukocyte count and the hemoglobin measurement are discussed above, and their various combinations that either keep the leukocyte intact or only release only part of the leukocyte cytoplasm can be used for the reagent A1. In certain embodiments, the leukocyte cells remain intact in the sample mixture, where the reagent A1 contains compounds/chemicals that lyse erythrocytes but not lyse the leukocyte cells, and the measurement in the flow cell detects at least one of the following signals, light scattering, fluorescence or electrical impedance. In some embodiments, reagent A1 contains at least one nucleic acid fluorescent dye that labels the nuclei of the leukocyte cell and the measurement in the flow cell at least measures the fluorescence signal from this dye labeling.

Figure 22A:
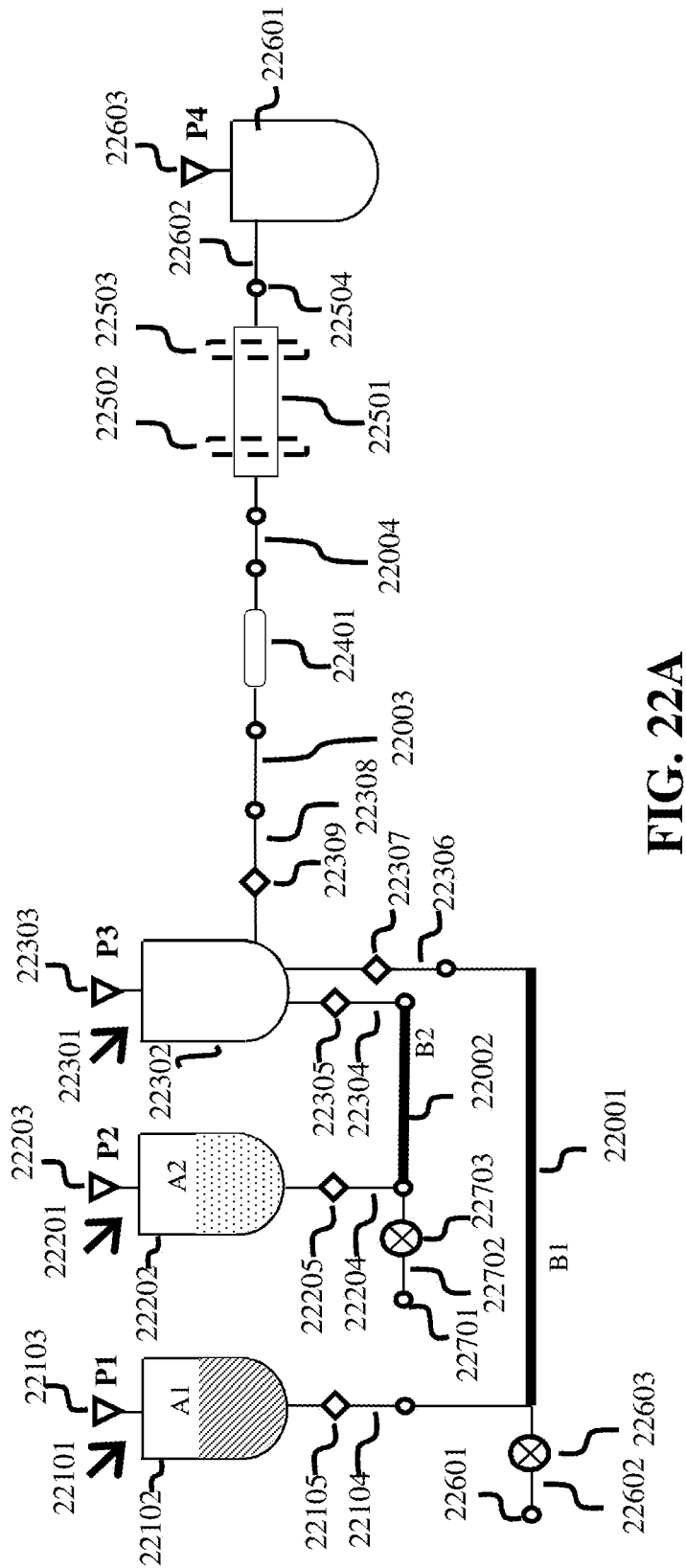

FIG. 22A shows another non-limiting example, which has three of the basic fluidic units 22101, 22201 and 22301, a sheathless flow cell 22401 and a flow sensor 22501. The basic fluidic unit 22101 has a chamber 22102, a venting port 22103 and a microfluidic channel 22104 with a valve 21105. The basic fluidic unit 22201 has a chamber 22202, a venting port 22203 and a microfluidic channel 22204 with a valve 22205. The basic fluidic unit 22301 has a chamber 22302, a venting port 22303 and three microfluidic channels 22304 with a valve 22305, 22306 with a valve 22307 and 22308 with a valve 22309, respectively. A fluid conduit 22001 connects the channel 22104 and 22306. A fluid conduit 22002 connects the channel 22204 and 22304. The inlet of the sheathless flow cell 22401 is connecting to the channel 22308 via a fluid conduit 22003. The outlet of the sheathless flow cell connects to the flow sensor via a fluidic conduit 22004. The flow sensor 22501 has two sensing zones 22502 and 22503. The outlet 22504 of the flow sensor 22501 is connected to a reservoir 22601 via a fluid conduit 22602. The reservoir 22601 has a venting port 22603.

Figure 22B:
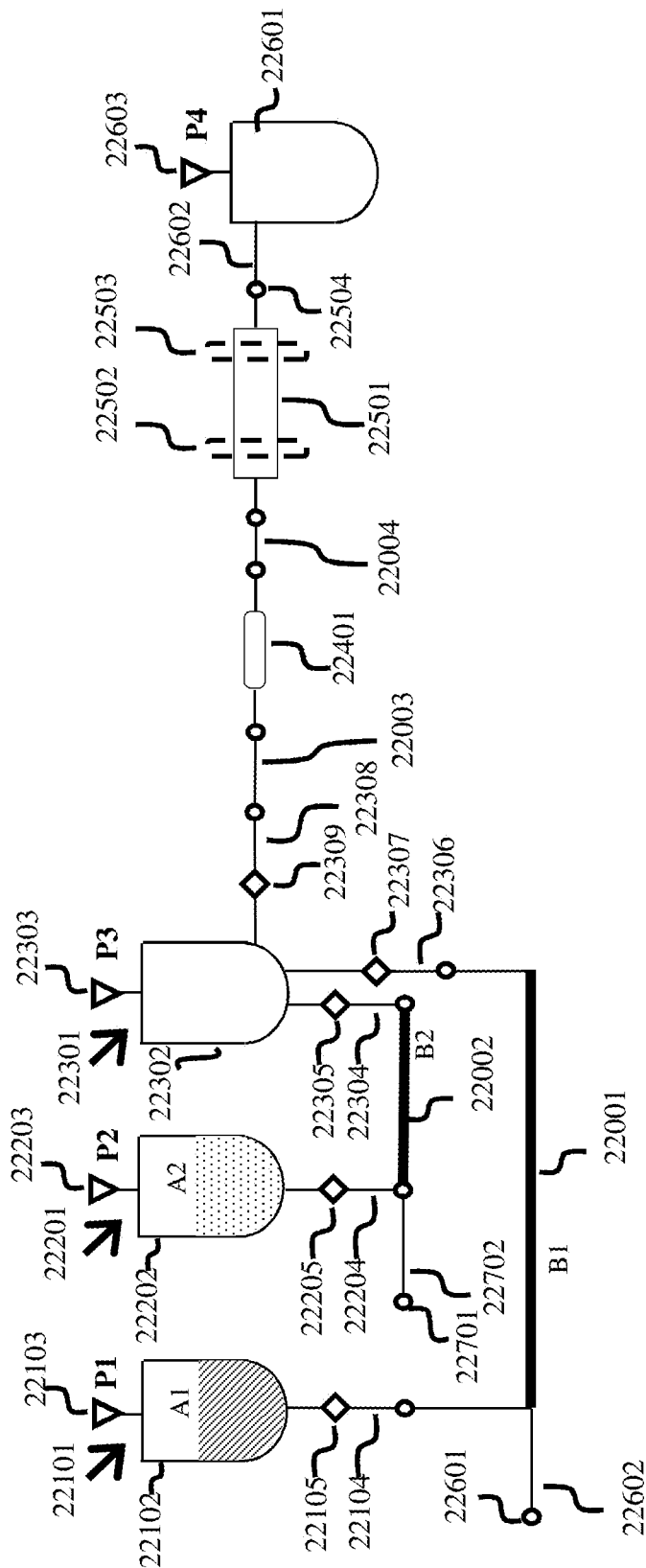

In some embodiments, a reagent A1 is loaded into the chamber 22102, and a reagent A2 is loaded into the chamber 22202. In some embodiments, the reagents A1 and A2 have predetermined volumes that are stored on-board in the fluidic cartridge. In some embodiment, the reagent A1 and A2 are loaded into the chamber before the following analysis. In some embodiments, the sample B1 has a predetermined volume that is collected in the fluid conduit 22001 and the sample B2 has a predetermined volume that is collected in the fluid conduit 22002. Various methods can be used to introduce the sample B1 and B2 into the fluidic conduit 22001 and 22002. In some embodiments, the sample B1 is introduced via an inlet port 22601 and a fluidic conduit 22602, and a valve 22603 is closed after introducing the sample, as shown in FIG. 22A. In some embodiments, the sample B2 is introduced via an inlet port 22701 and a fluidic conduit 22702, and a valve 22703 is closed after introducing the sample, as shown in FIG. 22A. In some embodiments, the sample B1 is introduced via an inlet port 22601 and a fluidic conduit 22602, and the inlet port 22602 is sealed by an external structure after introducing the sample as shown in FIG. 22B. In some embodiments, the sample B2 is introduced via an inlet port 22701 and a fluidic conduit 22702, and the inlet port 22602 is sealed by an external structure after introducing the sample as shown in FIG. 22B.

Figure 22C:
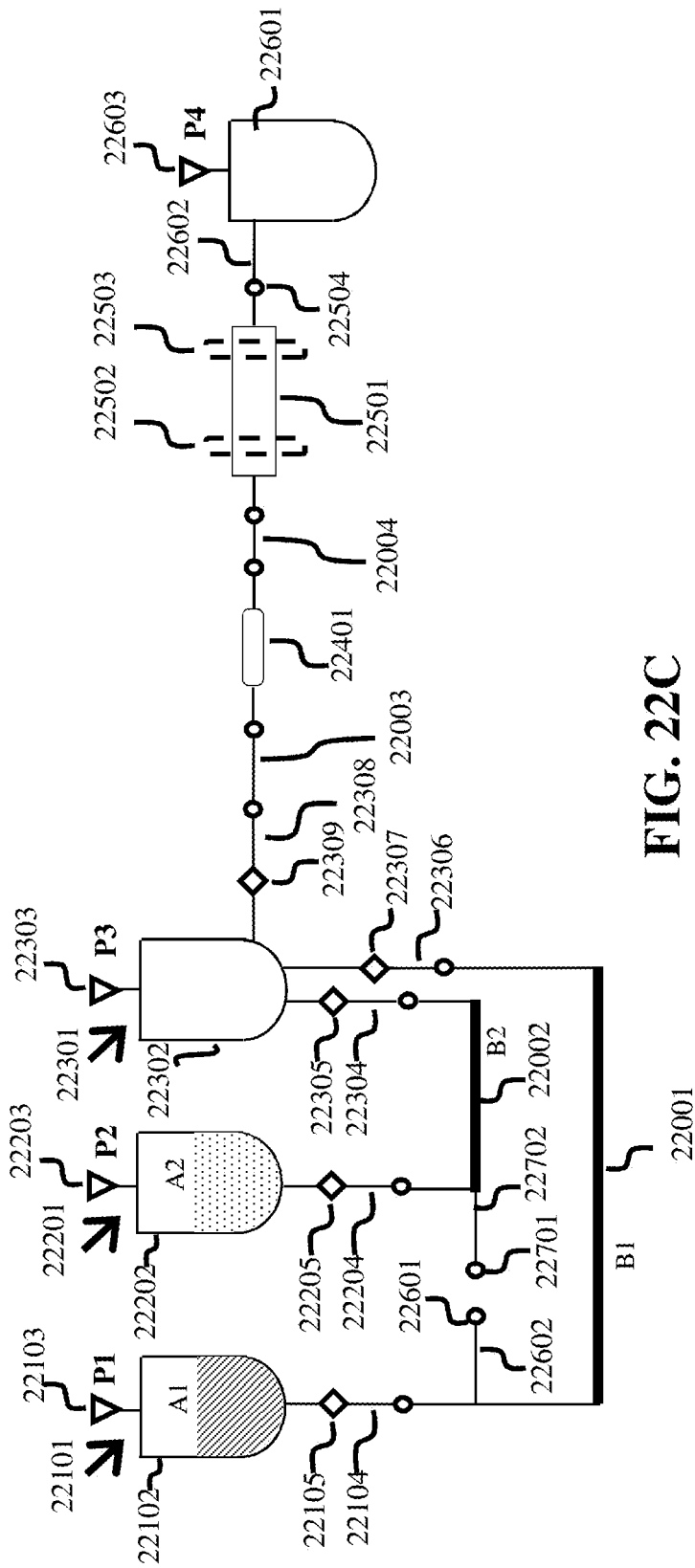

In some embodiments, a blood sample is introduced to the inlet ports 22601 and 22701 in two separate steps, as shown in FIG. 22A and FIG. 22B. The collected sample B1 is used for the leukocyte detections and the hemoglobin measurement, and B2 is used for the erythrocyte and platelet detections in the CBC as described herein. In some embodiments, a blood sample is introduced to the inlet ports 22601 and 22701 in one step. The collected sample B1 is used for the leukocyte detections and the hemoglobin measurement, and B2 is used for the erythrocyte and platelet detections in the CBC as described herein. In a non-limiting example, the inlet ports 22601 and 22701 are arranged in a close proximity as shown in FIG. 22C. A blood sample is applied to these two ports in one step and an external structure is used to seal these two ports in one step. In some embodiments, the inlet ports 22601 and 22701 are in a close proximity such that the distance between the ports are less than 0.5 mm, 1 mm, 2 mm, 5 mm, or 10 mm. Examples of the external structure include but are not limited to a mechanical cap, an adhesive seal, etc.

Figure 22D:
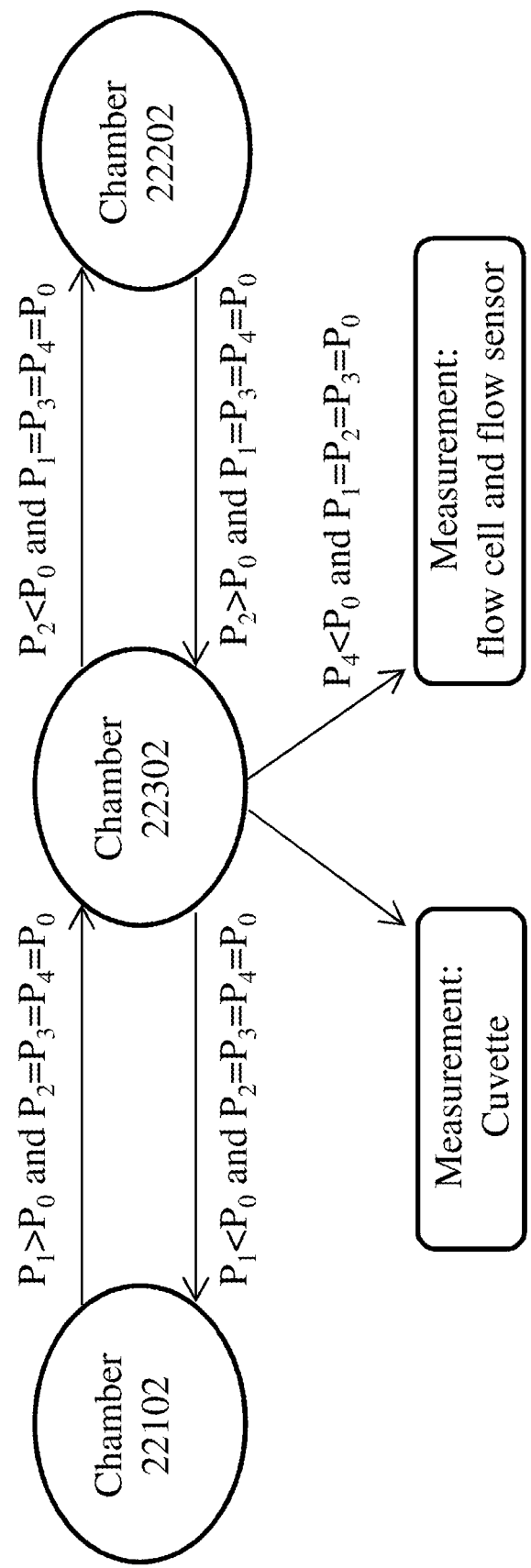

To transfer the fluid samples, in some embodiments, pneumatic pressures are applied to the venting ports 22103 ($P_1$), 22203 ($P_2$), and 22303 ($P_3$), and 22603 ($P_4$). FIG. 22D shows an exemplary diagram of the pneumatic pressures for the fluid transfer. By applying a pneumatic pressure ($P_1 > P_0$, $P_2 = P_3 = P_4 = P_0$), the reagent A1 is transferred from the chamber 22102 into the chamber 22302, and this action flushes the reagent A1 and sample B1 into the chamber 22302 to form the sample mixture 1. Next, by applying a pneumatic pressure ($P_4 < P_0$, $P_1 = P_2 = P_3 = P_0$), part or all of the sample mixture 1 is transferred into the flow cell and the flow sensor for the cytometer analysis. In some embodiments, any residual of the sample mixture 1 in the chamber 22302 can be transferred out the chamber, e.g. back into the chamber 22102 by applying ($P_1 < P_0$, $P_2 = P_3 = P_4 = P_0$), after the cytometer measurement. Similarly, by applying a pneumatic pressure ($P_2 > P_0$, $P_1 = P_3 = P_4 = P_0$), the reagent A2 is transferred from the chamber 22202 into the chamber 22302, and this action flushes the reagent A2 and the sample B2 into the chamber 22302 to form a sample mixture 2. By applying a pneumatic pressure ($P_4 < P_0$, $P_1 = P_2 = P_3 = P_0$), part or all of the sample mixture 2 is transferred into the flow cell and the flow sensor for the cytometer analysis. In some embodiments, any residual of the sample mixture 2 in the chamber 22302 can be transferred out the chamber, e.g. back into the chamber 22102 by applying ($P_2 < P_0$, $P_1 = P_3 = P_4 = P_0$), after the cytometer measurement. In some embodiments, the steps of forming and analyzing the sample mixture 1 are performed before the steps of forming and analyzing the sample mixture 2. In some embodiments, the steps of forming and analyzing the sample mixture 1 are performed after the steps of forming and analyzing the sample mixture 2. In some embodiment, the sample mixtures 1 or the sample mixture 2 or both are measured in the chamber 22302 for the cuvette measurement, or in an additional cuvette unit that is added in downstream of the channel 22308.

In some embodiment, the sample B1 is a whole blood and the reagent A1 is a reagent for the erythrocyte and platelet detection, while the sample B2 is a whole blood sample and the reagent A2 is a reagent for the leukocyte detection. Various examples of the leukocyte, erythrocyte and platelet detection reagents and the corresponding signals measured in the sheathless flow cell as described herein can be used herein. In some embodiments, the sample mixture 2 formed by the sample B2 and the reagent A2 is used for both the leukocyte detection and the measurement of hemoglobin concentration. Reagents and the corresponding signals for leukocyte count and the hemoglobin measurement are discussed above, and their various combinations that either keep the leukocyte intact or only release only part of the leukocyte cytoplasm can be used for the reagent A2. In certain embodiments, the leukocyte cells remain intact in the sample mixture 2, where the reagent A2 contains compounds/chemicals that lyse erythrocytes but not lyse the leukocyte cells, and the measurement of the sample mixture 2 in the flow cell detects at least one of the following signals, light scattering, fluorescence or electrical impedance. In some embodiments, reagent A2 contains at least one nucleic acid fluorescent dye that labels the nuclei of the leukocyte cell and the measurement of the sample mixture 2 in the flow cell at least measures the fluorescence signal from this dye labeling.

In a non-liming example, the reagent A1 is an erythrocyte and platelet detection reagent that contains a diluent with sphering compounds/chemicals, which dilutes the blood sample, keeps the erythrocyte cells and platelet cells intact, and transforms the erythrocyte cells into a sphere shape. The reagent A2 is a combination of the leukocyte and hemoglobin detection reagent, which contains compounds/chemicals that lyse erythrocyte cells to release the hemoglobin, but keeps the leukocyte cells intact. In some embodiments, the reagent A2 also contains a fluorescent nucleic acid dye for labeling the leukocyte cells. The sample B1 and B2 are whole blood with predetermined volumes. For the CBC testing, first, the reagent A1 and the sample B1 are transferred into the chamber 22302 to form the sample mixture 1. Part of all of the mixture 1 is measured in the sheathless flow cell for the erythrocyte count, platelet count, erythrocyte indices, or platelet indices, or a combination of these parameters. After this cytometer analysis, any residue of the mixture 1 in the chamber 22302 is removed from the chamber and transferred back into the chamber 22102. Next, the reagent A2 and the sample B2 are transferred into the third chamber 22302 to form the sample mixture 2. Part of the mixture 2 is measured in the sheathless flow cell for the leukocyte count, or leukocyte differential, or a combination of these parameters. Meanwhile, the sample mixture 2 is measured for the hemoglobin concentration by using the chamber 22302 as the cuvette. Any sample exiting the outlet 22504 of the flow sensor 22501 is collected in the reservoir 22601. In this way, the full CBC testing including the leukocyte count, leukocyte differential, erythrocyte count, platelet count, erythrocyte indices, platelet indices and the hemoglobin concentration can be obtained in the cartridge having the basic fluid unit, the sheathless flow cell and the flow sensor.

Figure 23A:
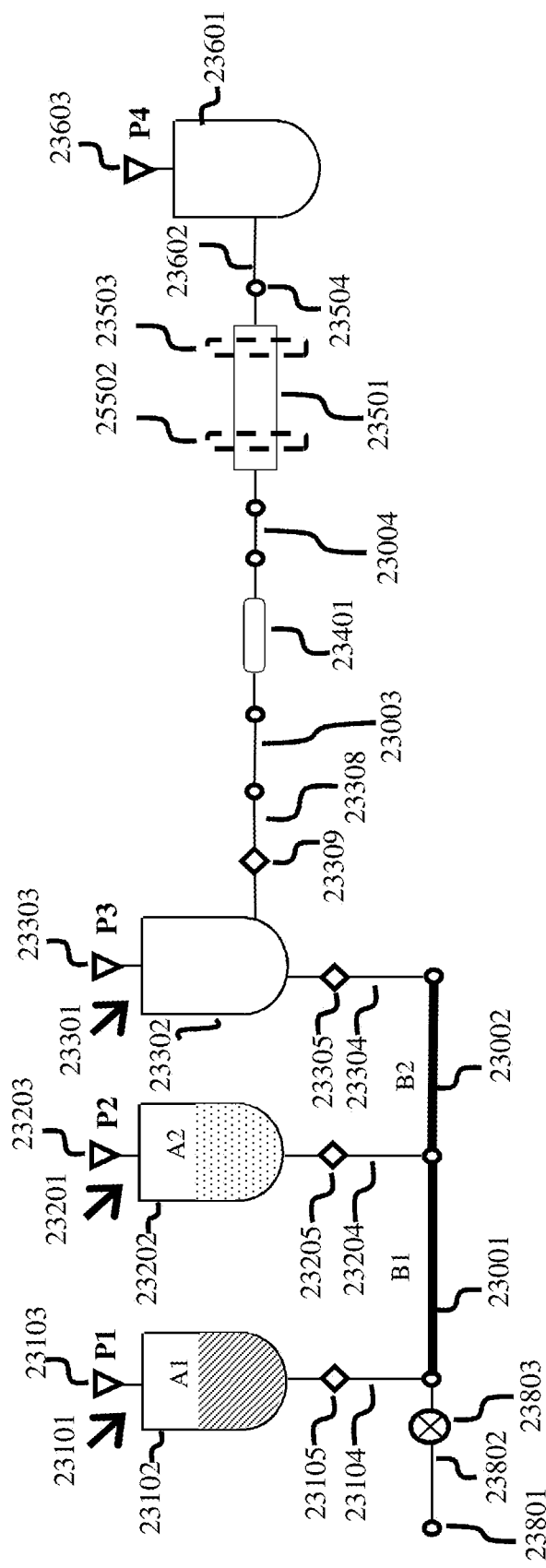

FIG. 23A shows another non-limiting example, which has three of the basic fluidic units 23101, 23201 and 23301, a sheathless flow cell 23401 and a flow sensor 23501. The basic fluidic unit 23101 has a chamber 23102, a venting port 23103 and a microfluidic channel 23104 with a valve 23105. The basic fluidic unit 23201 has a chamber 23202, a venting port 23203 and a microfluidic channel 23204 with a valve 23205. The basic fluidic unit 23301 has a chamber 23302, a venting port 23303 and two microfluidic channels 23304 with a valve 23305 and 22308 with a valve 22309. A fluid conduit 23001 connects the channel 23104 and 23204. A fluid conduit 23002 connects the channel 23204 and 23304. The inlet of the sheathless flow cell 23401 is connecting to the channel 22308 via a fluid conduit 23003. The outlet of the sheathless flow cell connects to the flow sensor 23501 via a fluidic conduit 23004. The flow sensor 23501 has two sensing zones 23502 and 23503. The outlet 23504 of the flow sensor 23501 is connected to a reservoir 23601 via a fluid conduit 23602. The reservoir 23601 has a venting port 23603. In some embodiments, the valves 23104 and 23205 are active valves that actuated by external means. Examples of the active valve include but not limit to the valve structures in FIGS. 19E-19G.

In some embodiments, a reagent A1 with a predetermined volume is loaded into the chamber 23102, and a reagent A2 with a predetermined volume is loaded into the chamber 23202. In some embodiments, the reagents A1 and A2 are stored on-board in the fluidic cartridge initially. In some embodiment, the reagent A1 and A2 are loaded into the chamber before the following analysis. In some embodiments, a blood sample B1 with a predetermined volume is collected in the fluid conduit 23001 and a blood sample B2 with a predetermined volume is collected in the fluid conduit 23002. Various methods can be used to introduce the sample B1 and B2 into the fluidic conduit 23001 and 23002. In some embodiments, the sample B1 and B2 is introduced via an inlet port 23801 and a fluidic conduit 23802, and a valve 22603 is closed after introducing the sample, as shown in FIG. 23A. In some other embodiments, the sample B1 and B2 is introduced via an inlet port 23801 and a fluidic conduit 23802, and the inlet port 23802 is sealed by an external structure after introducing the sample. Examples of the external structure include but are not limited to a mechanical cap, an adhesive seal, etc.

Figure 23B:
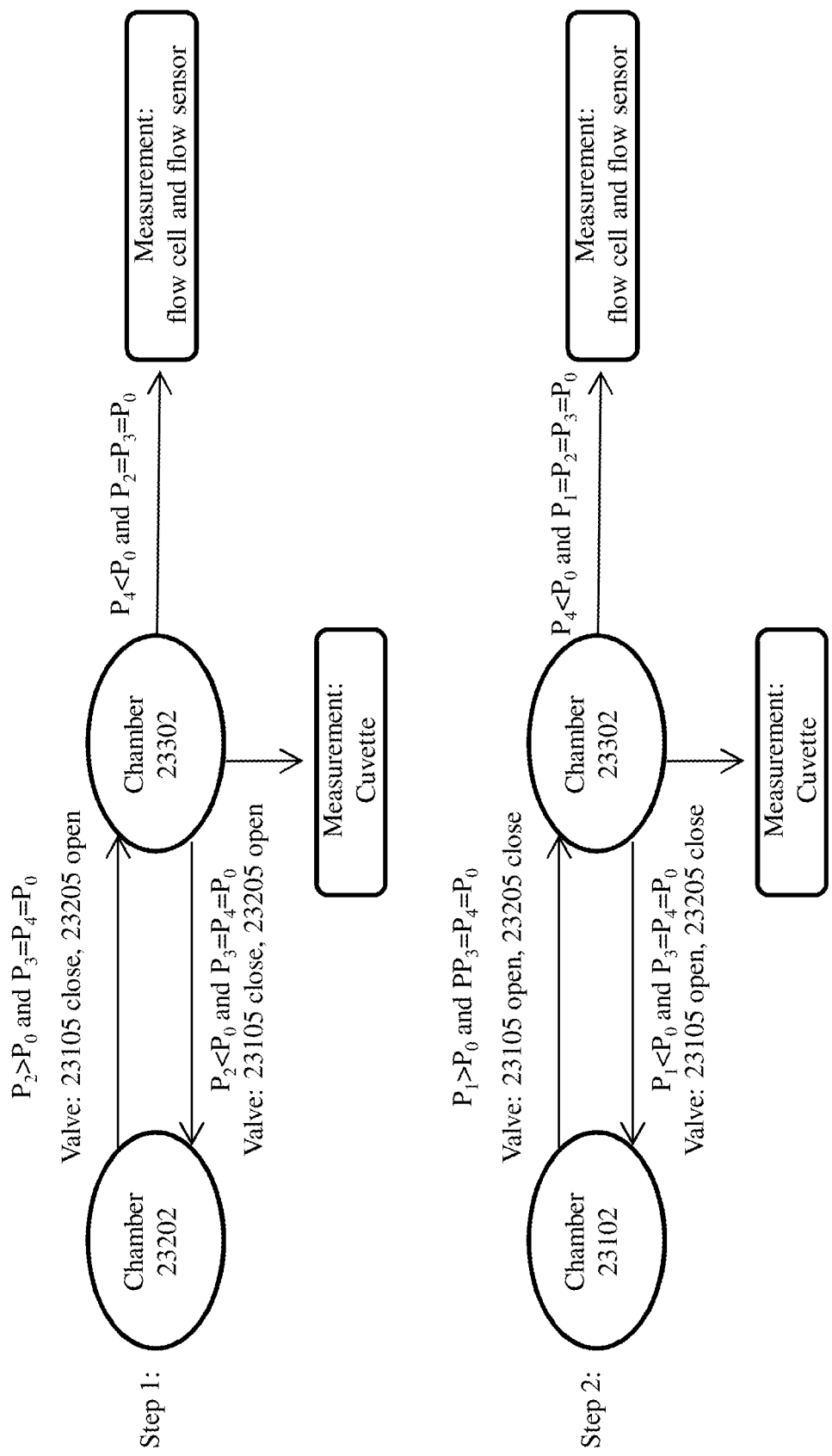

To transfer the fluid samples, in some embodiments, pneumatic pressures are applied to the venting ports 23103 ($P_1$), 23203 ($P_2$), and 23303 ($P_3$), and 23603 ($P_4$), and the active valves 23105 and 23205 are actuated between the close status and the open status. FIG. 23B shows an exemplary diagram of the pneumatic pressures and the active valve actuation for the fluid transfer. In Step 1, the valve 23105 is kept in the close status and the valve 23205 is kept in the open status. By applying a pneumatic pressure ($P_2>P_0$, $P_3=P_4=P_0$), the reagent A2 is transferred from the chamber 23202 into the chamber 23302, and this action flushes the reagent A2 and sample B2 into the chamber 23302 to form the sample mixture 2. In some embodiments, the pneumatic pressure ($P_2<P_0$, $P_3=P_4=P_0$) and ($P_2>P_0$, $P_3=P_4=P_0$) are used in sequential to move the sample mixture 2 from the chamber 23302 into the chamber 23202 and then back into the chamber 23302 again to enhance the mixing as described herein. Next, by applying a pneumatic pressure ($P_4<P_0$, $P_2=P_3=P_0$), part or all of the sample mixture 2 is transferred into the flow cell and the flow sensor for the cytometer analysis. In some embodiments, the chamber 23302 is used as the cuvette for hemoglobin measurement of the sample mixture 2. In some embodiments, any residual of the sample mixture 2 in the chamber 23302 can be transferred out the chamber, e.g. back into the chamber 23202 by applying ($P_2<P_0$, $P_3=P_4=P_0$), after the cytometer measurement. In Step 2, the valve 22105 is kept in open status and the valve 23205 is kept in close status. By applying a pneumatic pressure ($P_1>P_0$, $P_3=P_4=P_0$), the reagent A1 is transferred from the chamber 23102 into the chamber 23302, and this action flushes the reagent A1 and the sample B1 into the chamber 23302 to form a sample mixture 1. In some embodiments, the pneumatic pressure ($P_1<P_0$, $P_3=P_4=P_0$) and ($P_1>P_0$, $P_3=P_4=P_0$) are used in sequential to move the sample mixture 1 from the chamber 23302 into the chamber 23102 and then back into the chamber 23302 again to enhance the mixing as described herein. Next, by applying a pneumatic pressure ($P_1<P_0$, $P_1=P_3=P_0$), part or all of the sample mixture 1 is transferred into the flow cell and the flow sensor for the cytometer analysis. In some embodiments, the chamber 23302 is used as the cuvette for hemoglobin measurement of the sample mixture 1. In some embodiments, a cuvette unit can be added in downstream of the channel 23308 via a fluidic conduit for the cuvette measurement.

In some embodiment, the sample B2 is a whole blood and the reagent A2 is a reagent for the erythrocyte and platelet detection, while the sample B1 is a whole blood sample and the reagent A1 is a reagent for the leukocyte detection. Various examples of the leukocyte, erythrocyte and platelet detection reagents and the corresponding signals measured in the sheathless flow cell as described herein can be used herein. In some embodiments, the sample mixture 1 formed by the sample B1 and the reagent A1 is used for both the leukocyte detection and the measurement of hemoglobin concentration. Reagents and the corresponding signals for leukocyte count and the hemoglobin measurement are discussed above, and their various combinations that either keep the leukocyte intact or only release only part of the leukocyte cytoplasm can be used for the reagent A1. In certain embodiments, the leukocyte cells remain intact in the sample mixture 1, where the reagent A1 contains compounds/chemicals that lyse erythrocytes but not lyse the leukocyte cells, and the measurement of the sample mixture 1 in the flow cell detects at least one of the following signals, light scattering, fluorescence or electrical impedance. In some embodiments, reagent A1 contains at least one nucleic acid fluorescent dye that labels the nuclei of the leukocyte cell and the measurement of the sample mixture 1 in the flow cell at least measures the fluorescence signal from this dye labeling.

In a non-liming example, the reagent A2 is erythrocyte detection reagent that contains a diluent with sphering compounds/chemicals, which dilute a blood sample, keeps the erythrocyte cells and platelet cells intact, and transforms the erythrocyte cells into a sphere shape. The reagent A1 is a combination of the leukocyte and hemoglobin detection reagents, which contains compounds/chemicals that lyse the erythrocyte cells to release the hemoglobin, but keeps the leukocyte cells intact. In some embodiments, the reagent A1 also contains a fluorescent nucleic acid dye for labeling the leukocyte cells. The sample B1 and B2 are whole blood with predetermined volumes. For the CBC testing, in Step 1, the valve 23105 is kept at the close status and the valve 23205 is kept at the open status. The reagent A2 and the sample B2 are transferred into the chamber 23302 to form the sample mixture 2. Part of all of the mixture 2 is measured in the sheathless flow cell for the erythrocyte count, platelet count, erythrocyte indices, or platelet indices, or a combination of these parameters. After the cytometer analysis, any residue of the mixture 2 in the chamber 23302 is removed from the chamber and transferred back into the chamber 23202. In some embodiments, a light absorption measurement is made on the sample mixture 2 using the chamber 23303 as the cuvette. In Step 2, the valve 23105 is kept at the open status and the valve 23205 is kept at the close status. Next, the reagent A1 and the sample B1 are transferred into the chamber 22302 to form the sample mixture 1. Part of the mixture 1 is measured in the sheathless flow cell for the leukocyte count, or leukocyte differential, or a combination of these parameters. Meanwhile, the mixture 1 in the third chamber 23302 is measured for the hemoglobin concentration by using the chamber 23302 as the cuvette. Any sample exiting the outlet 23504 of the flow sensor 23501 is collected in the reservoir 23601. In this way, the full CBC testing including the leukocyte count, leukocyte differential, erythrocyte count, platelet count, erythrocyte indices, platelet indices and the hemoglobin concentration can be obtained in the cartridge having the basic fluid unit, the sheathless flow cell and the flow sensor.

Figure 24A:
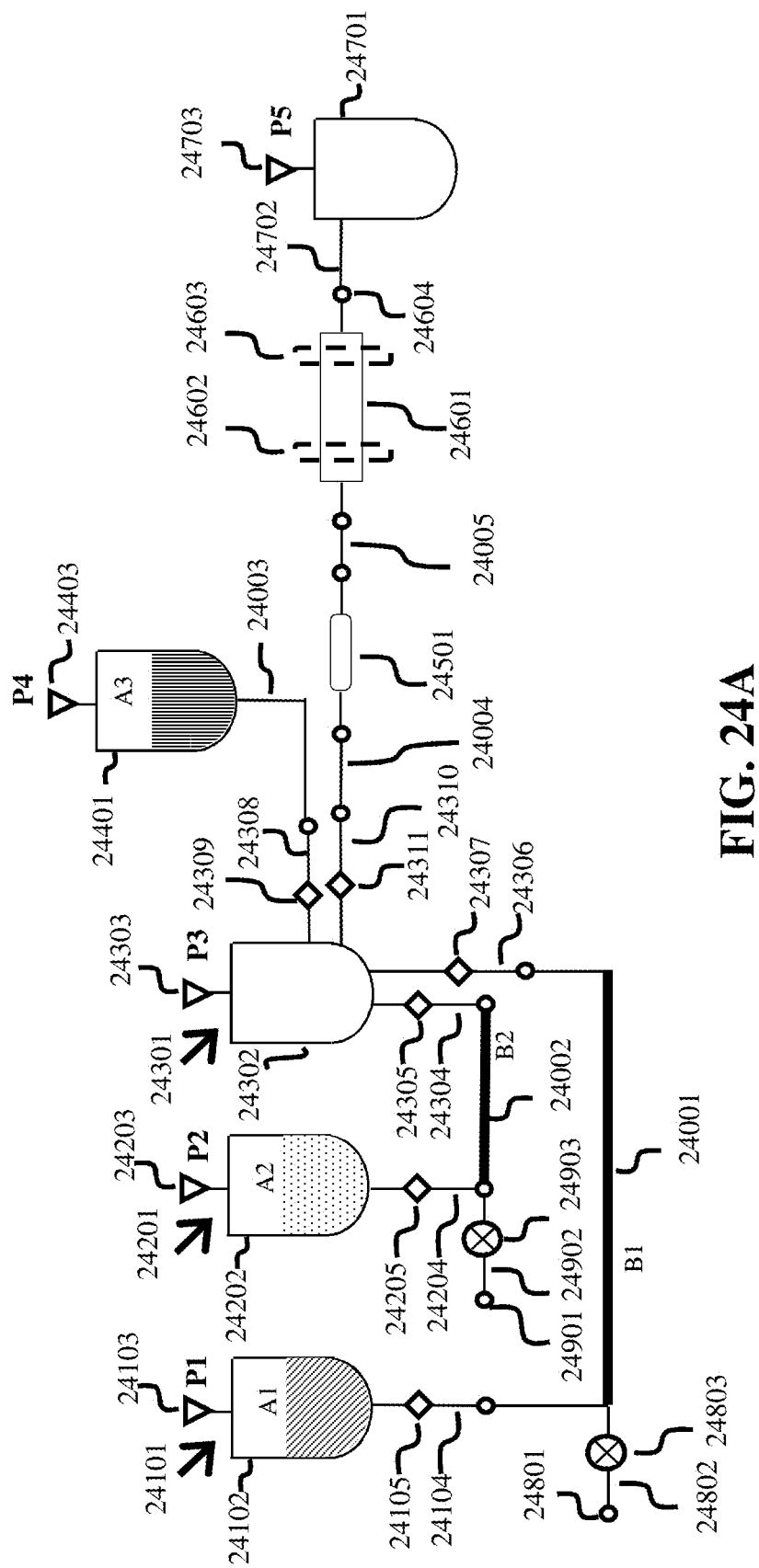

FIG. 24A shows another non-limiting example, which has three of the basic fluidic units 24101, 24201 and 24301, a sheathless flow cell 24501 and a flow sensor 24601. The basic fluidic unit 24101 has a chamber 24102, a venting port 24103 and a microfluidic channel 24104 with a valve 24105. The basic fluidic unit 24201 has a chamber 24202, a venting port 24203 and a microfluidic channel 24204 with a valve 24205. The basic fluidic unit 24301 has a chamber 24302, a venting port 24303 and four microfluidic channels 24304 with a valve 24305, 24306 with a valve 24307, 22308 with a valve 22309, and 24310 with a valve 24311. A reservoir chamber 24401 with a venting port 24403 is connected to the channel 24308 with a fluid conduit 24003. A fluid conduit 24001 connects the channel 24104 and 24306. A fluid conduit 24002 connects the channel 24204 and 24304. The inlet of the sheathless flow cell 24501 is connecting to the channel 24310 via a fluid conduit 24004. The outlet of the sheathless flow cell connects to the flow sensor 24601 via a fluidic conduit 24005. The flow sensor 24601 has two sensing zones 24602 and 24603. The outlet 24604 of the flow sensor 24601 is connected to a reservoir 24701 via a fluid conduit 24702. The reservoir 24701 has a venting port 24703.

In some embodiments, a reagent A1 with a predetermined volume is loaded into the chamber 24102, and a reagent A2 with predetermined volume is loaded into the chamber 24202, a reagent A3 with a predetermined volume is loaded into the reservoir chamber 24401. In some embodiments, the reagents A1 and A2 and A3 are initially stored on-board in the fluidic cartridge. In some embodiment, the reagent A1 and A2 and A3 are loaded into the chamber before the following analysis. In some embodiments, the reagent A3 is a dried reagent. Non-limiting examples of the dried reagent can be stored as dried beads, dried powder, or dried coating layers. In some embodiments, a sample B1 with a predetermined volume is collected in the fluid conduit 24001 and a sample B2 with a predetermined volume is collected in the fluid conduit 24002. Various methods can be used to introduce the sample B1 and B2 into the fluidic conduit 24001 and 24002 as described in above examples. In a non-limiting example, as shown in FIG. 24A, the sample B1 is introduced via an inlet port 24801 and a fluidic conduit 24802, and a valve 24803 is closed after introducing the sample. The sample B2 is introduced via an inlet port 24901 and a fluidic conduit 24902, and a valve 24903 is closed after introducing the sample.

Figure 24B:
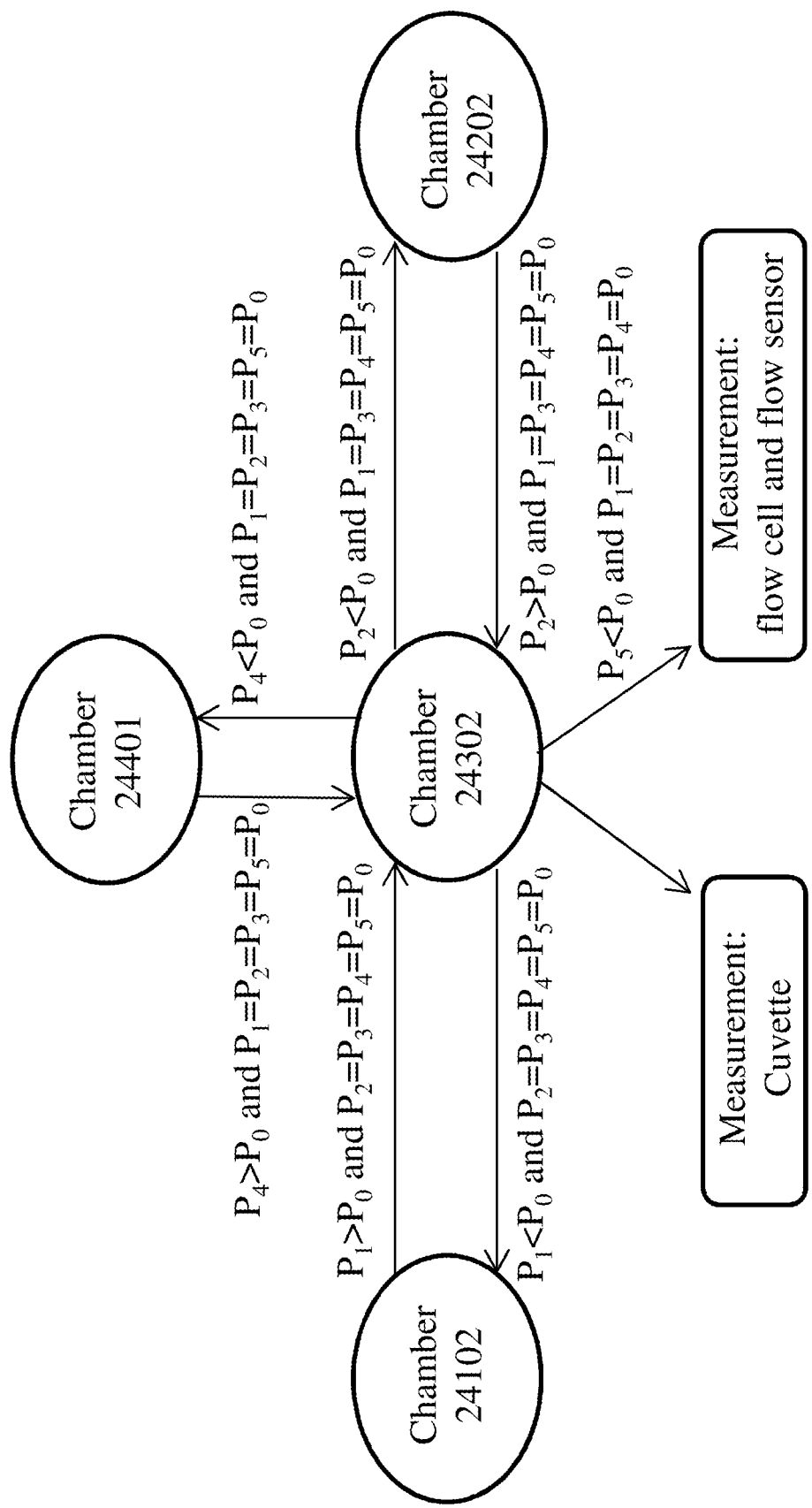

To transfer the fluid samples, in some embodiments, pneumatic pressures are applied to the venting port 24103 ($P_1$), 24203 ($P_2$), 24303 ($P_3$) and 24403 ($P_4$), and 24703 ($P_5$). FIG. 24B shows an exemplary diagram of using this fluidic configuration. By applying a pneumatic pressure ($P_1 > P_0$, $P_2 = P_3 = P_4 = P_5 = P_0$), the reagent A1 is transferred from the chamber 24102 into the chamber 24302, and this action flushes the reagent A1 and sample B1 into the chamber 24302 to form a sample mixture 1. By applying a pneumatic pressure ($P_5 < P_0$, $P_1 = P_2 = P_3 = P_4 = P_0$), part or all of the sample mixture 1 is transferred into the flow cell and the flow sensor for the cytometer analysis. In some embodiments, any residual of the sample mixture 1 in the chamber 24302 can be transferred out of the chamber 24302, e.g. back into the chamber 24102, after the cytometer measurement. Similarly, by applying a pneumatic pressure ($P_2 > P_0$, $P_1 = P_3 = P_4 = P_5 = P_0$), the reagent A2 is transferred from the chamber 24202 into the chamber 24302, and this action flushes the reagent A2 and sample B2 into the chamber 24302 to form a sample mixture 2. By applying a pneumatic pressure ($P_5 < P_0$, $P_1 = P_2 = P_3 = P_4 = P_0$), part or all of the sample mixture 2 is transferred into the flow cell and the flow sensor for the cytometer analysis. In some embodiments, by applying a pneumatic pressure ($P_4 < P_0$, $P_1 = P_2 = P_3 = P_5 = P_0$), part or all of the sample in the chamber 24302, either the sample mixture 1 or the sample mixture 2, can be transferred into the reservoir chamber 24401 to mix with the reagent A3 and forms a sample mixture 3. In some embodiment, the sample mixture 1, 2, and 3 are measured for the hemoglobin concentration, respectively. The measurement of the hemoglobin centration is carried out by using the chamber 24302 as the cuvette, or by adding a cuvette unit in downstream of the channel 24310.

In some embodiment, the sample B1 is a whole blood and the reagent A1 is a reagent for the erythrocyte and platelet detection, while the sample B2 is a whole blood sample and the reagent A2 is a reagent for the leukocyte detection. Various examples of the leukocyte, erythrocyte and platelet detection reagents and the corresponding signals measured in the sheathless flow cell as described herein can be used herein. In some embodiments, the reagent A3 is a reagent for hemoglobin concentration. Various examples of the hemoglobin detection reagents and the corresponding signals as described herein can be used herein. In some embodiments, this reagent A3 is a dried reagent that is initially stored on-board in the fluidic cartridge. In some embodiments, the dried reagent A3 is coated as a layer on the inner surface of the chamber 24401, and dissolves upon contact with a fluid sample.

In a non-liming example, the reagent A1 is erythrocyte and platelet detection reagent that contains a diluent with sphering compounds/chemicals, which dilutes a blood sample, keeps the erythrocyte cells and platelet cells intact, and transforms the erythrocyte cells into a sphere shape. The reagent A2 is a leukocyte detection reagent that contains at least a fluorescent nucleic acid dye. The reagent A3 is a hemoglobin detection reagent that lyses the erythrocyte cells, releases the hemoglobin and converts the hemoglobin into a stabilized form for measurements. The reagent A3 is coated as a dried layer on the surface of the reservoir chamber 24401. For the CBC testing, first, the reagent A1 and the sample B1 are transferred into the chamber 24302 to form the sample mixture 1. Part of all of the mixture 1 is measured in the sheathless flow cell for the erythrocyte count, platelet count, erythrocyte indices, or platelet indices, or a combination of these parameters. After this cytometer analysis, any residue of the mixture 1 in the chamber 24302 is removed from the chamber and transferred back into the first chamber 24102. Next, the reagent A2 and the sample B2 are transferred into the chamber 24302 to form the sample mixture 2. Part of the mixture 2 is measured in the sheathless flow cell for the leukocyte count, or leukocyte differential, or a combination of these parameters. Next, part or all of the reaming sample mixture 2 in the chamber 24302 is transferred into the reservoir chamber 24401. The dried coating layer of the reagent 3 dissolve upon in contact with sample mixture 2, and mix with it to form the sample mixture 3. The sample mixture 3 is then measured for the hemoglobin concentration by using either the reservoir chamber 24401 or the chamber 24302 as the cuvette, or by using an additional cuvette unit in the downstream of the channel 24310. In this way, the full CBC testing including the leukocyte count, leukocyte differential, erythrocyte count, platelet count, erythrocyte indices, platelet indices and the hemoglobin concentration can be obtained in the cartridge having the basic fluid unit, the sheathless flow cell and the flow sensor.

In some embodiments, the cartridge having the sheathless flow cells is inserted into a reader instrument having optics to measure the signals (e.g. fluorescence, light forward scattering, light side scattering, light absorption, etc.) from a sample in the flow cell. The alignment of the cartridge, e.g. the relative positioning between the flow cell and the optics, impacts the signals measured for the cytometer analysis. To compensate this alignment, some embodiments of the cartridge contain at least a reagent with micro beads of predetermined properties (e.g. bead size, concentration of fluorophore, etc.) as a calibration standard. For non-limiting examples, the micro beads can be in a reagent for the erythrocyte and platelet detection, a reagent for the leukocyte detection, or a separated reagent for the calibration purpose. The sizes of the micro beads can be in the range of 0.1-1, 1-2, 2-6, 6-8, 8-10, 10-15, 25-30, 30-50, or 50-100 μm, and should be smaller than the diameter the of sheathless flow cell.

In some embodiments, the cartridge contains at least a reagent having micro beads with predetermined size as a calibration standard to quantify the cell sizes. In a non-limiting example, a reagent for the erythrocyte and platelet detection contains micro beads with pre-determined sizes, and the mixture of the reagent and a blood sample is measured in the sheathless flow cell for at least a light scattering signal. FIG. 9D shows a non-limiting example of the recorded light scattering signal from the mixture of the reagent and a blood sample. In this example, the peak height in the recorded signal indicates the size of the detected beads or cells. The sizes of the erythrocyte cells or the platelet cells are quantified by three factors: first, the measured peak heights of the erythrocyte or the platelet cells, respectively; second, the measured peak heights of the micro beads; and third, the pre-determined size of the micro beads. In some other embodiment, the sizes of the detected beads or cells are characterized by other signal properties such as peak width, time-of-flight, etc. Non-limiting examples of these signal properties and their measurement are described in the U.S. Pat. No. 4,765,737.

In a non-limiting example, the cartridge device comprises a reagent, and the reagent comprises size reference beads having a uniform size of 10 μm in diameter. In this example, the size of the reference beads (10 μm in diameter) is larger than erythrocyte cells (about 7 μm in diameter) and platelet cells (about 2 μm in diameter). Light scattering with a forward angle can be measured by the reader instrument device to distinguish the size reference beads from erythrocyte cells and/or platelet cells in a sample stream, and the light scattering signal is further used to quantify the size of erythrocyte cells and/or platelet cells in reference to the size reference beads.

In another non-limiting example, the cartridge device comprises a reagent, and the reagent comprises fluorescent size reference beads having a uniform size of 5 μm in diameter. The fluorescent size reference beads are labeled with fluorescent dyes emitting fluorescence that is distinct from the fluorescence of erythrocyte cells and/or platelet cells. The reader instrument device is configured to detect both fluorescence and light scattering with a forward angle. The fluorescence signal is used to distinguish the size reference beads from erythrocyte cells and/or platelet cells, and the light scattering signal is used to quantify the size of erythrocyte cells and/or platelet cells in reference to the size reference beads.

In some embodiment, the cartridge contains at least a reagent having micro beads with predetermined fluorophore concentration as a calibration standard for quantify the fluorescence emission intensity of target cells. In a non-limiting example, the reagent for the erythrocyte and platelet detection contains fluorescent micro beads with predetermined fluorophore concentration. FIG. 9E shows a non-limiting example of the recorded signals from the mixture of the reagent and a blood sample, which detects at least a fluorescence signal. Peak heights of the fluorescence signals measured from the beads are then used as a calibration standard to quantity the fluorescence intensity of target cells. For non-limiting examples, they can be used to quantity the fluorescence intensity of the erythrocyte cells, the platelet cell, or the leukocyte cells.

In some embodiment, the cartridge contains at least a reagent having micro beads with either predetermined size or fluorophore concentration as a calibration standard to evaluate the alignment between the flow cell in the cartridge and the optics in the reader instrument. In a non-limiting example, a reagent for the erythrocyte and platelet detection contains micro beads with pre-determined sizes, and the mixture of the reagent and a blood sample is measured in the sheathless flow cell for at least a light scattering signal. FIG. 9D shows a non-limiting example of the recorded light scattering signal from the mixture of the reagent and a blood sample. In this example, the peak heights of the detected beads in the recorded signal are used to evaluate the alignment between the flow cell and the optics. When the peak heights of the beads are higher than a predetermined threshold, the alignment is considered satisfactory. When the peak heights of the beads are lower than a predetermined threshold, the alignment is considered unsatisfactory.

Many variations and alternative elements have been disclosed in embodiments of the present disclosure. Still further variations and alternate elements will be apparent to one of skill in the art. Among these variations, without limitation, are the selection of fluidic units, components and structures for the inventive devices and methods, and the samples that may be analyzed therewith. Various embodiments of the disclosure can specifically include or exclude any of these variations or elements.

In some embodiments, the numbers expressing quantities of ingredients, properties such as concentration, reaction conditions, and so forth, used to describe and claim certain embodiments of the disclosure are to be understood as being modified in some instances by the term "about." As one non-limiting example, one of ordinary skill in the art would generally consider a value difference (increase or decrease) no more than 10% to be in the meaning of the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the disclosure are approximations, the numerical values set forth in the specific examples are reported as precisely as practicable. The numerical values presented in some embodiments of the disclosure may contain certain errors necessarily resulting from the standard deviation found in their respective testing measurements.

Groupings of alternative elements or embodiments of the disclosure disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The disclosure is explained by various examples, which are intended to be purely exemplary of the disclosure, and should not be considered as limiting the disclosure in any way. Various examples are provided to better illustrate the claimed disclosure and are not to be interpreted as limiting the scope of the disclosure. To the extent that specific materials are mentioned, it is merely for purposes of illustration and is not intended to limit the disclosure. One skilled in the art may develop equivalent means or reactants without the exercise of inventive capacity and without departing from the scope of the disclosure.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the disclosure are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the disclosure known to the applicant at this time of filing the application has been presented and is intended for the purposes of illustration and description. The present description is not intended to be exhaustive nor limit the disclosure to the precise form disclosed and many modifications and variations are possible in the light of the above teachings. The embodiments described serve to explain the principles of the disclosure and its practical application and to enable others skilled in the art to utilize the disclosure in various embodiments and with various modifications as are suited to the particular use contemplated. Therefore, it is intended that the disclosure not be limited to the particular embodiments disclosed for carrying out the disclosure.

While particular embodiments of the present disclosure have been shown and described, it will be obvious to those skilled in the art that, based upon the teachings herein, changes and modifications may be made without departing from this disclosure and its broader aspects and, therefore, the appended claims are to encompass within their scope all such changes and modifications as are within the true spirit and scope of this disclosure.

Additional Aspects of the Present Disclosure

Aspects of the subject matter described herein may be useful alone or in combination with any one or more of the other aspect described herein. Without limiting the foregoing description, in a first aspect of the present disclosure, a device for analyzing blood cells in a sample, comprising: a cartridge device, wherein the cartridge device comprises: a fluidic conduit configured for receiving the sample into the cartridge device; a chamber fluidly connected to the fluidic conduit and configured for mixing at least a portion of the sample with at least of a portion of a reagent to form one or more sample mixtures; and a flow cell fluidly connected to the chamber and configured for forming one or more sample streams from the one or more sample mixtures; and a reader instrument device configured for receiving the cartridge device, measuring one or a plurality of signals from the sample streams in the flow cell, and analyzing the blood cells in the sample.

In accordance with a second aspect of the present disclosure, which may be used in combination with any other aspect or combination of aspects listed herein, the reader instrument device is configured for detecting, identifying, characterizing, quantifying, and/or numerating leukocyte cells, erythrocyte cells, or platelet cells, or a combination thereof.

In accordance with a third aspect of the present disclosure, which may be used in combination with any other aspect or combination of aspects listed herein, the cartridge device is configured for forming the sample streams in the flow cell without a sheath flow.

In accordance with a fourth aspect of the present disclosure, which may be used in combination with any other aspect or combination of aspects listed herein, the flow cell has a width in the range of about 1-10, 10-40, 40-100, or 100-200 μm; and a depth in the range of about 1-10, 10-40, 40-100, or 100-200 μm.

In accordance with a fifth aspect of the present disclosure, which may be used in combination with any other aspect or combination of aspects listed herein, the flow cell has a length in the range of about 1-10, 10-100, 100-1,000, 1,000-5,000 μm, or 5,000-10,000 μm.

In accordance with a sixth aspect of the present disclosure, which may be used in combination with any other aspect or combination of aspects listed herein, the flow cell comprises a transparent surface for an optical signal from the sample streams in the flow cell; and wherein the reader instrument device is configured for measuring the optical signal.

In accordance with a seventh aspect of the present disclosure, which may be used in combination with any other aspect or combination of aspects listed herein, the optical signal comprises light scattering, light absorption, light extinction, or fluorescence, or a combination thereof.

In accordance with an eighth aspect of the present disclosure, which may be used in combination with any other aspect or combination of aspects listed herein, the chamber has a volume in the range of about 0.01-0.1 ml, 0.1-0.2 ml, 0.2-0.4 ml, 0.4-0.8 ml, 0.8-2 ml, or 2-10 ml.

In accordance with a ninth aspect of the present disclosure, which may be used in combination with any other aspect or combination of aspects listed herein, the chamber comprises a venting port configured for receiving a pneumatic pressure source.

In accordance with a tenth aspect of the present disclosure, which may be used in combination with any other aspect or combination of aspects listed herein—when the cartridge device is in use, the chamber is so positioned that at least a portion of the fluid inside the chamber is pulled by gravity away from the venting port and/or towards the lower bottom of the chamber.

In accordance with an eleventh aspect of the present disclosure, which may be used in combination with any other aspect or combination of aspects listed herein, the cartridge device further comprises a cuvette; and wherein the reader instrument device is configured for measuring a signal from the sample mixtures in the cuvette to determine the hemoglobin concentration in the sample.

In accordance with a twelfth aspect of the present disclosure, which may be used in combination with any other aspect or combination of aspects listed herein, the reader instrument device is configured for measuring a light absorption signal from the sample mixtures in the cuvette to determine the hemoglobin concentration in the sample.

In accordance with a thirteenth aspect of the present disclosure, which may be used in combination with any other aspect or combination of aspects listed herein, the reagent comprises an osmolality-adjusting compound for forming sample mixtures with an osmolality in the range of about 140-160, 160-180, 180-200, 200-220, 220-240, 240-260, 260-280, 280-300, 300-320, 320-340, 340-360, 360-380, or 380-400 mOsm/L.

In accordance with a fourteenth aspect of the present disclosure, which may be used in combination with any other aspect or combination of aspects listed herein, the reagent comprises a sphering compound for transforming erythrocyte cells from disk shape into sphere shape.

In accordance with a fifteenth aspect of the present disclosure, which may be used in combination with any other aspect or combination of aspects listed herein, the reagent comprises a fluorescent labeling reagent for labeling nucleic acids in blood cells in the sample mixtures; and wherein the reader instrument device is configured for measuring a fluorescence signal from the sample streams in the flow cell.

In accordance with a sixteenth aspect of the present disclosure, which may be used in combination with any other aspect or combination of aspects listed herein, the reagent comprises a lysing compound for lysing erythrocyte cells in the sample mixtures to release hemoglobin.

In accordance with a seventeenth aspect of the present disclosure, which may be used in combination with any other aspect or combination of aspects listed herein, the cartridge device further comprises a flow sensor fluidly connected to the flow cell; and wherein the reader instrument device is configured for measuring a sensing signal from the flow sensor when the sample streams enter the flow sensor.

In accordance with an eighteenth aspect of the present disclosure, which may be used in combination with any other aspect or combination of aspects listed herein, the reader instrument device is configured for using the sensing signal from the flow sensor to determine the absolute count of the blood cells in the sample.

In accordance with a nineteenth aspect of the present disclosure, which may be used in combination with any other aspect or combination of aspects listed herein, the measured sensing signal comprises an optical signal.

In accordance with a twentieth aspect of the present disclosure, which may be used in combination with any other aspect or combination of aspects listed herein, the fluidic connection between the flow cell and the flow sensor is configured for a sample stream to have the same flow rate flowing through the flow cell and the flow sensor In accordance with a twenty-first aspect of the present disclosure, which may be used in combination with any other aspect or combination of aspects listed herein, the flow sensor comprises a fluidic channel and a sensing zone on the fluidic channel, wherein the fluidic channel is fluidly connected to the flow cell to allow the sample streams to flow through; and wherein the reader instrument device is configured for measuring a sensing signal from the sensing zone when the sample streams enter the sensing zone.

In accordance with a twenty-second aspect of the present disclosure, which may be used in combination with any other aspect or combination of aspects listed herein, a device as disclosed herein further comprises a microfluidic channel fluidly connected to the chamber and a valve on the microfluidic channel, wherein the microfluidic channel has a cross section in the range of about 0.001-0.01 mm$^2$, 0.01-0.1 mm$^2$, 0.1-0.25 mm$^2$, 0.25-0.5 mm$^2$, 0.5-1 mm$^2$, 1-2 mm$^2$, or 2-10 mm$^2$.

In accordance with a twenty-third aspect of the present disclosure, which may be used in combination with any other aspect or combination of aspects listed herein, the valve is a passive valve that comprises one of the following structures: (i) a patch of hydrophobic surface in a channel having a hydrophilic surface, (ii) a patch of hydrophilic surface in a channel having a hydrophobic surface, (iii) an enlargement of the channel cross section along the flow direction in a channel having a hydrophilic surface, and (iv) a contraction of the channel cross section along the flow direction in a channel having a hydrophobic surface.

In accordance with a twenty-fourth aspect of the present disclosure, which may be used in combination with any other aspect or combination of aspects listed herein, the reader instrument device is configured for applying an actuation mechanism to control the fluid transfer in the cartridge device, and wherein the actuation mechanism comprises a pneumatic pressure source.

In accordance with a twenty-fifth aspect of the present disclosure, which may be used in combination with any other aspect or combination of aspects listed herein, the applied pneumatic pressure source actuates the cartridge device to transfer the sample mixtures from the chamber into the flow cell to form the sample streams.

In accordance with a twenty-sixth aspect of the present disclosure, which may be used in combination with any other aspect or combination of aspects listed herein, the cartridge device is configured for mixing two separate portions of the sample received in the fluidic conduit with the reagent to form two separate sample mixtures.

In accordance with a twenty-seventh aspect of the present disclosure, which may be used in combination with any other aspect or combination of aspects listed herein, the cartridge device is configured for forming the two separate sample mixtures in the same chamber separately.

In accordance with a twenty-eighth aspect of the present disclosure, which may be used in combination with any other aspect or combination of aspects listed herein, the reader instrument device is configured for operating and/or actuating the cartridge device to form two separate sample streams in the same flow cell from the two separate sample mixtures.

In accordance with a twenty-ninth aspect of the present disclosure, which may be used in combination with any other aspect or combination of aspects listed herein, the reader instrument is configured for numerating leukocyte cells in one of the two sample mixtures and erythrocyte cell and/or platelet cells in the other of the two sample mixtures.

In accordance with a thirtieth aspect of the present disclosure, which may be used in combination with any other aspect or combination of aspects listed herein, the cartridge device comprises an inlet port fluidly connected to the fluid conduit; and wherein the inlet port comprises a valve or an external structure to close or seal the inlet port after the sample is received into the fluid conduit.

In accordance with a thirty-first aspect of the present disclosure, which may be used in combination with any other aspect or combination of aspects listed herein, the fluid conduit has a fixed orientation and/or a fixed position in the cartridge device.

In accordance with a thirty-second aspect of the present disclosure, which may be used in combination with any other aspect or combination of aspects listed herein, the cartridge device is configured for transferring at least a portion of the reagent into the fluidic conduit to flush at least a portion of the received sample into the chamber to form a sample mixture.

In accordance with a thirty-third aspect of the present disclosure, which may be used in combination with any other aspect or combination of aspects listed herein, a method for analyzing blood cells in a sample, comprising: applying the sample to a cartridge device, which comprises a flow cell; and transferring the cartridge device into a reader instrument device for analysis, wherein the reader instrument device operates and/or actuates the cartridge device to mix at least a portion of the sample and at least a portion of a reagent comprising size reference beads to form one or more sample mixtures, and to transfer the one or more sample mixtures into the flow cell to form one or more sample streams; wherein the reader instrument device measures one or a plurality of signals from the sample streams in the flow cell; and wherein the reader instrument device analyzes the measured signals to detect, identify, characterize, quantify, and/or numerate blood cells in the sample.

In accordance with a thirty-fourth aspect of the present disclosure, which may be used in combination with any other aspect or combination of aspects listed herein, the reader instrument measures a reference signal from the size reference beads in the flow cell for analyzing the size of blood cells.

In accordance with a thirty-fifth aspect of the present disclosure, which may be used in combination with any other aspect or combination of aspects listed herein, the measured reference signal comprises an optical signal.

In accordance with a thirty-sixth aspect of the present disclosure, which may be used in combination with any other aspect or combination of aspects listed herein, the optical signal comprises light scattering, light absorption, light extinction, or fluorescence, or a combination thereof.

In accordance with a thirty-seventh aspect of the present disclosure, which may be used in combination with any other aspect or combination of aspects listed herein, the size reference beads have a diameter in the range of about 0.1-1, 1-2, 2-6, 6-8, 8-10, 10-15, 25-30, 30-50, or 50-100 μm.

In accordance with a thirty-eighth aspect of the present disclosure, which may be used in combination with any other aspect or combination of aspects listed herein, the reagent further comprises an osmolality-adjusting compound for forming sample mixtures with an osmolality in the range of about 140-160, 160-180, 180-200, 200-220, 220-240, 240-260, 260-280, 280-300, 300-320, 320-340, 340-360, 360-380, or 380-400 mOsm/L.

In accordance with a thirty-ninth aspect of the present disclosure, which may be used in combination with any other aspect or combination of aspects listed herein, the reagent further comprises a sphering compound for transforming erythrocyte cells from disk shape into sphere shape.

In accordance with a fortieth aspect of the present disclosure, which may be used in combination with any other aspect or combination of aspects listed herein, the sample streams are formed in the flow cell without a sheath flow and have a width in the range of about 1-10, 10-40, 40-100, or 100-200 μm; and a depth in the range of about 1-10, 10-40, 40-100, or 100-200 μm.

In accordance with a forty-first aspect of the present disclosure, which may be used in combination with any other aspect or combination of aspects listed herein, the measured signals comprise an optical signal.

In accordance with a forty-second aspect of the present disclosure, which may be used in combination with any other aspect or combination of aspects listed herein, the optical signal comprises light scattering, light absorption, light extinction, or fluorescence, or a combination thereof.

In accordance with a forty-third aspect of the present disclosure, which may be used in combination with any other aspect or combination of aspects listed herein, the reader instrument device analyzes the intensity of the optical signal to identify the size reference beads from the blood cells in the sample streams.

In accordance with a forty-fourth aspect of the present disclosure, which may be used in combination with any other aspect or combination of aspects listed herein, the size reference beads are fluorescent beads; and wherein the reader instrument device is configured for measuring a fluorescence signal to identify the size reference beads from the blood cells in the sample streams.

The invention claimed is:

1. A device for analyzing blood cells in a sample, comprising:
    a cartridge device, wherein the cartridge device comprises:
        a fluidic conduit configured for receiving the sample into the cartridge device;
        a chamber fluidly connected to the fluidic conduit and configured for mixing at least a portion of the sample with at least of a portion of a reagent to form one or more sample mixtures; and
        a flow cell fluidly connected to the chamber and configured for forming one or more sample streams from the one or more sample mixtures without a sheath flow; and
    a reader instrument device configured for receiving the cartridge device, measuring one or a plurality of signals from the sample streams in the flow cell, and analyzing the blood cells in the sample.

2. The device of claim 1, wherein the reader instrument device is configured for detecting, identifying, characterizing, quantifying, and/or numerating leukocyte cells, erythrocyte cells, or platelet cells, or a combination thereof.

3. The device of claim 1, wherein the flow cell has a width in the range of about 1-10, 10-40, 40-100, or 100-200 μm; and a depth in the range of about 1-10, 10-40, 40-100, or 100-200 μm.

4. The device of claim 1, wherein the flow cell has a length in the range of about 1-10, 10-100, 100-1,000, 1,000-5,000 μm, or 5,000-10,000 μm.

5. The device of claim 1, wherein the flow cell comprises a transparent surface for an optical signal from the sample streams in the flow cell; and wherein the reader instrument device is configured for measuring the optical signal.

6. The device of claim 5, wherein the optical signal comprises light scattering, light absorption, light extinction, or fluorescence, or a combination thereof.

7. The device of claim 1, wherein the chamber has a volume in the range of about 0.01-0.1 ml, 0.1-0.2 ml, 0.2-0.4 ml, 0.4-0.8 ml, 0.8-2 ml, or 2-10 ml.

8. The device of claim 1, wherein the chamber comprises a venting port configured for receiving a pneumatic pressure source.

9. The device of claim 8, wherein, when the cartridge device is in use, the chamber is so positioned that at least a portion of the fluid inside the chamber is pulled by gravity away from the venting port and/or towards the lower bottom of the chamber.

10. The device of claim 1, wherein the cartridge device further comprises a cuvette; and wherein the reader instrument device is configured for measuring a signal from the sample mixtures in the cuvette to determine the hemoglobin concentration in the sample.

11. The device of claim 10, wherein the reader instrument device is configured for measuring a light absorption signal from the sample mixtures in the cuvette to determine the hemoglobin concentration in the sample.

12. The device of claim 1, wherein the reagent comprises an osmolality-adjusting compound for forming sample mixtures with an osmolality in the range of about 140-160, 160-180, 180-200, 200-220, 220-240, 240-260, 260-280, 280-300, 300-320, 320-340, 340-360, 360-380, or 380-400 mOsm/L.

13. The device of claim 1, wherein the reagent comprises a sphering compound for transforming erythrocyte cells from disk shape into sphere shape.

14. The device of claim 1, wherein the reagent comprises a fluorescent labeling reagent for labeling nucleic acids in blood cells in the sample mixtures; and wherein the reader instrument device is configured for measuring a fluorescence signal from the sample streams in the flow cell.

15. The device of claim 1, wherein the reagent comprises a lysing compound for lysing erythrocyte cells in the sample mixtures to release hemoglobin.

16. The device of claim 1, wherein the cartridge device further comprises a flow sensor fluidly connected to the flow cell; and wherein the reader instrument device is configured for measuring a sensing signal from the flow sensor when the sample streams enter the flow sensor.

17. The device of claim 16, wherein the reader instrument device is configured for using the sensing signal from the flow sensor to determine the absolute count of the blood cells in the sample.

18. The device of claim 16, wherein the measured sensing signal comprises an optical signal.

19. The device of claim 16, wherein the fluidic connection between the flow cell and the flow sensor is configured for a sample stream to have the same flow rate flowing through the flow cell and the flow sensor.

20. The device of claim 16, wherein the flow sensor comprises a fluidic channel and a sensing zone on the fluidic channel, wherein the fluidic channel is fluidly connected to the flow cell to allow the sample streams to flow through; and wherein the reader instrument device is configured for measuring a sensing signal from the sensing zone when the sample streams enter the sensing zone.

21. The device of claim 1, further comprising a microfluidic channel fluidly connected to the chamber and a valve on the microfluidic channel, wherein the microfluidic channel has a cross section in the range of about 0.001-0.01 $mm^2$, 0.01-0.1 $mm^2$, 0.1-0.25 $mm^2$, 0.25-0.5 $mm^2$, 0.5-1 $mm^2$, 1-2 $mm^2$, or 2-10 $mm^2$.

22. The device of claim 21, wherein the valve is a passive valve that comprises one of the following structures: (i) a patch of hydrophobic surface in a channel having a hydrophilic surface, (ii) a patch of hydrophilic surface in a channel having a hydrophobic surface, (iii) an enlargement of the channel cross section along the flow direction in a channel having a hydrophilic surface, and (iv) a contraction of the channel cross section along the flow direction in a channel having a hydrophobic surface.

23. The device of claim 1, wherein the reader instrument device is configured for applying an actuation mechanism to control the fluid transfer in the cartridge device, and wherein the actuation mechanism comprises a pneumatic pressure source.

24. The device of claim 23, wherein the applied pneumatic pressure source actuates the cartridge device to transfer the sample mixtures from the chamber into the flow cell to form the sample streams.

25. The device of claim 23, wherein the cartridge device is configured for mixing two separate portions of the sample received in the fluidic conduit with the reagent to form two separate sample mixtures.

26. The device of claim 24, wherein the cartridge device is configured for forming the two separate sample mixtures in the same chamber separately.

27. The device of claim 24, wherein the reader instrument device is configured for operating and/or actuating the cartridge device to form two separate sample streams in the same flow cell from the two separate sample mixtures.

28. The device of claim 23, wherein the reader instrument is configured for numerating leukocyte cells in one of the two sample mixtures and erythrocyte cell and/or platelet cells in the other of the two sample mixtures.

29. The device of claim 1, wherein the cartridge device comprises an inlet port fluidly connected to the fluid conduit; and wherein the inlet port comprises a valve or an external structure to close or seal the inlet port after the sample is received into the fluid conduit.

30. The device of claim 1, wherein the fluid conduit has a fixed orientation and/or a fixed position in the cartridge device.

31. The device of claim 1, wherein the cartridge device is configured for transferring at least a portion of the reagent into the fluidic conduit to flush at least a portion of the received sample into the chamber to form a sample mixture.

32. The device of claim 1, wherein the reagent consists of a fluorescent labeling agent.

33. The device of claim 1, wherein the reagent consists essentially of a fluorescent labeling agent.

34. The device of claim 1, wherein the reagent does not contain a magnetic material.

35. The device of claim 1, wherein the flow cell is configured for forming one sample stream without branching.

* * * * *